US009957539B2

(12) United States Patent
Ono

(10) Patent No.: US 9,957,539 B2
(45) Date of Patent: May 1, 2018

(54) METHOD FOR USING HEXENOL GLYCOSYL TRANSFERASE

(71) Applicant: SUNTORY HOLDINGS LIMITED, Osaka (JP)

(72) Inventor: Eiichiro Ono, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 45 days.

(21) Appl. No.: 14/908,889

(22) PCT Filed: Aug. 1, 2014

(86) PCT No.: PCT/JP2014/070961
§ 371 (c)(1),
(2) Date: Jan. 29, 2016

(87) PCT Pub. No.: WO2015/016393
PCT Pub. Date: Feb. 5, 2015

(65) Prior Publication Data

US 2016/0319317 A1 Nov. 3, 2016

(30) Foreign Application Priority Data

Aug. 2, 2013 (JP) ................................ 2013-161579

(51) Int. Cl.

*C12P 19/18* (2006.01)
*C12P 19/44* (2006.01)
*C12N 9/10* (2006.01)
*C12P 19/02* (2006.01)

(52) U.S. Cl.

CPC ............ *C12P 19/18* (2013.01); *C12N 9/1048* (2013.01); *C12P 19/02* (2013.01); *C12Y 204/00* (2013.01)

(58) Field of Classification Search

None
See application file for complete search history.

(56) References Cited

U.S. PATENT DOCUMENTS

2005/0277766 A1 12/2005 Moller et al.
2006/0275877 A1* 12/2006 Hansen ................ C12N 9/1051 435/117
2013/0125263 A1 5/2013 Apuya et al.
2013/0171328 A1 7/2013 Kishore et al.

FOREIGN PATENT DOCUMENTS

JP 2003-515345 5/2003
JP 2013176361 A * 9/2013
WO 01/40491 A2 6/2001
WO 2011/140329 11/2011
WO 2011/153378 12/2011
WO 2013/110673 8/2013

OTHER PUBLICATIONS

Sang, H., Mechanisms of Development 121:1179-1186, 2004.*
Vain et al., Theor. Appl. Genet. 105:878-889, 2002.*
Ohgami et al., “Volatile Glycosylation in Tea Plants: Sequential Glycosylations for the Biosynthesis of Aroma β-Primeverosides Are Catalyzed by Two Camellia sinensis Glycosyltransferases”, Plant Physiol. 168:464-477, 2015.*
Bönisch et al., “A UDP-Glucose:Monoterpenol Glucosyltransferase Adds to the Chemical Diversity of the Grapevine Metabolome”, Plant Physiol. 165:561-581, Jun. 2014.*
Machine translation of JP2013176361A, obtained from Espacenet.com on Dec. 12, 2017, 27 pages (Year: 2017).*
Wang et al., “Analysis of Glycosidically Bound Aroma Precursors in Tea Leaves. 1. Qualitative and Quantitative Analyses of Glycosides with Aglycon as Aroma Compounds,” *J. Agric. Food Chem.*, vol. 48 , pp. 5411-5418, 2000.
Richman et al., “UDP-glycosyltransferase 85C1,” http://www.ncbi.nlm.nih.gov/protein/Q6VAA4, Oct. 31, 2006.
Richman et al., “UDP-glycosyltransferase 85A8,” http://www.ncbi.nlm.nih.gov/protein/Q6VAB3, Oct. 31, 2006.
Mizutani et al., “Cloning of β-Primeverosidase from Tea Leaves, a Key Enzyme in Tea Aroma Formation,” *Plant Physiol.*, vol. 130, pp. 2164-2176, 2002.
Matsui et al., “Green leaf volatiles: hydroperoxide lyase pathway of oxylipin metabolism,” *Current Opinion in Plant Biology*, vol. 9, pp. 274-280, 2006.
Leushkin et al., “hypothetical protein M569_00822, partial [Genlisea aurea],”http://www.ncbi.nlm.nih.gov/protein/EPS73934, Jul. 26, 2013.
Arimura et al., “Chemical and Molecular Ecology of Herbivore-Induced Plant Volatiles: Proximate Factors and Their Ultimate Functions,” *Plant Cell Physiol.*, vol. 50, No. 5, pp. 911-923, 2009.
International Search Report and Written Opinion issued in PCT/JP2014/070961, dated Nov. 18, 2014, along with English language translations thereof.
Hansen et al., “The in vitro substrate regiospecificity of recombinant UGT85B1, the cyanohydrin glucosyltransferase from *Sorghum bicolor,” Phytochemistry*, vol. 64, No. 1, pp. 143-151, 2003.
Partial Supplementary European Search Report issued in EP Patent Application No. 14831646.6, dated Mar. 13, 2017.

* cited by examiner

*Primary Examiner* — David Steadman
(74) *Attorney, Agent, or Firm* — Greenblum & Bernstein, P.L.C.

(57) ABSTRACT

A method for producing a hexenol glycoside using a hexenol glycosyltransferase. A transformant transformed with a gene encoding a hexenol glycosyltransferase and a method for preparing such a transformant.

9 Claims, 10 Drawing Sheets

1A
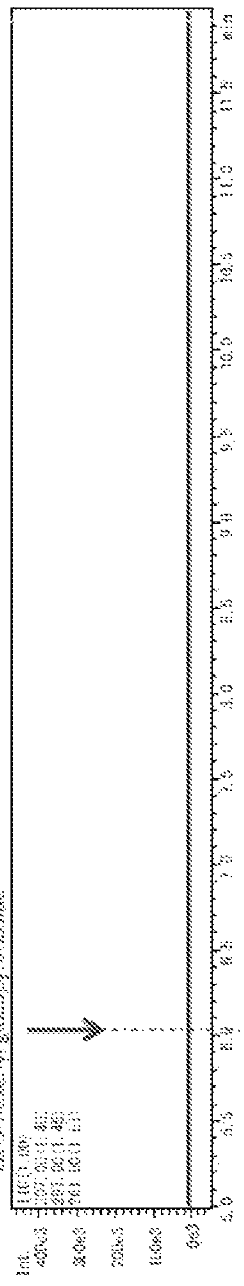
1B
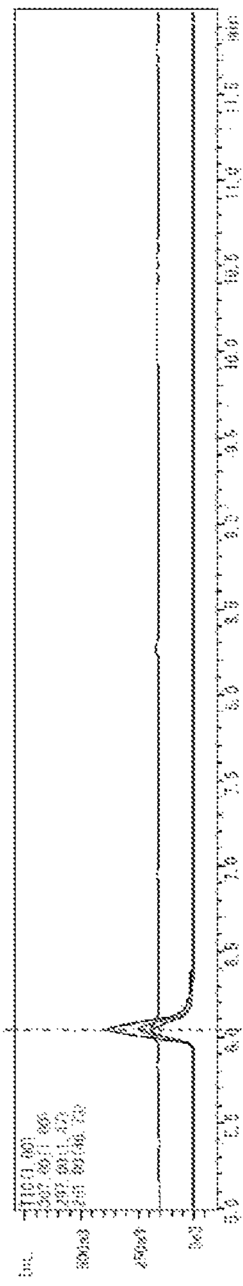
1C
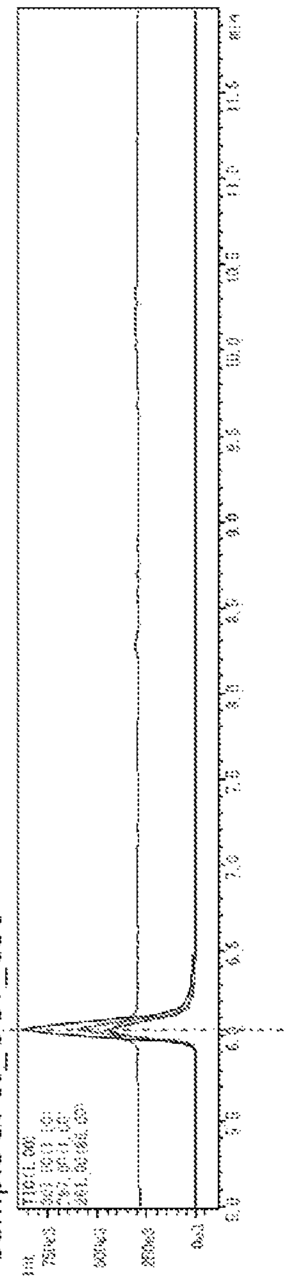

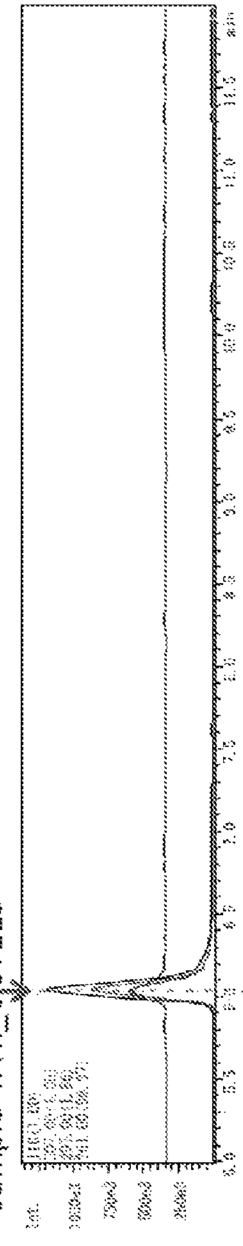
2A
Sample 4: HI_UGT119
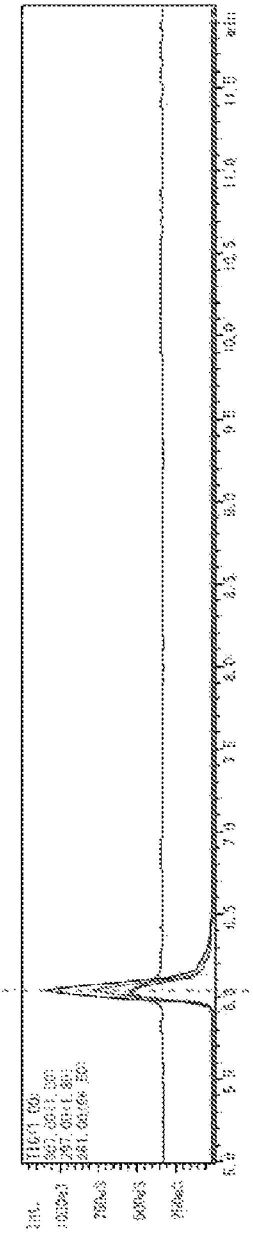
2B
Sample 5: HI_UGT127
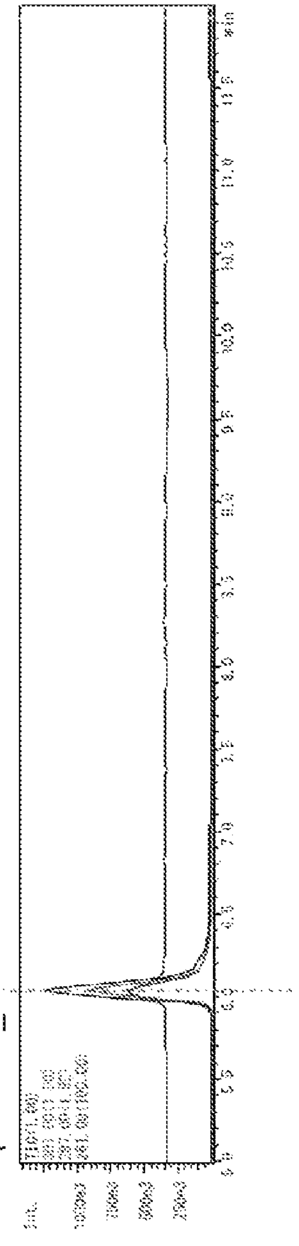
2C
Sample 6: HI_UGT279

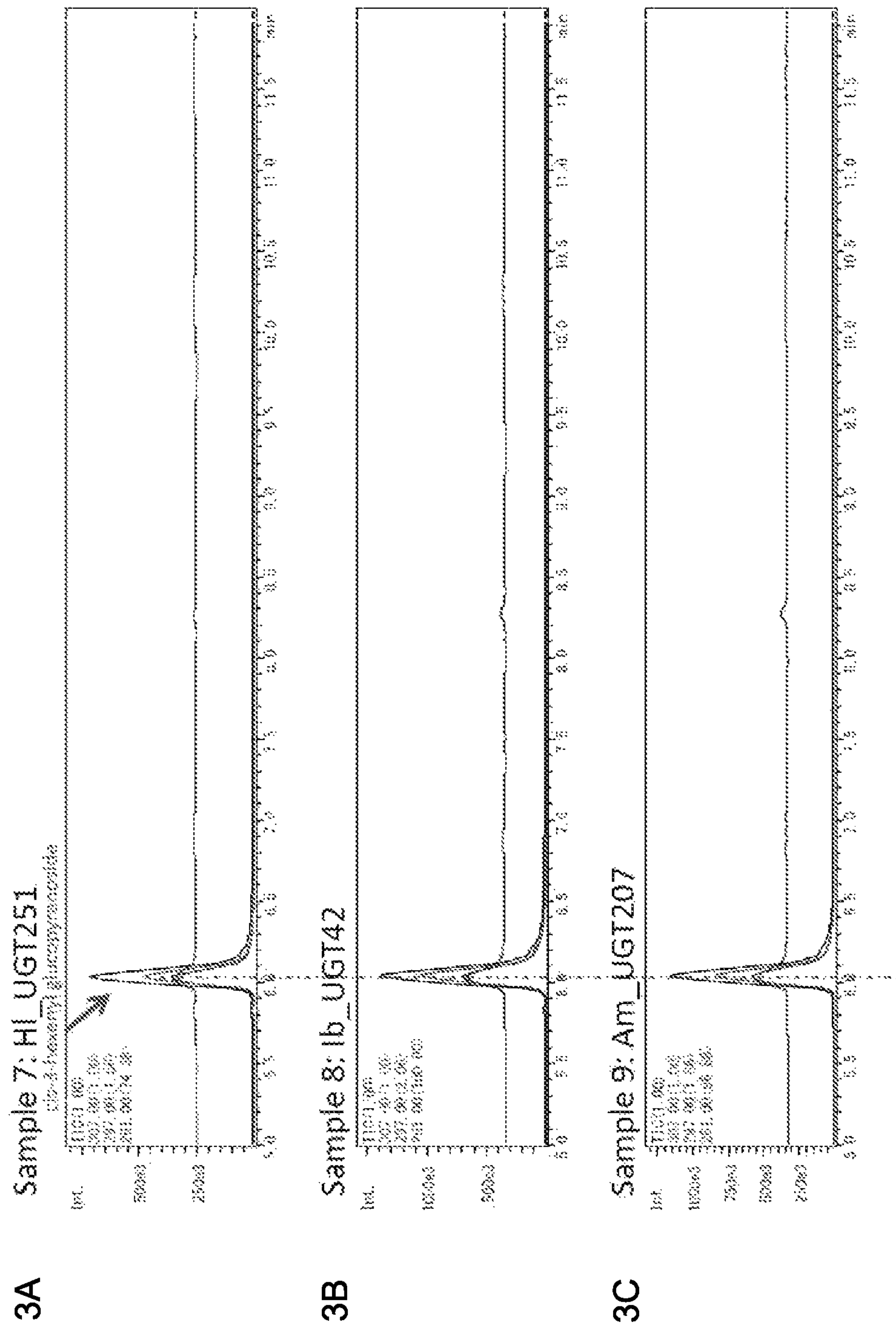
3A
Sample 7: Hl_UGT251
3B
Sample 8: Ib_UGT42
3C
Sample 9: Am_UGT207

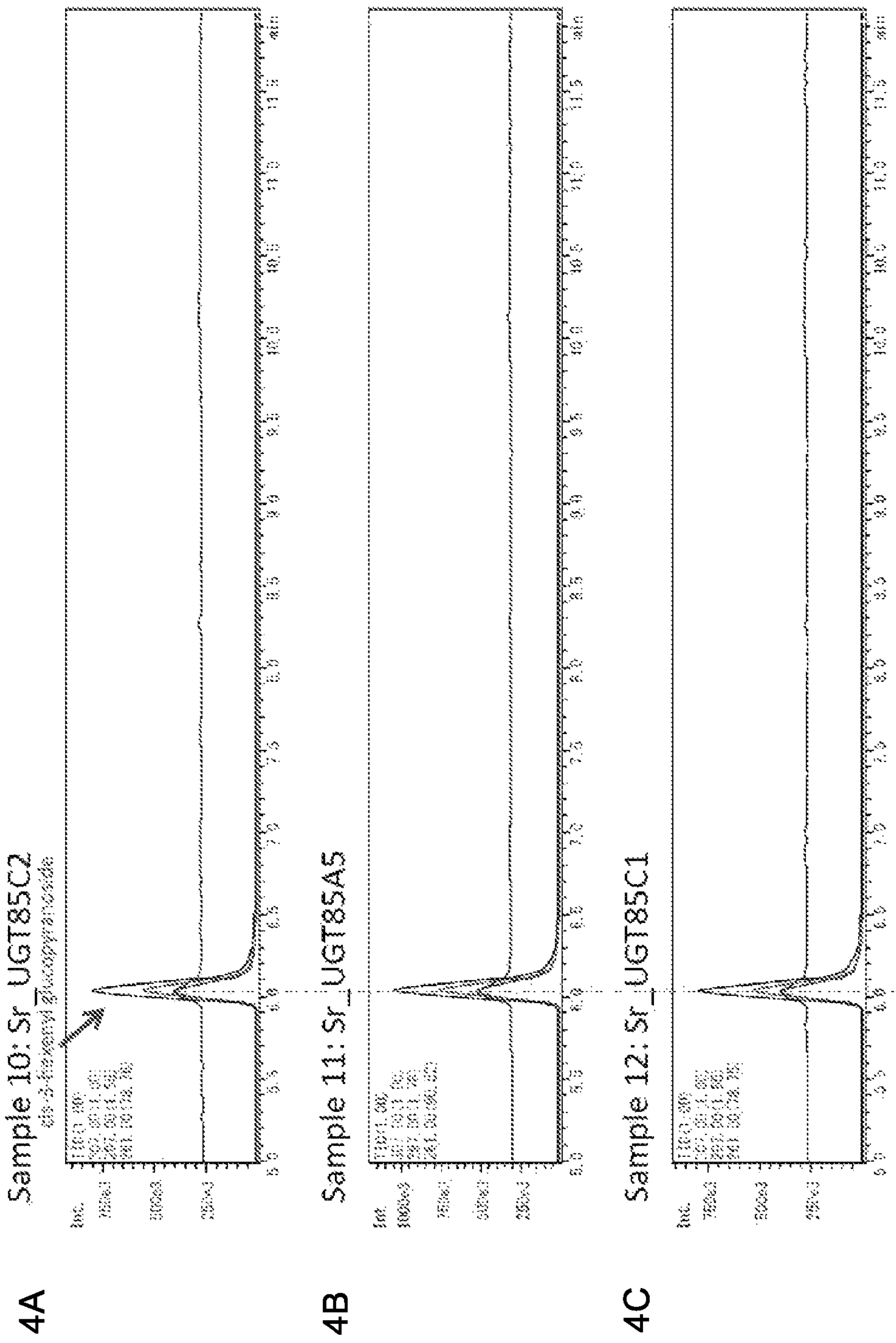
4A
Sample 10: Sr_UGT85C2
4B
Sample 11: Sr_UGT85A5
4C
Sample 12: Sr_UGT85C1

5A
Sample 13: At_UGT85A1
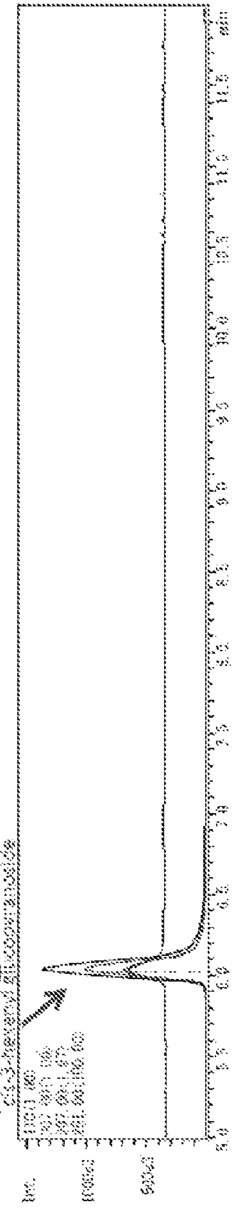
5B
Sample 14: At_UGT85A3
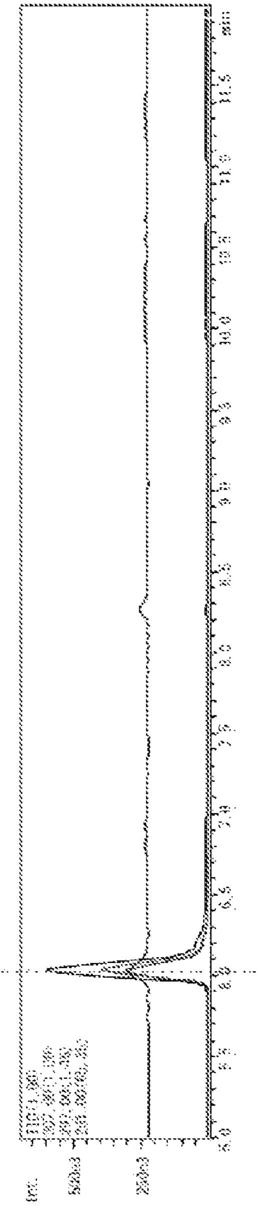
5C
Sample 15: cis-3-hexenyl glucopyranoside (Standard)
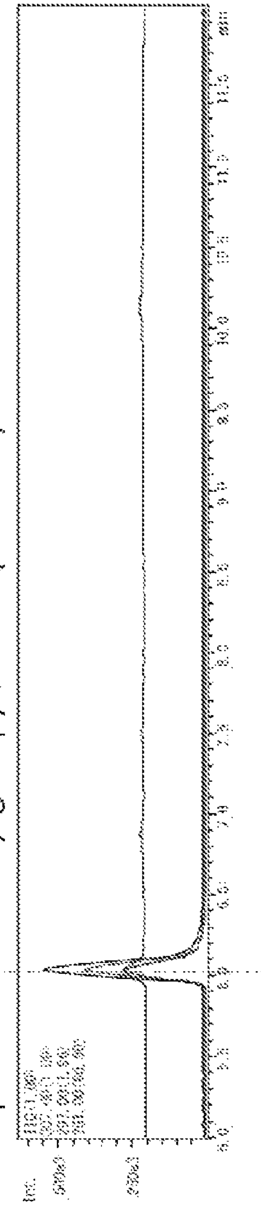

6A
Sample 16: Vv_UGT020
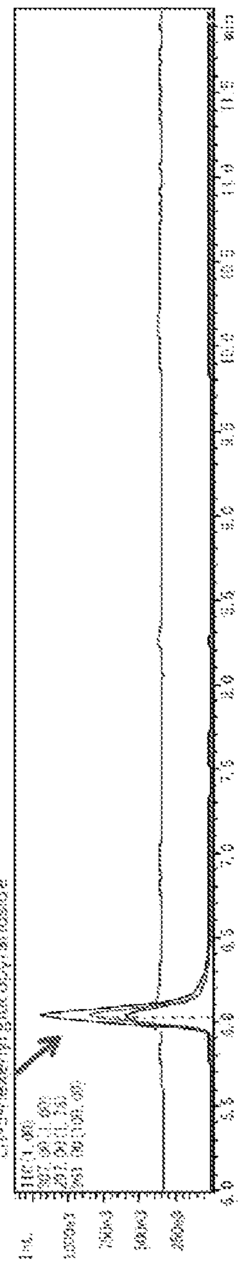
6B
Sample 17: Vv_UGT734
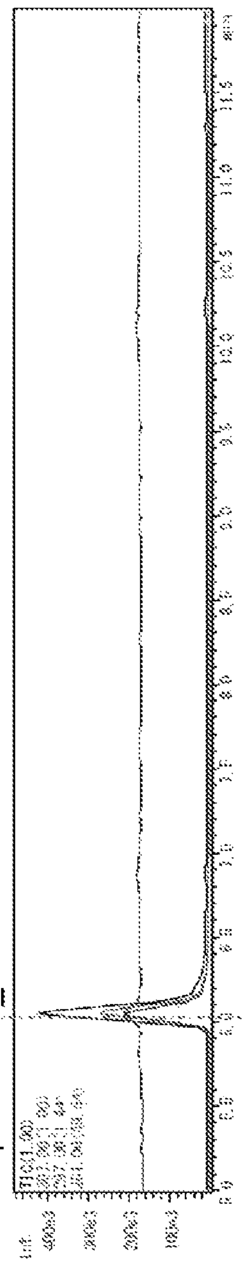
6C
Sample 18: Vv_UGT744
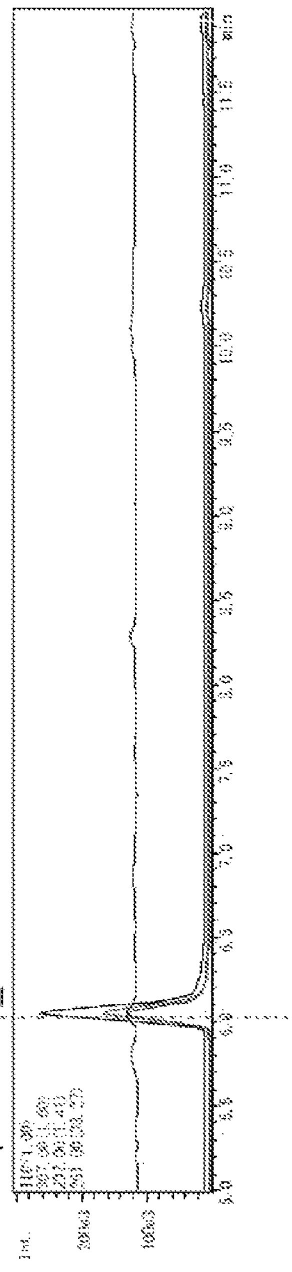

```
SEQUENCE LISTING

<160> NUMBER OF SEQ ID NOS: 40

<210> SEQ ID NO 1
<211> LENGTH: 1458
<212> TYPE: DNA
```

```
<213> ORGANISM: Camellia sinensis
<220> FEATURE:
<221> NAME/KEY: CDS
<222> LOCATION: (1)..(1455)

<400> SEQUENCE: 1

atg ggt agc aga aag cag ccc cat gcc gtt tgt gta ccc ttt cca gca       48
Met Gly Ser Arg Lys Gln Pro His Ala Val Cys Val Pro Phe Pro Ala
1               5                   10                  15

caa ggt cac ata aac cca atg atg caa ctg gcc aag ctt cta cac tct       96
Gln Gly His Ile Asn Pro Met Met Gln Leu Ala Lys Leu Leu His Ser
            20                  25                  30

aga ggc ttc tac atc acc ttc gtc aac acc gag ttc aac cac aga cgc      144
Arg Gly Phe Tyr Ile Thr Phe Val Asn Thr Glu Phe Asn His Arg Arg
        35                  40                  45

ttg ctt caa tcc aaa ggt cct gaa ttt cta aag ggc tgt gct gat ttc      192
Leu Leu Gln Ser Lys Gly Pro Glu Phe Leu Lys Gly Cys Ala Asp Phe
    50                  55                  60

cag ttt gag tct ata ccg gat ggg ctg cca ccg tcc gat cgt gat gcc      240
Gln Phe Glu Ser Ile Pro Asp Gly Leu Pro Pro Ser Asp Arg Asp Ala
65                  70                  75                  80

act caa gat cct ccg acc ctc tgc atc gca atg cga gac aac tgt ttg      288
Thr Gln Asp Pro Pro Thr Leu Cys Ile Ala Met Arg Asp Asn Cys Leu
                85                  90                  95

gat ccc ttt cga gtt tta tta aaa aag ctc aac aac aac aac aac tcg      336
Asp Pro Phe Arg Val Leu Leu Lys Lys Leu Asn Asn Asn Asn Asn Ser
            100                 105                 110

att gca tcg cgg caa gtg cca ggt gtt acg tgc gta gta tct gat gga      384
Ile Ala Ser Arg Gln Val Pro Gly Val Thr Cys Val Val Ser Asp Gly
        115                 120                 125

gcg atg aac ttt gcc atg aaa gcc gca gaa gaa gct ggg att ccc gag      432
Ala Met Asn Phe Ala Met Lys Ala Ala Glu Glu Ala Gly Ile Pro Glu
    130                 135                 140

gtg caa ttt tgg act gca tcg gct tgt ggc ttc atg ggc tac ctt cac      480
Val Gln Phe Trp Thr Ala Ser Ala Cys Gly Phe Met Gly Tyr Leu His
145                 150                 155                 160

tac cct caa ctt gtc caa aga ggc att ttc cca ttc aaa gat gag agt      528
Tyr Pro Gln Leu Val Gln Arg Gly Ile Phe Pro Phe Lys Asp Glu Ser
                165                 170                 175

ttc caa agt gat ggc tct ctt gac aca act ata gat tgg atc cct ggc      576
Phe Gln Ser Asp Gly Ser Leu Asp Thr Thr Ile Asp Trp Ile Pro Gly
            180                 185                 190

atg aga aac att cgg ctc aag gac atg cca tcc ttt atc aga acc aca      624
Met Arg Asn Ile Arg Leu Lys Asp Met Pro Ser Phe Ile Arg Thr Thr
        195                 200                 205

gat cct aat gac atc ttg ttc aat tac ctg agt gag gaa gta caa aat      672
Asp Pro Asn Asp Ile Leu Phe Asn Tyr Leu Ser Glu Glu Val Gln Asn
    210                 215                 220

tgc tta aaa gca tct gca atc atc ttc aac act ttc gac aca ttg gag      720
Cys Leu Lys Ala Ser Ala Ile Ile Phe Asn Thr Phe Asp Thr Leu Glu
225                 230                 235                 240

cat caa gta ttg cag gct atc gcg tcc aag ttc cat aac att tac act      768
His Gln Val Leu Gln Ala Ile Ala Ser Lys Phe His Asn Ile Tyr Thr
                245                 250                 255

att ggg cca ctt tct ttg cta tcc aag cag gtg att gat ggt gaa ttc      816
Ile Gly Pro Leu Ser Leu Leu Ser Lys Gln Val Ile Asp Gly Glu Phe
            260                 265                 270

aag tca ctt aat tca agt tta tgg aag gaa gac acg aaa tgc ctc caa      864
Lys Ser Leu Asn Ser Ser Leu Trp Lys Glu Asp Thr Lys Cys Leu Gln
        275                 280                 285
```

```
tgg ctt gat acg aag gaa cca aac tct gtt gtg tat gtc aac tat gga       912
Trp Leu Asp Thr Lys Glu Pro Asn Ser Val Val Tyr Val Asn Tyr Gly
    290                 295                 300

agt ata acc gtc atg aca gac caa cat ctg aag gaa ttt gca tgg ggg       960
Ser Ile Thr Val Met Thr Asp Gln His Leu Lys Glu Phe Ala Trp Gly
305                 310                 315                 320

ctt gca aat agt aag cac cca ttt ctt tgg atc gtt cga cct gat att      1008
Leu Ala Asn Ser Lys His Pro Phe Leu Trp Ile Val Arg Pro Asp Ile
                325                 330                 335

gta atg ggc gat tca gca atc ttg cct gaa cac ttt gtt gag gag act      1056
Val Met Gly Asp Ser Ala Ile Leu Pro Glu His Phe Val Glu Glu Thr
            340                 345                 350

aaa gat aga gga ttg cta gta agt tgg tgc cca caa gaa caa gta ctt      1104
Lys Asp Arg Gly Leu Leu Val Ser Trp Cys Pro Gln Glu Gln Val Leu
        355                 360                 365

tcc cac cca tca att ggt gtc ttt cta aca cat tgt ggt tgg aac tct      1152
Ser His Pro Ser Ile Gly Val Phe Leu Thr His Cys Gly Trp Asn Ser
    370                 375                 380

aca ttg gaa agc ata tgt gga gga gta ccc ata att tgt tgg cct ttc      1200
Thr Leu Glu Ser Ile Cys Gly Gly Val Pro Ile Ile Cys Trp Pro Phe
385                 390                 395                 400

ttt gcc gag caa caa aca aat tgt cga tat gca tgc acc gag tgg ggg      1248
Phe Ala Glu Gln Gln Thr Asn Cys Arg Tyr Ala Cys Thr Glu Trp Gly
                405                 410                 415

att gga atg gag gtt aat cat gat gtg aag cgc aat gaa att gta gca      1296
Ile Gly Met Glu Val Asn His Asp Val Lys Arg Asn Glu Ile Val Ala
            420                 425                 430

ctt att aat gaa atg ttg gaa ggt gat aag ggg aag caa atg cga aag      1344
Leu Ile Asn Glu Met Leu Glu Gly Asp Lys Gly Lys Gln Met Arg Lys
        435                 440                 445

aaa gct ctc aaa ttg aag aag gaa gca gaa gaa gca act gat gtt gga      1392
Lys Ala Leu Lys Leu Lys Lys Glu Ala Glu Glu Ala Thr Asp Val Gly
    450                 455                 460

ggg tta tcc tac aat aac ttt gat agg ctc att aaa gaa gct ctt cac      1440
Gly Leu Ser Tyr Asn Asn Phe Asp Arg Leu Ile Lys Glu Ala Leu His
465                 470                 475                 480

tat tgt gag caa tac taa                                              1458
Tyr Cys Glu Gln Tyr
                485


<210> SEQ ID NO 2
<211> LENGTH: 485
<212> TYPE: PRT
<213> ORGANISM: Camellia sinensis

<400> SEQUENCE: 2

Met Gly Ser Arg Lys Gln Pro His Ala Val Cys Val Pro Phe Pro Ala
1               5                   10                  15

Gln Gly His Ile Asn Pro Met Met Gln Leu Ala Lys Leu Leu His Ser
            20                  25                  30

Arg Gly Phe Tyr Ile Thr Phe Val Asn Thr Glu Phe Asn His Arg Arg
        35                  40                  45

Leu Leu Gln Ser Lys Gly Pro Glu Phe Leu Lys Gly Cys Ala Asp Phe
    50                  55                  60

Gln Phe Glu Ser Ile Pro Asp Gly Leu Pro Pro Ser Asp Arg Asp Ala
65                  70                  75                  80

Thr Gln Asp Pro Pro Thr Leu Cys Ile Ala Met Arg Asp Asn Cys Leu
                85                  90                  95

Asp Pro Phe Arg Val Leu Leu Lys Lys Leu Asn Asn Asn Asn Asn Ser
```

```
            100                 105                 110

Ile Ala Ser Arg Gln Val Pro Gly Val Thr Cys Val Val Ser Asp Gly
        115                 120                 125

Ala Met Asn Phe Ala Met Lys Ala Ala Glu Glu Ala Gly Ile Pro Glu
    130                 135                 140

Val Gln Phe Trp Thr Ala Ser Ala Cys Gly Phe Met Gly Tyr Leu His
145                 150                 155                 160

Tyr Pro Gln Leu Val Gln Arg Gly Ile Phe Pro Phe Lys Asp Glu Ser
                165                 170                 175

Phe Gln Ser Asp Gly Ser Leu Asp Thr Thr Ile Asp Trp Ile Pro Gly
            180                 185                 190

Met Arg Asn Ile Arg Leu Lys Asp Met Pro Ser Phe Ile Arg Thr Thr
        195                 200                 205

Asp Pro Asn Asp Ile Leu Phe Asn Tyr Leu Ser Glu Glu Val Gln Asn
    210                 215                 220

Cys Leu Lys Ala Ser Ala Ile Ile Phe Asn Thr Phe Asp Thr Leu Glu
225                 230                 235                 240

His Gln Val Leu Gln Ala Ile Ala Ser Lys Phe His Asn Ile Tyr Thr
                245                 250                 255

Ile Gly Pro Leu Ser Leu Leu Ser Lys Gln Val Ile Asp Gly Glu Phe
            260                 265                 270

Lys Ser Leu Asn Ser Ser Leu Trp Lys Glu Asp Thr Lys Cys Leu Gln
        275                 280                 285

Trp Leu Asp Thr Lys Glu Pro Asn Ser Val Val Tyr Val Asn Tyr Gly
    290                 295                 300

Ser Ile Thr Val Met Thr Asp Gln His Leu Lys Glu Phe Ala Trp Gly
305                 310                 315                 320

Leu Ala Asn Ser Lys His Pro Phe Leu Trp Ile Val Arg Pro Asp Ile
                325                 330                 335

Val Met Gly Asp Ser Ala Ile Leu Pro Glu His Phe Val Glu Glu Thr
            340                 345                 350

Lys Asp Arg Gly Leu Leu Val Ser Trp Cys Pro Gln Glu Gln Val Leu
        355                 360                 365

Ser His Pro Ser Ile Gly Val Phe Leu Thr His Cys Gly Trp Asn Ser
    370                 375                 380

Thr Leu Glu Ser Ile Cys Gly Gly Val Pro Ile Ile Cys Trp Pro Phe
385                 390                 395                 400

Phe Ala Glu Gln Gln Thr Asn Cys Arg Tyr Ala Cys Thr Glu Trp Gly
                405                 410                 415

Ile Gly Met Glu Val Asn His Asp Val Lys Arg Asn Glu Ile Val Ala
            420                 425                 430

Leu Ile Asn Glu Met Leu Glu Gly Asp Lys Gly Lys Gln Met Arg Lys
        435                 440                 445

Lys Ala Leu Lys Leu Lys Lys Glu Ala Glu Glu Ala Thr Asp Val Gly
    450                 455                 460

Gly Leu Ser Tyr Asn Asn Phe Asp Arg Leu Ile Lys Glu Ala Leu His
465                 470                 475                 480

Tyr Cys Glu Gln Tyr
                485
```

<210> SEQ ID NO 3
<211> LENGTH: 1422
<212> TYPE: DNA
<213> ORGANISM: Camellia sinensis

```
<220> FEATURE:
<221> NAME/KEY: CDS
<222> LOCATION: (1)..(1419)

<400> SEQUENCE: 3

atg gct aag ctt cat ttc ttc ttc ttt ccg gtg atg gct caa ggt cac      48
Met Ala Lys Leu His Phe Phe Phe Phe Pro Val Met Ala Gln Gly His
1               5                   10                  15

atg atc cca act ctg gac atg gca aag ctc ttc gcc tcc cat ggc gtt      96
Met Ile Pro Thr Leu Asp Met Ala Lys Leu Phe Ala Ser His Gly Val
            20                  25                  30

aaa gcc acc ata atc acc acc cct ctc aac gcc cct tac ttc acc aga     144
Lys Ala Thr Ile Ile Thr Thr Pro Leu Asn Ala Pro Tyr Phe Thr Arg
        35                  40                  45

tca atc caa aga acc cat cac tct atc tct gtc ctc acc ctc aaa ttc     192
Ser Ile Gln Arg Thr His His Ser Ile Ser Val Leu Thr Leu Lys Phe
    50                  55                  60

cca gca gtc gag gcc ggt tta gtg gaa ggt tgc gag agc gtc gat caa     240
Pro Ala Val Glu Ala Gly Leu Val Glu Gly Cys Glu Ser Val Asp Gln
65                  70                  75                  80

atc cct tcc ccc gac atg ctt ccc aac ttc ttg aag gcc acc acc atg     288
Ile Pro Ser Pro Asp Met Leu Pro Asn Phe Leu Lys Ala Thr Thr Met
                85                  90                  95

cta caa gac ccg ctc gag cga ctc ctc caa gac tcc cgc cct gat tgc     336
Leu Gln Asp Pro Leu Glu Arg Leu Leu Gln Asp Ser Arg Pro Asp Cys
            100                 105                 110

ctc gtc gca gac atg ttc ttc ccc tgg gcc act cat gtc gca gcc aag     384
Leu Val Ala Asp Met Phe Phe Pro Trp Ala Thr His Val Ala Ala Lys
        115                 120                 125

ttc aat att ccg agg ctg gtt ttc cat ggg act ggc ttc ttc act ttg     432
Phe Asn Ile Pro Arg Leu Val Phe His Gly Thr Gly Phe Phe Thr Leu
    130                 135                 140

tgc gct tcc gag aat ctg agg ctt tac atg cct cag gcg agt gtg tcc     480
Cys Ala Ser Glu Asn Leu Arg Leu Tyr Met Pro Gln Ala Ser Val Ser
145                 150                 155                 160

tcc gac gat gaa ccc ttt ctg gtg cct aat ctt cct cac aaa ata atg     528
Ser Asp Asp Glu Pro Phe Leu Val Pro Asn Leu Pro His Lys Ile Met
                165                 170                 175

tta act agg tcg cag ctg ccg gag aat gaa cga tgc gat aca gag act     576
Leu Thr Arg Ser Gln Leu Pro Glu Asn Glu Arg Cys Asp Thr Glu Thr
            180                 185                 190

ggc ttg tcc acg atg ctg aag caa gtt aaa gag acg gag ctg aca agc     624
Gly Leu Ser Thr Met Leu Lys Gln Val Lys Glu Thr Glu Leu Thr Ser
        195                 200                 205

tat gga gtt att gtc aat agt ttc tac gag ctt gaa ccg gac tat gct     672
Tyr Gly Val Ile Val Asn Ser Phe Tyr Glu Leu Glu Pro Asp Tyr Ala
    210                 215                 220

gat tac tac agg aat gtt ttg gga aga agg gcc tgg cat att ggc cct     720
Asp Tyr Tyr Arg Asn Val Leu Gly Arg Arg Ala Trp His Ile Gly Pro
225                 230                 235                 240

gtt tcg ctc tgc aat cgg gag gta gaa gac aaa gca cag aga ggt aaa     768
Val Ser Leu Cys Asn Arg Glu Val Glu Asp Lys Ala Gln Arg Gly Lys
                245                 250                 255

gaa tca gcc att gat gag gtt gag tgt ttg aaa tgg ctt aat tcg aag     816
Glu Ser Ala Ile Asp Glu Val Glu Cys Leu Lys Trp Leu Asn Ser Lys
            260                 265                 270

aaa ccc aat tct gta att tac gta tgt ttt gga agt ttg ggc gat ttt     864
Lys Pro Asn Ser Val Ile Tyr Val Cys Phe Gly Ser Leu Gly Asp Phe
        275                 280                 285

act gct tct cag ttg ttt gag ctt gcg atg ggg ctt gaa gct tca ggg     912
```

```
Thr Ala Ser Gln Leu Phe Glu Leu Ala Met Gly Leu Glu Ala Ser Gly
    290                 295                 300

caa caa ttc atc tgg gtt gtg agg aaa ggc aag atc gaa gaa gac ggt      960
Gln Gln Phe Ile Trp Val Val Arg Lys Gly Lys Ile Glu Glu Asp Gly
305                 310                 315                 320

gat gag aag cgg ttg ccg gag gag ttt gag gag aga atg aag gac aag     1008
Asp Glu Lys Arg Leu Pro Glu Glu Phe Glu Glu Arg Met Lys Asp Lys
                325                 330                 335

gga cta atc ata aga ggt tgg gca cct caa gtt ttg att ctt gat cat     1056
Gly Leu Ile Ile Arg Gly Trp Ala Pro Gln Val Leu Ile Leu Asp His
            340                 345                 350

gaa tcg att ggg ggt ttt gtg act cac tgc ggg tgg aat tcg atc ctg     1104
Glu Ser Ile Gly Gly Phe Val Thr His Cys Gly Trp Asn Ser Ile Leu
        355                 360                 365

gaa ggt gtt tgt gcc ggc gtc cca atg gtg act tgg cca cga ttt gcg     1152
Glu Gly Val Cys Ala Gly Val Pro Met Val Thr Trp Pro Arg Phe Ala
    370                 375                 380

gag caa ttc tat aat gag aag ttg gtg act gag gtt ttg aga att ggg     1200
Glu Gln Phe Tyr Asn Glu Lys Leu Val Thr Glu Val Leu Arg Ile Gly
385                 390                 395                 400

gtt ggg gtt ggt gct cgg caa tgg cag att gga gca gga agt gat tgt     1248
Val Gly Val Gly Ala Arg Gln Trp Gln Ile Gly Ala Gly Ser Asp Cys
                405                 410                 415

atc aag gga gaa aca ata gca aaa gca gtg aag cgg gtt atg gag gct     1296
Ile Lys Gly Glu Thr Ile Ala Lys Ala Val Lys Arg Val Met Glu Ala
            420                 425                 430

ggg gaa gaa gct gag gga atg aga acc cga gct agg gca gct aag gat     1344
Gly Glu Glu Ala Glu Gly Met Arg Thr Arg Ala Arg Ala Ala Lys Asp
        435                 440                 445

atg gcg aag aag gct gtt gaa gag ggt gga tca tct tat tct gac ctc     1392
Met Ala Lys Lys Ala Val Glu Glu Gly Gly Ser Ser Tyr Ser Asp Leu
    450                 455                 460

aat gct ctg ata caa gaa atg agt tca taa                             1422
Asn Ala Leu Ile Gln Glu Met Ser Ser
465                 470


<210> SEQ ID NO 4
<211> LENGTH: 473
<212> TYPE: PRT
<213> ORGANISM: Camellia sinensis

<400> SEQUENCE: 4

Met Ala Lys Leu His Phe Phe Phe Phe Pro Val Met Ala Gln Gly His
1               5                   10                  15

Met Ile Pro Thr Leu Asp Met Ala Lys Leu Phe Ala Ser His Gly Val
            20                  25                  30

Lys Ala Thr Ile Ile Thr Thr Pro Leu Asn Ala Pro Tyr Phe Thr Arg
        35                  40                  45

Ser Ile Gln Arg Thr His His Ser Ile Ser Val Leu Thr Leu Lys Phe
    50                  55                  60

Pro Ala Val Glu Ala Gly Leu Val Glu Gly Cys Glu Ser Val Asp Gln
65                  70                  75                  80

Ile Pro Ser Pro Asp Met Leu Pro Asn Phe Leu Lys Ala Thr Thr Met
                85                  90                  95

Leu Gln Asp Pro Leu Glu Arg Leu Leu Gln Asp Ser Arg Pro Asp Cys
            100                 105                 110

Leu Val Ala Asp Met Phe Phe Pro Trp Ala Thr His Val Ala Ala Lys
        115                 120                 125
```

```
Phe Asn Ile Pro Arg Leu Val Phe His Gly Thr Gly Phe Phe Thr Leu
    130                 135                 140

Cys Ala Ser Glu Asn Leu Arg Leu Tyr Met Pro Gln Ala Ser Val Ser
145                 150                 155                 160

Ser Asp Asp Glu Pro Phe Leu Val Pro Asn Leu Pro His Lys Ile Met
                165                 170                 175

Leu Thr Arg Ser Gln Leu Pro Glu Asn Glu Arg Cys Asp Thr Glu Thr
            180                 185                 190

Gly Leu Ser Thr Met Leu Lys Gln Val Lys Glu Thr Glu Leu Thr Ser
        195                 200                 205

Tyr Gly Val Ile Val Asn Ser Phe Tyr Glu Leu Glu Pro Asp Tyr Ala
    210                 215                 220

Asp Tyr Tyr Arg Asn Val Leu Gly Arg Arg Ala Trp His Ile Gly Pro
225                 230                 235                 240

Val Ser Leu Cys Asn Arg Glu Val Glu Asp Lys Ala Gln Arg Gly Lys
                245                 250                 255

Glu Ser Ala Ile Asp Glu Val Glu Cys Leu Lys Trp Leu Asn Ser Lys
            260                 265                 270

Lys Pro Asn Ser Val Ile Tyr Val Cys Phe Gly Ser Leu Gly Asp Phe
        275                 280                 285

Thr Ala Ser Gln Leu Phe Glu Leu Ala Met Gly Leu Glu Ala Ser Gly
    290                 295                 300

Gln Gln Phe Ile Trp Val Val Arg Lys Gly Lys Ile Glu Glu Asp Gly
305                 310                 315                 320

Asp Glu Lys Arg Leu Pro Glu Glu Phe Glu Glu Arg Met Lys Asp Lys
                325                 330                 335

Gly Leu Ile Ile Arg Gly Trp Ala Pro Gln Val Leu Ile Leu Asp His
            340                 345                 350

Glu Ser Ile Gly Gly Phe Val Thr His Cys Gly Trp Asn Ser Ile Leu
        355                 360                 365

Glu Gly Val Cys Ala Gly Val Pro Met Val Thr Trp Pro Arg Phe Ala
    370                 375                 380

Glu Gln Phe Tyr Asn Glu Lys Leu Val Thr Glu Val Leu Arg Ile Gly
385                 390                 395                 400

Val Gly Val Gly Ala Arg Gln Trp Gln Ile Gly Ala Gly Ser Asp Cys
                405                 410                 415

Ile Lys Gly Glu Thr Ile Ala Lys Ala Val Lys Arg Val Met Glu Ala
            420                 425                 430

Gly Glu Glu Ala Glu Gly Met Arg Thr Arg Ala Arg Ala Ala Lys Asp
        435                 440                 445

Met Ala Lys Lys Ala Val Glu Glu Gly Gly Ser Ser Tyr Ser Asp Leu
    450                 455                 460

Asn Ala Leu Ile Gln Glu Met Ser Ser
465                 470


<210> SEQ ID NO 5
<211> LENGTH: 1464
<212> TYPE: DNA
<213> ORGANISM: Humulus lupulus
<220> FEATURE:
<221> NAME/KEY: CDS
<222> LOCATION: (1)..(1461)

<400> SEQUENCE: 5

atg acc atg gaa act aag cct cac gca gta tgc atc cca tac cca gca       48
Met Thr Met Glu Thr Lys Pro His Ala Val Cys Ile Pro Tyr Pro Ala
```

-continued

```
1               5                   10                  15

cag ggc cat ata agc cct atg ctg aaa ctg gcc aag ctt ctc cac cag       96
Gln Gly His Ile Ser Pro Met Leu Lys Leu Ala Lys Leu Leu His Gln
            20                  25                  30

aga ggc ttc cac ata acc ttc gtc aac acc cac ttc aac cac aac cgt      144
Arg Gly Phe His Ile Thr Phe Val Asn Thr His Phe Asn His Asn Arg
        35                  40                  45

ctc ctc aaa tct aga ggc ccc aac tcc ctc gac ggt ttg cct gat ttt      192
Leu Leu Lys Ser Arg Gly Pro Asn Ser Leu Asp Gly Leu Pro Asp Phe
    50                  55                  60

cgc ttc gaa tca atc ccg gac ggc ctt cct ccg acg gag aac aaa gcc      240
Arg Phe Glu Ser Ile Pro Asp Gly Leu Pro Pro Thr Glu Asn Lys Ala
65                  70                  75                  80

gac gcc acg cag gac atc cca tcc ctg tgc gag tcc acc gaa aag acc      288
Asp Ala Thr Gln Asp Ile Pro Ser Leu Cys Glu Ser Thr Glu Lys Thr
                85                  90                  95

tgc cta gac ccc ttt cga aaa ctt ctc ttc cag cta aac gac gcc agc      336
Cys Leu Asp Pro Phe Arg Lys Leu Leu Phe Gln Leu Asn Asp Ala Ser
            100                 105                 110

tct agt agc ggc ggt gct gtt cca ccg gtg agc tgt gtc gtt tcg gat      384
Ser Ser Ser Gly Gly Ala Val Pro Pro Val Ser Cys Val Val Ser Asp
        115                 120                 125

gct tct atg ccg ttc aca ctt aaa gct ggt gaa gag ttt gga ata cct      432
Ala Ser Met Pro Phe Thr Leu Lys Ala Gly Glu Glu Phe Gly Ile Pro
    130                 135                 140

gtt gcg ctg ttt tgg act atc agt gct tgt ggc ttg ttg ggg tat acg      480
Val Ala Leu Phe Trp Thr Ile Ser Ala Cys Gly Leu Leu Gly Tyr Thr
145                 150                 155                 160

cag tat gag aat ctt gtc aat aaa gga ttt act ccc ttt aaa gat gag      528
Gln Tyr Glu Asn Leu Val Asn Lys Gly Phe Thr Pro Phe Lys Asp Glu
                165                 170                 175

agc tct ttt aca aat ggg tat ctg gat aca ttg ata gac tgg ata cca      576
Ser Ser Phe Thr Asn Gly Tyr Leu Asp Thr Leu Ile Asp Trp Ile Pro
            180                 185                 190

gcc gtg aat gat atc cga cta aaa gat ctt cca agc ttc ata cgc aca      624
Ala Val Asn Asp Ile Arg Leu Lys Asp Leu Pro Ser Phe Ile Arg Thr
        195                 200                 205

aca aat cca aat gat ttt atg gta aag tat gtt ata aga ttg att aaa      672
Thr Asn Pro Asn Asp Phe Met Val Lys Tyr Val Ile Arg Leu Ile Lys
    210                 215                 220

cta atg tca aca gga agt gcc att atc ttt aac act ttt gac tcg tta      720
Leu Met Ser Thr Gly Ser Ala Ile Ile Phe Asn Thr Phe Asp Ser Leu
225                 230                 235                 240

gag cgc aat gtc ttg gaa gct ctt tcg tcc atg atc cca tgt cca att      768
Glu Arg Asn Val Leu Glu Ala Leu Ser Ser Met Ile Pro Cys Pro Ile
                245                 250                 255

tac aca tta ggc ccc ctc cat cta ctt gtc aac aat act caa cca aaa      816
Tyr Thr Leu Gly Pro Leu His Leu Leu Val Asn Asn Thr Gln Pro Lys
            260                 265                 270

agt ttg tcc tcc att gca tcg aat tta tgg gta gaa gag cta gaa tgc      864
Ser Leu Ser Ser Ile Ala Ser Asn Leu Trp Val Glu Glu Leu Glu Cys
        275                 280                 285

ctc caa tgg ttg gat tca aag gac tcc aaa tca att gtt tat gtc aac      912
Leu Gln Trp Leu Asp Ser Lys Asp Ser Lys Ser Ile Val Tyr Val Asn
    290                 295                 300

ttt ggc agc atc act gcc gtg act ccg gaa caa ctt att gag ttc gct      960
Phe Gly Ser Ile Thr Ala Val Thr Pro Glu Gln Leu Ile Glu Phe Ala
305                 310                 315                 320

tgg ggt ttg gca aac agt aag aaa ccc ttt gtt tgg ata ata agg cca     1008
```

```
Trp Gly Leu Ala Asn Ser Lys Lys Pro Phe Val Trp Ile Ile Arg Pro
                325                 330                 335

gac ctc gtc gat gga gac tcg gcc att tta cct tca gag ttt gtg gaa     1056
Asp Leu Val Asp Gly Asp Ser Ala Ile Leu Pro Ser Glu Phe Val Glu
            340                 345                 350

gag aca agg gag aga agt ctg att tct agt tgg tgt cca caa gaa gag     1104
Glu Thr Arg Glu Arg Ser Leu Ile Ser Ser Trp Cys Pro Gln Glu Glu
        355                 360                 365

gtt ctt agc cac cct gcg att ggg ggt ttc cta acg cat tgt ggt tgg     1152
Val Leu Ser His Pro Ala Ile Gly Gly Phe Leu Thr His Cys Gly Trp
    370                 375                 380

aac tcg aca ctc gaa agc ttg agc gcg gga gtg cca atg att tgt tgg     1200
Asn Ser Thr Leu Glu Ser Leu Ser Ala Gly Val Pro Met Ile Cys Trp
385                 390                 395                 400

cct ttc ttc gcc gaa caa caa act aat tgt aag ttt ttg tgc aac tat     1248
Pro Phe Phe Ala Glu Gln Gln Thr Asn Cys Lys Phe Leu Cys Asn Tyr
                405                 410                 415

tgg ggg agt gga atg gaa ata aat ccc aat gtt aag aga gat gat gtg     1296
Trp Gly Ser Gly Met Glu Ile Asn Pro Asn Val Lys Arg Asp Asp Val
            420                 425                 430

gaa aag ctt gtg agg gag ttg atg gat gga gaa aaa gga aat gat atg     1344
Glu Lys Leu Val Arg Glu Leu Met Asp Gly Glu Lys Gly Asn Asp Met
        435                 440                 445

aga aac aag gcc atg gag tgg aag cac aaa gca cat gaa gcc act gag     1392
Arg Asn Lys Ala Met Glu Trp Lys His Lys Ala His Glu Ala Thr Glu
    450                 455                 460

ctt ggt ggc tct tct ttg gtg aat ctg gat aat atc atc agt aag gtt     1440
Leu Gly Gly Ser Ser Leu Val Asn Leu Asp Asn Ile Ile Ser Lys Val
465                 470                 475                 480

ttg gtg cca tca tca aaa cca taa                                     1464
Leu Val Pro Ser Ser Lys Pro
                485


<210> SEQ ID NO 6
<211> LENGTH: 487
<212> TYPE: PRT
<213> ORGANISM: Humulus lupulus

<400> SEQUENCE: 6

Met Thr Met Glu Thr Lys Pro His Ala Val Cys Ile Pro Tyr Pro Ala
1               5                   10                  15

Gln Gly His Ile Ser Pro Met Leu Lys Leu Ala Lys Leu Leu His Gln
            20                  25                  30

Arg Gly Phe His Ile Thr Phe Val Asn Thr His Phe Asn His Asn Arg
        35                  40                  45

Leu Leu Lys Ser Arg Gly Pro Asn Ser Leu Asp Gly Leu Pro Asp Phe
    50                  55                  60

Arg Phe Glu Ser Ile Pro Asp Gly Leu Pro Pro Thr Glu Asn Lys Ala
65                  70                  75                  80

Asp Ala Thr Gln Asp Ile Pro Ser Leu Cys Glu Ser Thr Glu Lys Thr
                85                  90                  95

Cys Leu Asp Pro Phe Arg Lys Leu Leu Phe Gln Leu Asn Asp Ala Ser
            100                 105                 110

Ser Ser Ser Gly Gly Ala Val Pro Pro Val Ser Cys Val Val Ser Asp
        115                 120                 125

Ala Ser Met Pro Phe Thr Leu Lys Ala Gly Glu Glu Phe Gly Ile Pro
    130                 135                 140

Val Ala Leu Phe Trp Thr Ile Ser Ala Cys Gly Leu Leu Gly Tyr Thr
```

```
145                 150                 155                 160

Gln Tyr Glu Asn Leu Val Asn Lys Gly Phe Thr Pro Phe Lys Asp Glu
                165                 170                 175

Ser Ser Phe Thr Asn Gly Tyr Leu Asp Thr Leu Ile Asp Trp Ile Pro
            180                 185                 190

Ala Val Asn Asp Ile Arg Leu Lys Asp Leu Pro Ser Phe Ile Arg Thr
        195                 200                 205

Thr Asn Pro Asn Asp Phe Met Val Lys Tyr Val Ile Arg Leu Ile Lys
    210                 215                 220

Leu Met Ser Thr Gly Ser Ala Ile Ile Phe Asn Thr Phe Asp Ser Leu
225                 230                 235                 240

Glu Arg Asn Val Leu Glu Ala Leu Ser Ser Met Ile Pro Cys Pro Ile
                245                 250                 255

Tyr Thr Leu Gly Pro Leu His Leu Leu Val Asn Asn Thr Gln Pro Lys
            260                 265                 270

Ser Leu Ser Ser Ile Ala Ser Asn Leu Trp Val Glu Glu Leu Glu Cys
        275                 280                 285

Leu Gln Trp Leu Asp Ser Lys Asp Ser Lys Ser Ile Val Tyr Val Asn
    290                 295                 300

Phe Gly Ser Ile Thr Ala Val Thr Pro Glu Gln Leu Ile Glu Phe Ala
305                 310                 315                 320

Trp Gly Leu Ala Asn Ser Lys Lys Pro Phe Val Trp Ile Ile Arg Pro
                325                 330                 335

Asp Leu Val Asp Gly Asp Ser Ala Ile Leu Pro Ser Glu Phe Val Glu
            340                 345                 350

Glu Thr Arg Glu Arg Ser Leu Ile Ser Ser Trp Cys Pro Gln Glu Glu
        355                 360                 365

Val Leu Ser His Pro Ala Ile Gly Gly Phe Leu Thr His Cys Gly Trp
    370                 375                 380

Asn Ser Thr Leu Glu Ser Leu Ser Ala Gly Val Pro Met Ile Cys Trp
385                 390                 395                 400

Pro Phe Phe Ala Glu Gln Gln Thr Asn Cys Lys Phe Leu Cys Asn Tyr
                405                 410                 415

Trp Gly Ser Gly Met Glu Ile Asn Pro Asn Val Lys Arg Asp Asp Val
            420                 425                 430

Glu Lys Leu Val Arg Glu Leu Met Asp Gly Glu Lys Gly Asn Asp Met
        435                 440                 445

Arg Asn Lys Ala Met Glu Trp Lys His Lys Ala His Glu Ala Thr Glu
    450                 455                 460

Leu Gly Gly Ser Ser Leu Val Asn Leu Asp Asn Ile Ile Ser Lys Val
465                 470                 475                 480

Leu Val Pro Ser Ser Lys Pro
                485


<210> SEQ ID NO 7
<211> LENGTH: 1464
<212> TYPE: DNA
<213> ORGANISM: Humulus lupulus
<220> FEATURE:
<221> NAME/KEY: CDS
<222> LOCATION: (1)..(1461)

<400> SEQUENCE: 7

atg acc atg gaa act aag cct cac gca gta tgc atc cca tac cca gca       48
Met Thr Met Glu Thr Lys Pro His Ala Val Cys Ile Pro Tyr Pro Ala
1               5                   10                  15
```

```
cag ggc cat ata aac cct atg ctg aaa ctg gcc aag ctt ctc cac cag        96
Gln Gly His Ile Asn Pro Met Leu Lys Leu Ala Lys Leu Leu His Gln
            20                  25                  30

aga ggc ttc cac ata acc ttc gtc aac acc cac ttc aac cac aac cgt       144
Arg Gly Phe His Ile Thr Phe Val Asn Thr His Phe Asn His Asn Arg
        35                  40                  45

ctc ctc aaa tct aga ggc ccc aac tcc ctc gat ggc ttg ccc gat ttt       192
Leu Leu Lys Ser Arg Gly Pro Asn Ser Leu Asp Gly Leu Pro Asp Phe
    50                  55                  60

cgc ttc gaa tca atc ccg gac ggc ctt cct ccg acg gag aac aaa gcc       240
Arg Phe Glu Ser Ile Pro Asp Gly Leu Pro Pro Thr Glu Asn Lys Ala
65                  70                  75                  80

gac gcc acg cag gac atc cca tcc ctg tgc gag tcc acc gaa aag acc       288
Asp Ala Thr Gln Asp Ile Pro Ser Leu Cys Glu Ser Thr Glu Lys Thr
                85                  90                  95

tgc cta gac ccc ttt cga aaa ctt ctc ttc cag cta aac gac gcc agc       336
Cys Leu Asp Pro Phe Arg Lys Leu Leu Phe Gln Leu Asn Asp Ala Ser
            100                 105                 110

tct agt agc ggc ggt gct gtt cca ccg gtg agc tgt gtc gtt tcg gat       384
Ser Ser Ser Gly Gly Ala Val Pro Pro Val Ser Cys Val Val Ser Asp
        115                 120                 125

cct gct atg ccg ttc aca ctt aca gct ggt gaa gag ttt gga ata cct       432
Pro Ala Met Pro Phe Thr Leu Thr Ala Gly Glu Glu Phe Gly Ile Pro
    130                 135                 140

gtt gcg ctg ttt tgg act atc agt gct tgt ggc ttg ttg ggg tat acg       480
Val Ala Leu Phe Trp Thr Ile Ser Ala Cys Gly Leu Leu Gly Tyr Thr
145                 150                 155                 160

cag tat gag aat ctt gtc aac aaa ggg ttt act ccc ttt aaa gat gag       528
Gln Tyr Glu Asn Leu Val Asn Lys Gly Phe Thr Pro Phe Lys Asp Glu
                165                 170                 175

agc tct ttt aca aat ggg tat ctg gat aca ttg ata gac tgg ata cca       576
Ser Ser Phe Thr Asn Gly Tyr Leu Asp Thr Leu Ile Asp Trp Ile Pro
            180                 185                 190

gcc gtg aat gat atc cga cta aaa gat ctt cca agc ttc ata cgc aca       624
Ala Val Asn Asp Ile Arg Leu Lys Asp Leu Pro Ser Phe Ile Arg Thr
        195                 200                 205

aca aat cca aat gaa ttt atg gta aag tat gtt ata aga ttg att aaa       672
Thr Asn Pro Asn Glu Phe Met Val Lys Tyr Val Ile Arg Leu Ile Lys
    210                 215                 220

cta act tca aca gga aat gcc atg atc ttt aac act ttt gac tcg tta       720
Leu Thr Ser Thr Gly Asn Ala Met Ile Phe Asn Thr Phe Asp Ser Leu
225                 230                 235                 240

gag cac aat gtc ttg gaa gct ctt tcg tcc atg ttc cca tgt cca att       768
Glu His Asn Val Leu Glu Ala Leu Ser Ser Met Phe Pro Cys Pro Ile
                245                 250                 255

tac aca tta ggc ccc ctc cat gta ctt gtc aac aag act caa tca aaa       816
Tyr Thr Leu Gly Pro Leu His Val Leu Val Asn Lys Thr Gln Ser Lys
            260                 265                 270

agt ttg tcc tcc att gca tcg aat tta tgg gta gaa gag cta gaa tgc       864
Ser Leu Ser Ser Ile Ala Ser Asn Leu Trp Val Glu Glu Leu Glu Cys
        275                 280                 285

ctc caa tgg ttg gat tca aag gat tcc aaa tca att gtt tat gtc aac       912
Leu Gln Trp Leu Asp Ser Lys Asp Ser Lys Ser Ile Val Tyr Val Asn
    290                 295                 300

ttt ggc agc atc act gcc gtg act ccg gaa caa ctt gtt gag ttc gct       960
Phe Gly Ser Ile Thr Ala Val Thr Pro Glu Gln Leu Val Glu Phe Ala
305                 310                 315                 320

tgg ggt ttg gca aac agt aag aaa ccc ttt gtt tgg ata ata agg cca      1008
Trp Gly Leu Ala Asn Ser Lys Lys Pro Phe Val Trp Ile Ile Arg Pro
```

```
                325                 330                 335

gac ctc gtc gat gga gac tcg gcc att tta cct tcg gag ttt gtg gaa      1056
Asp Leu Val Asp Gly Asp Ser Ala Ile Leu Pro Ser Glu Phe Val Glu
            340                 345                 350

gag aca agg gag aga agt ctg att tct agt tgg tgt cca caa gaa gag      1104
Glu Thr Arg Glu Arg Ser Leu Ile Ser Ser Trp Cys Pro Gln Glu Glu
        355                 360                 365

gtt ctt agc cac cct gcg att ggg ggt ttc cta acg cat tgt ggt tgg      1152
Val Leu Ser His Pro Ala Ile Gly Gly Phe Leu Thr His Cys Gly Trp
    370                 375                 380

aac tcg aca ctt gaa agc ttg agc gcg gga gtg cca acg att tgt tgg      1200
Asn Ser Thr Leu Glu Ser Leu Ser Ala Gly Val Pro Thr Ile Cys Trp
385                 390                 395                 400

cct ttc ttc gcc gag caa caa act aat tgt aag ttt ttg tgc gac tat      1248
Pro Phe Phe Ala Glu Gln Gln Thr Asn Cys Lys Phe Leu Cys Asp Tyr
                405                 410                 415

tgg ggg agt gga atg gaa ata aat ccc aat gtt aag aga gat gat gtt      1296
Trp Gly Ser Gly Met Glu Ile Asn Pro Asn Val Lys Arg Asp Asp Val
            420                 425                 430

gaa aag ctt gtg agg gag ttg atg gat gga gaa aaa gga aat gat atg      1344
Glu Lys Leu Val Arg Glu Leu Met Asp Gly Glu Lys Gly Asn Asp Met
        435                 440                 445

aga aac aag gcc atg gag tgg aag cac aaa gca cat gaa gcc acc gag      1392
Arg Asn Lys Ala Met Glu Trp Lys His Lys Ala His Glu Ala Thr Glu
    450                 455                 460

ctt ggt ggc tct tct ttg gtg aat ctg gat aat atc atc agt aag gtt      1440
Leu Gly Gly Ser Ser Leu Val Asn Leu Asp Asn Ile Ile Ser Lys Val
465                 470                 475                 480

ttg gtg cca tca tca aaa cca taa                                      1464
Leu Val Pro Ser Ser Lys Pro
                485


<210> SEQ ID NO 8
<211> LENGTH: 487
<212> TYPE: PRT
<213> ORGANISM: Humulus lupulus

<400> SEQUENCE: 8

Met Thr Met Glu Thr Lys Pro His Ala Val Cys Ile Pro Tyr Pro Ala
1               5                   10                  15

Gln Gly His Ile Asn Pro Met Leu Lys Leu Ala Lys Leu Leu His Gln
            20                  25                  30

Arg Gly Phe His Ile Thr Phe Val Asn Thr His Phe Asn His Asn Arg
        35                  40                  45

Leu Leu Lys Ser Arg Gly Pro Asn Ser Leu Asp Gly Leu Pro Asp Phe
    50                  55                  60

Arg Phe Glu Ser Ile Pro Asp Gly Leu Pro Pro Thr Glu Asn Lys Ala
65                  70                  75                  80

Asp Ala Thr Gln Asp Ile Pro Ser Leu Cys Glu Ser Thr Glu Lys Thr
                85                  90                  95

Cys Leu Asp Pro Phe Arg Lys Leu Leu Phe Gln Leu Asn Asp Ala Ser
            100                 105                 110

Ser Ser Ser Gly Gly Ala Val Pro Pro Val Ser Cys Val Val Ser Asp
        115                 120                 125

Pro Ala Met Pro Phe Thr Leu Thr Ala Gly Glu Glu Phe Gly Ile Pro
    130                 135                 140

Val Ala Leu Phe Trp Thr Ile Ser Ala Cys Gly Leu Leu Gly Tyr Thr
145                 150                 155                 160
```

```
Gln Tyr Glu Asn Leu Val Asn Lys Gly Phe Thr Pro Phe Lys Asp Glu
                165                 170                 175

Ser Ser Phe Thr Asn Gly Tyr Leu Asp Thr Leu Ile Asp Trp Ile Pro
            180                 185                 190

Ala Val Asn Asp Ile Arg Leu Lys Asp Leu Pro Ser Phe Ile Arg Thr
        195                 200                 205

Thr Asn Pro Asn Glu Phe Met Val Lys Tyr Val Ile Arg Leu Ile Lys
    210                 215                 220

Leu Thr Ser Thr Gly Asn Ala Met Ile Phe Asn Thr Phe Asp Ser Leu
225                 230                 235                 240

Glu His Asn Val Leu Glu Ala Leu Ser Ser Met Phe Pro Cys Pro Ile
                245                 250                 255

Tyr Thr Leu Gly Pro Leu His Val Leu Val Asn Lys Thr Gln Ser Lys
            260                 265                 270

Ser Leu Ser Ser Ile Ala Ser Asn Leu Trp Val Glu Glu Leu Glu Cys
        275                 280                 285

Leu Gln Trp Leu Asp Ser Lys Asp Ser Lys Ser Ile Val Tyr Val Asn
    290                 295                 300

Phe Gly Ser Ile Thr Ala Val Thr Pro Glu Gln Leu Val Glu Phe Ala
305                 310                 315                 320

Trp Gly Leu Ala Asn Ser Lys Lys Pro Phe Val Trp Ile Ile Arg Pro
                325                 330                 335

Asp Leu Val Asp Gly Asp Ser Ala Ile Leu Pro Ser Glu Phe Val Glu
            340                 345                 350

Glu Thr Arg Glu Arg Ser Leu Ile Ser Ser Trp Cys Pro Gln Glu Glu
        355                 360                 365

Val Leu Ser His Pro Ala Ile Gly Gly Phe Leu Thr His Cys Gly Trp
    370                 375                 380

Asn Ser Thr Leu Glu Ser Leu Ser Ala Gly Val Pro Thr Ile Cys Trp
385                 390                 395                 400

Pro Phe Phe Ala Glu Gln Gln Thr Asn Cys Lys Phe Leu Cys Asp Tyr
                405                 410                 415

Trp Gly Ser Gly Met Glu Ile Asn Pro Asn Val Lys Arg Asp Asp Val
            420                 425                 430

Glu Lys Leu Val Arg Glu Leu Met Asp Gly Glu Lys Gly Asn Asp Met
        435                 440                 445

Arg Asn Lys Ala Met Glu Trp Lys His Lys Ala His Glu Ala Thr Glu
    450                 455                 460

Leu Gly Gly Ser Ser Leu Val Asn Leu Asp Asn Ile Ile Ser Lys Val
465                 470                 475                 480

Leu Val Pro Ser Ser Lys Pro
                485
```

<210> SEQ ID NO 9
<211> LENGTH: 1464
<212> TYPE: DNA
<213> ORGANISM: Humulus lupulus
<220> FEATURE:
<221> NAME/KEY: CDS
<222> LOCATION: (1)..(1461)

<400> SEQUENCE: 9

```
atg acc atg gaa act aag cct cac gca gta tgc atc cca tac cca gca       48
Met Thr Met Glu Thr Lys Pro His Ala Val Cys Ile Pro Tyr Pro Ala
1               5                   10                  15
```

```
cag ggc cat ata aac cct atg ctg aaa ctg gcc aag ctt ctc cac cag       96
Gln Gly His Ile Asn Pro Met Leu Lys Leu Ala Lys Leu Leu His Gln
            20                  25                  30

aga ggc ttc cac ata acc ttc gtc aac acc cac ttc aac cac aac cgt      144
Arg Gly Phe His Ile Thr Phe Val Asn Thr His Phe Asn His Asn Arg
        35                  40                  45

atc ctc aaa tct aga ggc ccc aac tcc ctc gac ggc ttg ccc gat ttt      192
Ile Leu Lys Ser Arg Gly Pro Asn Ser Leu Asp Gly Leu Pro Asp Phe
    50                  55                  60

cgc ttc gaa tca atc ccg gac ggc ctt cct ccg acg gag aac aaa gcc      240
Arg Phe Glu Ser Ile Pro Asp Gly Leu Pro Pro Thr Glu Asn Lys Ala
65                  70                  75                  80

gac gcc acg cag gac atc cca tcc ctg tgc gag tcc acc gaa aag acc      288
Asp Ala Thr Gln Asp Ile Pro Ser Leu Cys Glu Ser Thr Glu Lys Thr
                85                  90                  95

tgc cta gac ccc ttt cga aaa ctt ctc ttc cag cta aac gac gcc agc      336
Cys Leu Asp Pro Phe Arg Lys Leu Leu Phe Gln Leu Asn Asp Ala Ser
            100                 105                 110

tct agt agc ggc ggt gct gtt cca ccg gtg agc tgt gtc gtt tcg gat      384
Ser Ser Ser Gly Gly Ala Val Pro Pro Val Ser Cys Val Val Ser Asp
        115                 120                 125

gct gct atg ccg ttc acc ctt aaa gct ggt gaa gag ttt gga ata cca      432
Ala Ala Met Pro Phe Thr Leu Lys Ala Gly Glu Glu Phe Gly Ile Pro
    130                 135                 140

gtt gcg ctg ttt tgg act atc agt gct tgc ggc ttg ttg ggg tat acg      480
Val Ala Leu Phe Trp Thr Ile Ser Ala Cys Gly Leu Leu Gly Tyr Thr
145                 150                 155                 160

cag tat gag aat ctt gtc aat aaa gga ttt act ccc ttt aaa gat gag      528
Gln Tyr Glu Asn Leu Val Asn Lys Gly Phe Thr Pro Phe Lys Asp Glu
                165                 170                 175

agc tct ttt aca aat ggg tat ctg gat aca ttg ata gat tgg ata cca      576
Ser Ser Phe Thr Asn Gly Tyr Leu Asp Thr Leu Ile Asp Trp Ile Pro
            180                 185                 190

gtc gtg aat gat atc cga cta aaa gat ctt cca agc ttc ata cgc aca      624
Val Val Asn Asp Ile Arg Leu Lys Asp Leu Pro Ser Phe Ile Arg Thr
        195                 200                 205

aca aat cca aat gaa ttt atg gta aag tat gtt ata aga ttg att aaa      672
Thr Asn Pro Asn Glu Phe Met Val Lys Tyr Val Ile Arg Leu Ile Lys
    210                 215                 220

cta act tca aca ggg agt gcc att atc ttt aac act ttt gac gca tta      720
Leu Thr Ser Thr Gly Ser Ala Ile Ile Phe Asn Thr Phe Asp Ala Leu
225                 230                 235                 240

gag cac aat gtc ttg gaa gct ctt tcg tcc atg ttc cca tgt cca att      768
Glu His Asn Val Leu Glu Ala Leu Ser Ser Met Phe Pro Cys Pro Ile
                245                 250                 255

tac aca tta ggt ccc ctc cat cta ctt gtc aac aag act caa cca aaa      816
Tyr Thr Leu Gly Pro Leu His Leu Leu Val Asn Lys Thr Gln Pro Lys
            260                 265                 270

agt ctg tcc tcc att gca tcg aat tta tgg gta gaa gag cta gaa tgc      864
Ser Leu Ser Ser Ile Ala Ser Asn Leu Trp Val Glu Glu Leu Glu Cys
        275                 280                 285

ctc caa tgg ttg gat tca aag gac tcc aaa tca att gtt tat gtc aac      912
Leu Gln Trp Leu Asp Ser Lys Asp Ser Lys Ser Ile Val Tyr Val Asn
    290                 295                 300

ttt ggc agc atc act gcc gtg act ccg gaa caa ctt att gag ttc gct      960
Phe Gly Ser Ile Thr Ala Val Thr Pro Glu Gln Leu Ile Glu Phe Ala
305                 310                 315                 320

tgg ggt ttg gca aac agt aag aaa ccc ttt gtt tgg ata ata agg cca     1008
Trp Gly Leu Ala Asn Ser Lys Lys Pro Phe Val Trp Ile Ile Arg Pro
                325                 330                 335
```

```
gac ctc gtc gat gga gac tcg gcc att tta cct tca gag ttt gtg gaa     1056
Asp Leu Val Asp Gly Asp Ser Ala Ile Leu Pro Ser Glu Phe Val Glu
            340                 345                 350

gag aca agg gag aga agt ctg att tct agt tgg tgt cca caa gaa gag     1104
Glu Thr Arg Glu Arg Ser Leu Ile Ser Ser Trp Cys Pro Gln Glu Glu
        355                 360                 365

gtt ctt agc cac cct gcg att ggg ggt ttc cta acg cat tgt ggt tgg     1152
Val Leu Ser His Pro Ala Ile Gly Gly Phe Leu Thr His Cys Gly Trp
    370                 375                 380

aac tcg aca ctc gaa agc ttg agc gct gga gtg cca atg att tgt tgg     1200
Asn Ser Thr Leu Glu Ser Leu Ser Ala Gly Val Pro Met Ile Cys Trp
385                 390                 395                 400

ccc ttc ttt gcc gag caa caa act aat tgt aag ttt ttg tgc gac tat     1248
Pro Phe Phe Ala Glu Gln Gln Thr Asn Cys Lys Phe Leu Cys Asp Tyr
                405                 410                 415

tgg ggg agt gga atg gaa ata aat ccc aat gtt aag aga gat gat gtg     1296
Trp Gly Ser Gly Met Glu Ile Asn Pro Asn Val Lys Arg Asp Asp Val
            420                 425                 430

gaa aag ctt gtg agg gaa ttg atg gat gga gaa aaa gga aat gat atg     1344
Glu Lys Leu Val Arg Glu Leu Met Asp Gly Glu Lys Gly Asn Asp Met
        435                 440                 445

aga aac aag gcc atg gag tgg aag cac aaa gca cat gaa gcc acc gag     1392
Arg Asn Lys Ala Met Glu Trp Lys His Lys Ala His Glu Ala Thr Glu
    450                 455                 460

ctt ggt ggc tct tct ttg gtg aat ctg gat aat atc atc agt aag gtt     1440
Leu Gly Gly Ser Ser Leu Val Asn Leu Asp Asn Ile Ile Ser Lys Val
465                 470                 475                 480

ttg gtg cca tca tca aaa cca taa                                     1464
Leu Val Pro Ser Ser Lys Pro
                485


<210> SEQ ID NO 10
<211> LENGTH: 487
<212> TYPE: PRT
<213> ORGANISM: Humulus lupulus

<400> SEQUENCE: 10

Met Thr Met Glu Thr Lys Pro His Ala Val Cys Ile Pro Tyr Pro Ala
1               5                   10                  15

Gln Gly His Ile Asn Pro Met Leu Lys Leu Ala Lys Leu Leu His Gln
            20                  25                  30

Arg Gly Phe His Ile Thr Phe Val Asn Thr His Phe Asn His Asn Arg
        35                  40                  45

Ile Leu Lys Ser Arg Gly Pro Asn Ser Leu Asp Gly Leu Pro Asp Phe
    50                  55                  60

Arg Phe Glu Ser Ile Pro Asp Gly Leu Pro Pro Thr Glu Asn Lys Ala
65                  70                  75                  80

Asp Ala Thr Gln Asp Ile Pro Ser Leu Cys Glu Ser Thr Glu Lys Thr
                85                  90                  95

Cys Leu Asp Pro Phe Arg Lys Leu Leu Phe Gln Leu Asn Asp Ala Ser
            100                 105                 110

Ser Ser Ser Gly Gly Ala Val Pro Pro Val Ser Cys Val Val Ser Asp
        115                 120                 125

Ala Ala Met Pro Phe Thr Leu Lys Ala Gly Glu Glu Phe Gly Ile Pro
    130                 135                 140

Val Ala Leu Phe Trp Thr Ile Ser Ala Cys Gly Leu Leu Gly Tyr Thr
145                 150                 155                 160
```

```
Gln Tyr Glu Asn Leu Val Asn Lys Gly Phe Thr Pro Phe Lys Asp Glu
                165                 170                 175

Ser Ser Phe Thr Asn Gly Tyr Leu Asp Thr Leu Ile Asp Trp Ile Pro
            180                 185                 190

Val Val Asn Asp Ile Arg Leu Lys Asp Leu Pro Ser Phe Ile Arg Thr
        195                 200                 205

Thr Asn Pro Asn Glu Phe Met Val Lys Tyr Val Ile Arg Leu Ile Lys
    210                 215                 220

Leu Thr Ser Thr Gly Ser Ala Ile Ile Phe Asn Thr Phe Asp Ala Leu
225                 230                 235                 240

Glu His Asn Val Leu Glu Ala Leu Ser Ser Met Phe Pro Cys Pro Ile
                245                 250                 255

Tyr Thr Leu Gly Pro Leu His Leu Leu Val Asn Lys Thr Gln Pro Lys
            260                 265                 270

Ser Leu Ser Ser Ile Ala Ser Asn Leu Trp Val Glu Glu Leu Glu Cys
        275                 280                 285

Leu Gln Trp Leu Asp Ser Lys Asp Ser Lys Ser Ile Val Tyr Val Asn
    290                 295                 300

Phe Gly Ser Ile Thr Ala Val Thr Pro Glu Gln Leu Ile Glu Phe Ala
305                 310                 315                 320

Trp Gly Leu Ala Asn Ser Lys Lys Pro Phe Val Trp Ile Ile Arg Pro
                325                 330                 335

Asp Leu Val Asp Gly Asp Ser Ala Ile Leu Pro Ser Glu Phe Val Glu
            340                 345                 350

Glu Thr Arg Glu Arg Ser Leu Ile Ser Ser Trp Cys Pro Gln Glu Glu
        355                 360                 365

Val Leu Ser His Pro Ala Ile Gly Gly Phe Leu Thr His Cys Gly Trp
    370                 375                 380

Asn Ser Thr Leu Glu Ser Leu Ser Ala Gly Val Pro Met Ile Cys Trp
385                 390                 395                 400

Pro Phe Phe Ala Glu Gln Gln Thr Asn Cys Lys Phe Leu Cys Asp Tyr
                405                 410                 415

Trp Gly Ser Gly Met Glu Ile Asn Pro Asn Val Lys Arg Asp Asp Val
            420                 425                 430

Glu Lys Leu Val Arg Glu Leu Met Asp Gly Glu Lys Gly Asn Asp Met
        435                 440                 445

Arg Asn Lys Ala Met Glu Trp Lys His Lys Ala His Glu Ala Thr Glu
    450                 455                 460

Leu Gly Gly Ser Ser Leu Val Asn Leu Asp Asn Ile Ile Ser Lys Val
465                 470                 475                 480

Leu Val Pro Ser Ser Lys Pro
                485


<210> SEQ ID NO 11
<211> LENGTH: 1455
<212> TYPE: DNA
<213> ORGANISM: Humulus lupulus
<220> FEATURE:
<221> NAME/KEY: CDS
<222> LOCATION: (1)..(1452)

<400> SEQUENCE: 11

atg ggt tca atc agc gaa atg atg aag ccg cat gca gtg tgt gtt cca       48
Met Gly Ser Ile Ser Glu Met Met Lys Pro His Ala Val Cys Val Pro
1               5                   10                  15

ttt cca gca caa gga cat gtt aac ccc atg atg caa cta gcc aag ctt       96
```

```
Phe Pro Ala Gln Gly His Val Asn Pro Met Met Gln Leu Ala Lys Leu
            20                  25                  30

cta cac tca aga ggc ttc cat ata act tat gtc aac act gag ttc aac      144
Leu His Ser Arg Gly Phe His Ile Thr Tyr Val Asn Thr Glu Phe Asn
        35                  40                  45

cac agg cgc tta atc aga tcg aga ggt ccg gac tct gtg aaa ggc cta      192
His Arg Arg Leu Ile Arg Ser Arg Gly Pro Asp Ser Val Lys Gly Leu
    50                  55                  60

cct gac ttt cag ttt gag acc ata cca gat ggt ttg cca cca tca gat      240
Pro Asp Phe Gln Phe Glu Thr Ile Pro Asp Gly Leu Pro Pro Ser Asp
65                  70                  75                  80

cgt gat gca acc caa gaa gtt cca cct tta tgt gac gca act aga aag      288
Arg Asp Ala Thr Gln Glu Val Pro Pro Leu Cys Asp Ala Thr Arg Lys
                85                  90                  95

aac tgt tta ggt cca ttt aaa gag ctt tta cat aag ctc aga agt tgt      336
Asn Cys Leu Gly Pro Phe Lys Glu Leu Leu His Lys Leu Arg Ser Cys
            100                 105                 110

tct gaa gtg cct cca gtc act tgc atc att act gat ggg atc atg acc      384
Ser Glu Val Pro Pro Val Thr Cys Ile Ile Thr Asp Gly Ile Met Thr
        115                 120                 125

ttt ggt ata aaa gct gct agg gag ttt ggg att cca gag gtt gtt ttt      432
Phe Gly Ile Lys Ala Ala Arg Glu Phe Gly Ile Pro Glu Val Val Phe
    130                 135                 140

tgg act gct tct gct tgt agc ttc atg ggg tac ctc caa tac gat gaa      480
Trp Thr Ala Ser Ala Cys Ser Phe Met Gly Tyr Leu Gln Tyr Asp Glu
145                 150                 155                 160

ctt gtc aga aga ggc atc gtt cct ttc aaa gac gaa agc ttc atg cta      528
Leu Val Arg Arg Gly Ile Val Pro Phe Lys Asp Glu Ser Phe Met Leu
                165                 170                 175

gat ggt act ctt gac aca cca ata gac tgg att cca ggc ata aga gat      576
Asp Gly Thr Leu Asp Thr Pro Ile Asp Trp Ile Pro Gly Ile Arg Asp
            180                 185                 190

gta aga ctg agg gac ttg cca agc ttc ttg aga gtg aca tca acc gac      624
Val Arg Leu Arg Asp Leu Pro Ser Phe Leu Arg Val Thr Ser Thr Asp
        195                 200                 205

gac ata atg ttc gat ttt ctc gga tca caa gca aag aac tgc ctg act      672
Asp Ile Met Phe Asp Phe Leu Gly Ser Gln Ala Lys Asn Cys Leu Thr
    210                 215                 220

tct tcc gct ata atc ttc aac aca ttc cga gag cta gag cta gaa gta      720
Ser Ser Ala Ile Ile Phe Asn Thr Phe Arg Glu Leu Glu Leu Glu Val
225                 230                 235                 240

cta gat tcg atc tcg gac atg tac cca aac atc tac act ata gga cca      768
Leu Asp Ser Ile Ser Asp Met Tyr Pro Asn Ile Tyr Thr Ile Gly Pro
                245                 250                 255

ctt cct atg ctc aac cgt cat ctt cca gct gaa agt caa gtc aag tcc      816
Leu Pro Met Leu Asn Arg His Leu Pro Ala Glu Ser Gln Val Lys Ser
            260                 265                 270

atg agt aca agc tta tgg aaa gaa gac tca aca tgt ttc caa tgg ctc      864
Met Ser Thr Ser Leu Trp Lys Glu Asp Ser Thr Cys Phe Gln Trp Leu
        275                 280                 285

cac aaa aga gaa ccc aat tca gtt gtg tac gtg aac tat gga agc atc      912
His Lys Arg Glu Pro Asn Ser Val Val Tyr Val Asn Tyr Gly Ser Ile
    290                 295                 300

aca aca atg act gaa gac aat ttc aga gaa ttt gct tgg gga ctt gct      960
Thr Thr Met Thr Glu Asp Asn Phe Arg Glu Phe Ala Trp Gly Leu Ala
305                 310                 315                 320

aat agt aaa cac tcg ttt gtg tgg ata gtt agg cct gat gtt ata atg     1008
Asn Ser Lys His Ser Phe Val Trp Ile Val Arg Pro Asp Val Ile Met
                325                 330                 335
```

```
ggt tct aat tca gcc act gtt ttg ccc gaa gaa ttt ttc gag gag att      1056
Gly Ser Asn Ser Ala Thr Val Leu Pro Glu Glu Phe Phe Glu Glu Ile
            340                 345                 350

aag gat aga ggg ctg ctg gca aac tgg tgc caa caa aag gaa gtt ttg      1104
Lys Asp Arg Gly Leu Leu Ala Asn Trp Cys Gln Gln Lys Glu Val Leu
        355                 360                 365

gaa cat tct tca gtt ggg gtt ttc tta acc cat tgt ggt tgg aac tcc      1152
Glu His Ser Ser Val Gly Val Phe Leu Thr His Cys Gly Trp Asn Ser
    370                 375                 380

act gtg gag act gtg tgt gct ggt gtg cct gtg att tgc tgg cct ttc      1200
Thr Val Glu Thr Val Cys Ala Gly Val Pro Val Ile Cys Trp Pro Phe
385                 390                 395                 400

ttt gct gat cag caa acc aac tgt cat ttt gct tgt aaa aca ttg ggt      1248
Phe Ala Asp Gln Gln Thr Asn Cys His Phe Ala Cys Lys Thr Leu Gly
                405                 410                 415

att ggg gtg gaa att agc cct gat gtc aaa aga gag gaa gtc act ggg      1296
Ile Gly Val Glu Ile Ser Pro Asp Val Lys Arg Glu Glu Val Thr Gly
            420                 425                 430

ctt gtg aag gag atg atg gaa ggg gag aag ggg gag aaa atg agg gaa      1344
Leu Val Lys Glu Met Met Glu Gly Glu Lys Gly Glu Lys Met Arg Glu
        435                 440                 445

aag gct tcg tat tgg aag aag aaa gca gct gaa act act gac att ggt      1392
Lys Ala Ser Tyr Trp Lys Lys Lys Ala Ala Glu Thr Thr Asp Ile Gly
    450                 455                 460

ggt gat tct tat cat gat ttt gac aaa ttg att aag agt ctc ggc ttt      1440
Gly Asp Ser Tyr His Asp Phe Asp Lys Leu Ile Lys Ser Leu Gly Phe
465                 470                 475                 480

gat ggt agg gac taa                                                  1455
Asp Gly Arg Asp

<210> SEQ ID NO 12
<211> LENGTH: 484
<212> TYPE: PRT
<213> ORGANISM: Humulus lupulus

<400> SEQUENCE: 12

Met Gly Ser Ile Ser Glu Met Met Lys Pro His Ala Val Cys Val Pro
1               5                   10                  15

Phe Pro Ala Gln Gly His Val Asn Pro Met Met Gln Leu Ala Lys Leu
            20                  25                  30

Leu His Ser Arg Gly Phe His Ile Thr Tyr Val Asn Thr Glu Phe Asn
        35                  40                  45

His Arg Arg Leu Ile Arg Ser Arg Gly Pro Asp Ser Val Lys Gly Leu
    50                  55                  60

Pro Asp Phe Gln Phe Glu Thr Ile Pro Asp Gly Leu Pro Pro Ser Asp
65                  70                  75                  80

Arg Asp Ala Thr Gln Glu Val Pro Pro Leu Cys Asp Ala Thr Arg Lys
                85                  90                  95

Asn Cys Leu Gly Pro Phe Lys Glu Leu Leu His Lys Leu Arg Ser Cys
            100                 105                 110

Ser Glu Val Pro Pro Val Thr Cys Ile Ile Thr Asp Gly Ile Met Thr
        115                 120                 125

Phe Gly Ile Lys Ala Ala Arg Glu Phe Gly Ile Pro Glu Val Val Phe
    130                 135                 140

Trp Thr Ala Ser Ala Cys Ser Phe Met Gly Tyr Leu Gln Tyr Asp Glu
145                 150                 155                 160

Leu Val Arg Arg Gly Ile Val Pro Phe Lys Asp Glu Ser Phe Met Leu
                165                 170                 175
```

```
Asp Gly Thr Leu Asp Thr Pro Ile Asp Trp Ile Pro Gly Ile Arg Asp
            180                 185                 190

Val Arg Leu Arg Asp Leu Pro Ser Phe Leu Arg Val Thr Ser Thr Asp
        195                 200                 205

Asp Ile Met Phe Asp Phe Leu Gly Ser Gln Ala Lys Asn Cys Leu Thr
    210                 215                 220

Ser Ser Ala Ile Ile Phe Asn Thr Phe Arg Glu Leu Glu Leu Glu Val
225                 230                 235                 240

Leu Asp Ser Ile Ser Asp Met Tyr Pro Asn Ile Tyr Thr Ile Gly Pro
                245                 250                 255

Leu Pro Met Leu Asn Arg His Leu Pro Ala Glu Ser Gln Val Lys Ser
            260                 265                 270

Met Ser Thr Ser Leu Trp Lys Glu Asp Ser Thr Cys Phe Gln Trp Leu
        275                 280                 285

His Lys Arg Glu Pro Asn Ser Val Val Tyr Val Asn Tyr Gly Ser Ile
    290                 295                 300

Thr Thr Met Thr Glu Asp Asn Phe Arg Glu Phe Ala Trp Gly Leu Ala
305                 310                 315                 320

Asn Ser Lys His Ser Phe Val Trp Ile Val Arg Pro Asp Val Ile Met
                325                 330                 335

Gly Ser Asn Ser Ala Thr Val Leu Pro Glu Glu Phe Phe Glu Glu Ile
            340                 345                 350

Lys Asp Arg Gly Leu Leu Ala Asn Trp Cys Gln Gln Lys Glu Val Leu
        355                 360                 365

Glu His Ser Ser Val Gly Val Phe Leu Thr His Cys Gly Trp Asn Ser
    370                 375                 380

Thr Val Glu Thr Val Cys Ala Gly Val Pro Val Ile Cys Trp Pro Phe
385                 390                 395                 400

Phe Ala Asp Gln Gln Thr Asn Cys His Phe Ala Cys Lys Thr Leu Gly
                405                 410                 415

Ile Gly Val Glu Ile Ser Pro Asp Val Lys Arg Glu Glu Val Thr Gly
            420                 425                 430

Leu Val Lys Glu Met Met Glu Gly Glu Lys Gly Glu Lys Met Arg Glu
        435                 440                 445

Lys Ala Ser Tyr Trp Lys Lys Lys Ala Ala Glu Thr Thr Asp Ile Gly
    450                 455                 460

Gly Asp Ser Tyr His Asp Phe Asp Lys Leu Ile Lys Ser Leu Gly Phe
465                 470                 475                 480

Asp Gly Arg Asp


<210> SEQ ID NO 13
<211> LENGTH: 1446
<212> TYPE: DNA
<213> ORGANISM: Stevia rebaudiana
<220> FEATURE:
<221> NAME/KEY: CDS
<222> LOCATION: (1)..(1443)

<400> SEQUENCE: 13

atg gat gca atg gct aca act gag aag aaa cca cac gtc atc ttc ata       48
Met Asp Ala Met Ala Thr Thr Glu Lys Lys Pro His Val Ile Phe Ile
1               5                   10                  15

cca ttt cca gca caa agc cac att aaa gcc atg ctc aaa cta gca caa       96
Pro Phe Pro Ala Gln Ser His Ile Lys Ala Met Leu Lys Leu Ala Gln
            20                  25                  30

ctt ctc cac cac aaa gga ctc cag ata acc ttc gtc aac acc gac ttc      144
```

```
Leu Leu His His Lys Gly Leu Gln Ile Thr Phe Val Asn Thr Asp Phe
        35                  40                  45

atc cac aac cag ttt ctt gaa tca tcg ggc cca cat tgt ttg gac ggt      192
Ile His Asn Gln Phe Leu Glu Ser Ser Gly Pro His Cys Leu Asp Gly
    50                  55                  60

tca ccg ggt ttc cgg ttc gaa acc atc ccg gat ggt gtt tct cac agt      240
Ser Pro Gly Phe Arg Phe Glu Thr Ile Pro Asp Gly Val Ser His Ser
65                  70                  75                  80

ccg gaa gcg agc atc cca atc aga gaa tca ctc ttg aga tcc att gaa      288
Pro Glu Ala Ser Ile Pro Ile Arg Glu Ser Leu Leu Arg Ser Ile Glu
                85                  90                  95

acc aac ttc ttg gat cgt ttc att gat ctt gta acc aaa ctt ccg gat      336
Thr Asn Phe Leu Asp Arg Phe Ile Asp Leu Val Thr Lys Leu Pro Asp
            100                 105                 110

cct ccg act tgt att atc tca gat ggg ttc ttg tcg gtt ttc aca att      384
Pro Pro Thr Cys Ile Ile Ser Asp Gly Phe Leu Ser Val Phe Thr Ile
        115                 120                 125

gac gct gca aaa aag ctt gga att ccg gtc atg atg tat tgg aca ctt      432
Asp Ala Ala Lys Lys Leu Gly Ile Pro Val Met Met Tyr Trp Thr Leu
    130                 135                 140

gct gcc tgt ggg ttc atg ggt ttt tac cat att cat tct ctc att gag      480
Ala Ala Cys Gly Phe Met Gly Phe Tyr His Ile His Ser Leu Ile Glu
145                 150                 155                 160

aaa gga ttt gca cca ctt aaa gat gca agt tac ttg aca aat ggg tat      528
Lys Gly Phe Ala Pro Leu Lys Asp Ala Ser Tyr Leu Thr Asn Gly Tyr
                165                 170                 175

ttg gac acc gtc att gat tgg gtt ccg gga atg gaa ggc atc cgt ctc      576
Leu Asp Thr Val Ile Asp Trp Val Pro Gly Met Glu Gly Ile Arg Leu
            180                 185                 190

aag gat ttc ccg ctg gac tgg agc act gac ctc aat gac aaa gtt ttg      624
Lys Asp Phe Pro Leu Asp Trp Ser Thr Asp Leu Asn Asp Lys Val Leu
        195                 200                 205

atg ttc act aca gaa gct cct caa agg tca cac aag gtt tca cat cat      672
Met Phe Thr Thr Glu Ala Pro Gln Arg Ser His Lys Val Ser His His
    210                 215                 220

att ttc cac acg ttc gat gag ttg gag cct agt att ata aaa act ttg      720
Ile Phe His Thr Phe Asp Glu Leu Glu Pro Ser Ile Ile Lys Thr Leu
225                 230                 235                 240

tca ttg agg tat aat cac att tac acc atc ggc cca ctg caa tta ctt      768
Ser Leu Arg Tyr Asn His Ile Tyr Thr Ile Gly Pro Leu Gln Leu Leu
                245                 250                 255

ctt gat caa ata ccc gaa gag aaa aag caa act gga att acg agt ctc      816
Leu Asp Gln Ile Pro Glu Glu Lys Lys Gln Thr Gly Ile Thr Ser Leu
            260                 265                 270

cat gga tac agt tta gta aaa gaa gaa cca gag tgt ttc cag tgg ctt      864
His Gly Tyr Ser Leu Val Lys Glu Glu Pro Glu Cys Phe Gln Trp Leu
        275                 280                 285

cag tct aaa gaa cca aat tcc gtc gtt tat gta aat ttt gga agt act      912
Gln Ser Lys Glu Pro Asn Ser Val Val Tyr Val Asn Phe Gly Ser Thr
    290                 295                 300

aca gta atg tct tta gaa gac atg acg gaa ttt ggt tgg gga ctt gct      960
Thr Val Met Ser Leu Glu Asp Met Thr Glu Phe Gly Trp Gly Leu Ala
305                 310                 315                 320

aat agc aac cat tat ttc ctt tgg atc atc cga tca aac ttg gtg ata     1008
Asn Ser Asn His Tyr Phe Leu Trp Ile Ile Arg Ser Asn Leu Val Ile
                325                 330                 335

ggg gaa aat gca gtt ttg ccc cct gaa ctt gag gaa cat ata aag aaa     1056
Gly Glu Asn Ala Val Leu Pro Pro Glu Leu Glu Glu His Ile Lys Lys
            340                 345                 350
```

```
aga ggc ttt att gct agc tgg tgt tca caa gaa aag gtc ttg aag cac      1104
Arg Gly Phe Ile Ala Ser Trp Cys Ser Gln Glu Lys Val Leu Lys His
        355                 360                 365

cct tcg gtt gga ggg ttc ttg act cat tgt ggg tgg gga tcg acc atc      1152
Pro Ser Val Gly Gly Phe Leu Thr His Cys Gly Trp Gly Ser Thr Ile
    370                 375                 380

gag agc ttg tct gct ggg gtg cca atg ata tgc tgg cct tat tcg tgg      1200
Glu Ser Leu Ser Ala Gly Val Pro Met Ile Cys Trp Pro Tyr Ser Trp
385                 390                 395                 400

gac cag ctg acc aac tgt agg tat ata tgc aaa gaa tgg gag gtt ggg      1248
Asp Gln Leu Thr Asn Cys Arg Tyr Ile Cys Lys Glu Trp Glu Val Gly
                405                 410                 415

ctc gag atg gga acc aaa gtg aaa cga gat gaa gtc aag agg ctt gta      1296
Leu Glu Met Gly Thr Lys Val Lys Arg Asp Glu Val Lys Arg Leu Val
            420                 425                 430

caa gag ttg atg gga gaa gga ggt cac aaa atg agg aac aag gct aaa      1344
Gln Glu Leu Met Gly Glu Gly Gly His Lys Met Arg Asn Lys Ala Lys
        435                 440                 445

gat tgg aaa gaa aag gct cgc att gca ata gct cct aac ggt tca tct      1392
Asp Trp Lys Glu Lys Ala Arg Ile Ala Ile Ala Pro Asn Gly Ser Ser
    450                 455                 460

tct ttg aac ata gac aaa atg gtc aag gaa atc acc gtg cta gca aga      1440
Ser Leu Asn Ile Asp Lys Met Val Lys Glu Ile Thr Val Leu Ala Arg
465                 470                 475                 480

aac tag                                                              1446
Asn

<210> SEQ ID NO 14
<211> LENGTH: 481
<212> TYPE: PRT
<213> ORGANISM: Stevia rebaudiana

<400> SEQUENCE: 14

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ser Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
    130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
```

```
        195                 200                 205

Met Phe Thr Thr Glu Ala Pro Gln Arg Ser His Lys Val Ser His His
    210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
        275                 280                 285

Gln Ser Lys Glu Pro Asn Ser Val Val Tyr Val Asn Phe Gly Ser Thr
    290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
            340                 345                 350

Arg Gly Phe Ile Ala Ser Trp Cys Ser Gln Glu Lys Val Leu Lys His
        355                 360                 365

Pro Ser Val Gly Gly Phe Leu Thr His Cys Gly Trp Gly Ser Thr Ile
    370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
            420                 425                 430

Gln Glu Leu Met Gly Glu Gly Gly His Lys Met Arg Asn Lys Ala Lys
        435                 440                 445

Asp Trp Lys Glu Lys Ala Arg Ile Ala Ile Ala Pro Asn Gly Ser Ser
    450                 455                 460

Ser Leu Asn Ile Asp Lys Met Val Lys Glu Ile Thr Val Leu Ala Arg
465                 470                 475                 480

Asn


<210> SEQ ID NO 15
<211> LENGTH: 1440
<212> TYPE: DNA
<213> ORGANISM: Stevia rebaudiana
<220> FEATURE:
<221> NAME/KEY: CDS
<222> LOCATION: (1)..(1437)

<400> SEQUENCE: 15

atg gct tca ata gca gaa atg caa aag cca cat gcc ata tgc atc ccc       48
Met Ala Ser Ile Ala Glu Met Gln Lys Pro His Ala Ile Cys Ile Pro
1               5                   10                  15

tac cca gcc caa ggc cac atc aac ccc atg atg caa ttt gct aag ctc       96
Tyr Pro Ala Gln Gly His Ile Asn Pro Met Met Gln Phe Ala Lys Leu
            20                  25                  30

ctt cac ttc aaa ggc ttt cac ata tct ttt gtc aat aac cac tac aac      144
Leu His Phe Lys Gly Phe His Ile Ser Phe Val Asn Asn His Tyr Asn
        35                  40                  45

cat aag cgg ttg cag cgg tcc cgc ggt ctg tcc gcc ctc gaa ggt cta      192
```

-continued

```
His Lys Arg Leu Gln Arg Ser Arg Gly Leu Ser Ala Leu Glu Gly Leu
    50                  55                  60

cct gat ttt cat ttc tac tcg att ccc gat ggc ctt ccg cct tca aat      240
Pro Asp Phe His Phe Tyr Ser Ile Pro Asp Gly Leu Pro Pro Ser Asn
65                  70                  75                  80

gct gag gcc acc cag tcg atc ccc ggg cta tgt gag tcg att cct aag      288
Ala Glu Ala Thr Gln Ser Ile Pro Gly Leu Cys Glu Ser Ile Pro Lys
                85                  90                  95

cac agt ttg gaa cca ttt tgt gaa ttg atc gct acg cta aat ggt tcg      336
His Ser Leu Glu Pro Phe Cys Glu Leu Ile Ala Thr Leu Asn Gly Ser
            100                 105                 110

gac gtg cca cct gta agc tgt ata atc tct gac ggg gtc atg agc ttt      384
Asp Val Pro Pro Val Ser Cys Ile Ile Ser Asp Gly Val Met Ser Phe
        115                 120                 125

acg ctt caa gct gcc gag agg ttc ggg ttg ccg gaa gtt ttg ttc tgg      432
Thr Leu Gln Ala Ala Glu Arg Phe Gly Leu Pro Glu Val Leu Phe Trp
    130                 135                 140

acc cca agt gct tgt ggg ttt ttg gct tac act cac tat cga gat ctt      480
Thr Pro Ser Ala Cys Gly Phe Leu Ala Tyr Thr His Tyr Arg Asp Leu
145                 150                 155                 160

gtg gat aag gag tat att ccc ctc aaa gac acg aac gac ttg aca aat      528
Val Asp Lys Glu Tyr Ile Pro Leu Lys Asp Thr Asn Asp Leu Thr Asn
                165                 170                 175

ggg tat tta gaa aca agc ttg gat tgg att cct ggg atg aaa aac atc      576
Gly Tyr Leu Glu Thr Ser Leu Asp Trp Ile Pro Gly Met Lys Asn Ile
            180                 185                 190

cga tta aaa gat ttc cca tcc ttt att cga acc aca gac ata aat gat      624
Arg Leu Lys Asp Phe Pro Ser Phe Ile Arg Thr Thr Asp Ile Asn Asp
        195                 200                 205

att atg ctc aat tat ttc ttg att gaa acc gaa gcg atc cca aaa ggc      672
Ile Met Leu Asn Tyr Phe Leu Ile Glu Thr Glu Ala Ile Pro Lys Gly
    210                 215                 220

gta gcg atc att ctt aac aca ttt gac gcg tta gaa aaa gat agt att      720
Val Ala Ile Ile Leu Asn Thr Phe Asp Ala Leu Glu Lys Asp Ser Ile
225                 230                 235                 240

acg cct gta ctt gct cta aat cca caa ata tac acc att ggt cca tta      768
Thr Pro Val Leu Ala Leu Asn Pro Gln Ile Tyr Thr Ile Gly Pro Leu
                245                 250                 255

cac atg atg caa caa tat gtc gat cat gat gag aga ctc aaa cac att      816
His Met Met Gln Gln Tyr Val Asp His Asp Glu Arg Leu Lys His Ile
            260                 265                 270

ggg tcc aac ctt tgg aag gaa gat gtg agc tgc atc aat tgg ctt gac      864
Gly Ser Asn Leu Trp Lys Glu Asp Val Ser Cys Ile Asn Trp Leu Asp
        275                 280                 285

acc aaa aag cct aat tcg gtt gtt tat gtg aac ttt gga agt att acg      912
Thr Lys Lys Pro Asn Ser Val Val Tyr Val Asn Phe Gly Ser Ile Thr
    290                 295                 300

gtt atg acg aaa gaa caa ctg atc gag ttt ggg tgg gga ctg gct aat      960
Val Met Thr Lys Glu Gln Leu Ile Glu Phe Gly Trp Gly Leu Ala Asn
305                 310                 315                 320

agc aag aag gat ttc ttg tgg ata acg agg cct gat att gtt gga ggc     1008
Ser Lys Lys Asp Phe Leu Trp Ile Thr Arg Pro Asp Ile Val Gly Gly
                325                 330                 335

aat gaa gcc atg ata cca gca gag ttc ata gag gag acc aaa gaa agg     1056
Asn Glu Ala Met Ile Pro Ala Glu Phe Ile Glu Glu Thr Lys Glu Arg
            340                 345                 350

ggc atg gtt act agc tgg tgc tct cag gaa gag gtt tta aaa cat cca     1104
Gly Met Val Thr Ser Trp Cys Ser Gln Glu Glu Val Leu Lys His Pro
        355                 360                 365
```

```
tca atc ggg gta ttc ttg act cat agt gga tgg aac tcg acg att gag      1152
Ser Ile Gly Val Phe Leu Thr His Ser Gly Trp Asn Ser Thr Ile Glu
    370                 375                 380

agt att agc aac ggt gtt ccc atg att tgt tgg cct ttt ttt gca gag      1200
Ser Ile Ser Asn Gly Val Pro Met Ile Cys Trp Pro Phe Phe Ala Glu
385                 390                 395                 400

caa caa aca aat tgt cgg tat tgt tgt gtt gaa tgg gaa att gga ttg      1248
Gln Gln Thr Asn Cys Arg Tyr Cys Cys Val Glu Trp Glu Ile Gly Leu
                405                 410                 415

gaa att gat aca gat gtg aag aga gag gag gta gag gct caa gtg agg      1296
Glu Ile Asp Thr Asp Val Lys Arg Glu Glu Val Glu Ala Gln Val Arg
            420                 425                 430

gag atg atg gat ggg tcg aaa ggg aag atg atg aaa aac aag gct ttg      1344
Glu Met Met Asp Gly Ser Lys Gly Lys Met Met Lys Asn Lys Ala Leu
        435                 440                 445

gaa tgg aag aag aag gct gaa gaa gcg gta tcc att ggt gga tct tct      1392
Glu Trp Lys Lys Lys Ala Glu Glu Ala Val Ser Ile Gly Gly Ser Ser
    450                 455                 460

tat ctc aac ttt gaa aaa tta gtt acc gat gtt ctt tta aga aag tga      1440
Tyr Leu Asn Phe Glu Lys Leu Val Thr Asp Val Leu Leu Arg Lys
465                 470                 475


<210> SEQ ID NO 16
<211> LENGTH: 479
<212> TYPE: PRT
<213> ORGANISM: Stevia rebaudiana

<400> SEQUENCE: 16

Met Ala Ser Ile Ala Glu Met Gln Lys Pro His Ala Ile Cys Ile Pro
1               5                   10                  15

Tyr Pro Ala Gln Gly His Ile Asn Pro Met Met Gln Phe Ala Lys Leu
            20                  25                  30

Leu His Phe Lys Gly Phe His Ile Ser Phe Val Asn Asn His Tyr Asn
        35                  40                  45

His Lys Arg Leu Gln Arg Ser Arg Gly Leu Ser Ala Leu Glu Gly Leu
    50                  55                  60

Pro Asp Phe His Phe Tyr Ser Ile Pro Asp Gly Leu Pro Pro Ser Asn
65                  70                  75                  80

Ala Glu Ala Thr Gln Ser Ile Pro Gly Leu Cys Glu Ser Ile Pro Lys
                85                  90                  95

His Ser Leu Glu Pro Phe Cys Glu Leu Ile Ala Thr Leu Asn Gly Ser
            100                 105                 110

Asp Val Pro Pro Val Ser Cys Ile Ile Ser Asp Gly Val Met Ser Phe
        115                 120                 125

Thr Leu Gln Ala Ala Glu Arg Phe Gly Leu Pro Glu Val Leu Phe Trp
    130                 135                 140

Thr Pro Ser Ala Cys Gly Phe Leu Ala Tyr Thr His Tyr Arg Asp Leu
145                 150                 155                 160

Val Asp Lys Glu Tyr Ile Pro Leu Lys Asp Thr Asn Asp Leu Thr Asn
                165                 170                 175

Gly Tyr Leu Glu Thr Ser Leu Asp Trp Ile Pro Gly Met Lys Asn Ile
            180                 185                 190

Arg Leu Lys Asp Phe Pro Ser Phe Ile Arg Thr Thr Asp Ile Asn Asp
        195                 200                 205

Ile Met Leu Asn Tyr Phe Leu Ile Glu Thr Glu Ala Ile Pro Lys Gly
    210                 215                 220

Val Ala Ile Ile Leu Asn Thr Phe Asp Ala Leu Glu Lys Asp Ser Ile
```

```
225                 230                 235                 240

Thr Pro Val Leu Ala Leu Asn Pro Gln Ile Tyr Thr Ile Gly Pro Leu
                245                 250                 255

His Met Met Gln Gln Tyr Val Asp His Asp Glu Arg Leu Lys His Ile
            260                 265                 270

Gly Ser Asn Leu Trp Lys Glu Asp Val Ser Cys Ile Asn Trp Leu Asp
        275                 280                 285

Thr Lys Lys Pro Asn Ser Val Val Tyr Val Asn Phe Gly Ser Ile Thr
    290                 295                 300

Val Met Thr Lys Glu Gln Leu Ile Glu Phe Gly Trp Gly Leu Ala Asn
305                 310                 315                 320

Ser Lys Lys Asp Phe Leu Trp Ile Thr Arg Pro Asp Ile Val Gly Gly
                325                 330                 335

Asn Glu Ala Met Ile Pro Ala Glu Phe Ile Glu Glu Thr Lys Glu Arg
            340                 345                 350

Gly Met Val Thr Ser Trp Cys Ser Gln Glu Glu Val Leu Lys His Pro
        355                 360                 365

Ser Ile Gly Val Phe Leu Thr His Ser Gly Trp Asn Ser Thr Ile Glu
    370                 375                 380

Ser Ile Ser Asn Gly Val Pro Met Ile Cys Trp Pro Phe Phe Ala Glu
385                 390                 395                 400

Gln Gln Thr Asn Cys Arg Tyr Cys Cys Val Glu Trp Glu Ile Gly Leu
                405                 410                 415

Glu Ile Asp Thr Asp Val Lys Arg Glu Glu Val Glu Ala Gln Val Arg
            420                 425                 430

Glu Met Met Asp Gly Ser Lys Gly Lys Met Met Lys Asn Lys Ala Leu
        435                 440                 445

Glu Trp Lys Lys Lys Ala Glu Glu Ala Val Ser Ile Gly Gly Ser Ser
    450                 455                 460

Tyr Leu Asn Phe Glu Lys Leu Val Thr Asp Val Leu Leu Arg Lys
465                 470                 475


<210> SEQ ID NO 17
<211> LENGTH: 1452
<212> TYPE: DNA
<213> ORGANISM: Stevia rebaudiana
<220> FEATURE:
<221> NAME/KEY: CDS
<222> LOCATION: (1)..(1449)

<400> SEQUENCE: 17

atg gat caa atg gca aaa att gac gag aag aaa cct cat gtg gtg ttc       48
Met Asp Gln Met Ala Lys Ile Asp Glu Lys Lys Pro His Val Val Phe
1               5                   10                  15

ata ccg ttt ccc gca caa agt cat atc aag tgc atg ctc aaa cta gcc       96
Ile Pro Phe Pro Ala Gln Ser His Ile Lys Cys Met Leu Lys Leu Ala
            20                  25                  30

aga atc cta cac caa aag ggc ctc tat ata acc ttc atc aac acc gac      144
Arg Ile Leu His Gln Lys Gly Leu Tyr Ile Thr Phe Ile Asn Thr Asp
        35                  40                  45

acg aac cat gag cga ctc gta gcc tct ggt ggg acc caa tgg ctc gag      192
Thr Asn His Glu Arg Leu Val Ala Ser Gly Gly Thr Gln Trp Leu Glu
    50                  55                  60

aat gct cct ggt ttt tgg ttc aaa acg gtt ccc gat ggg ttc ggt tct      240
Asn Ala Pro Gly Phe Trp Phe Lys Thr Val Pro Asp Gly Phe Gly Ser
65                  70                  75                  80

gct aaa gac gac ggt gtc aag cct act gac gct tta cga gaa ctc atg      288
```

-continued

```
Ala Lys Asp Asp Gly Val Lys Pro Thr Asp Ala Leu Arg Glu Leu Met
                85                  90                  95

gat tac ctt aaa acc aat ttc ttt gat ttg ttt ctt gat ctt gta ctc      336
Asp Tyr Leu Lys Thr Asn Phe Phe Asp Leu Phe Leu Asp Leu Val Leu
            100                 105                 110

aag ctt gaa gtc ccg gct aca tgc atc att tgt gat ggt tgc atg act      384
Lys Leu Glu Val Pro Ala Thr Cys Ile Ile Cys Asp Gly Cys Met Thr
        115                 120                 125

ttc gcg aac aca att cgc gcg gct gaa aaa ctt aat att ccg gtt att      432
Phe Ala Asn Thr Ile Arg Ala Ala Glu Lys Leu Asn Ile Pro Val Ile
    130                 135                 140

ctt ttc tgg acc atg gct gct tgt gga ttc atg gcg ttt tac cag gct      480
Leu Phe Trp Thr Met Ala Ala Cys Gly Phe Met Ala Phe Tyr Gln Ala
145                 150                 155                 160

aaa gtt tta aag gag aaa gaa att gtc cca gtt aaa gat gaa act tat      528
Lys Val Leu Lys Glu Lys Glu Ile Val Pro Val Lys Asp Glu Thr Tyr
                165                 170                 175

ttg acc aat gga tat ctt gac atg gaa ata gac tgg att cct gga atg      576
Leu Thr Asn Gly Tyr Leu Asp Met Glu Ile Asp Trp Ile Pro Gly Met
            180                 185                 190

aaa aga atc cgt ttg agg gat cta ccc gag ttc ata cta gcc aca aaa      624
Lys Arg Ile Arg Leu Arg Asp Leu Pro Glu Phe Ile Leu Ala Thr Lys
        195                 200                 205

caa aat tat ttt gct ttt gag ttt tta ttt gaa acc gct caa ttg gcc      672
Gln Asn Tyr Phe Ala Phe Glu Phe Leu Phe Glu Thr Ala Gln Leu Ala
    210                 215                 220

gat aag gtc tcg cat atg atc atc cat acc ttt gag gaa ctt gag gct      720
Asp Lys Val Ser His Met Ile Ile His Thr Phe Glu Glu Leu Glu Ala
225                 230                 235                 240

agt ctt gtg agt gag att aaa tcc ata ttt cct aat gtt tac acc att      768
Ser Leu Val Ser Glu Ile Lys Ser Ile Phe Pro Asn Val Tyr Thr Ile
                245                 250                 255

ggg cct ctc cag ttg ctt ttg aac aaa att aca caa aaa gaa act aac      816
Gly Pro Leu Gln Leu Leu Leu Asn Lys Ile Thr Gln Lys Glu Thr Asn
            260                 265                 270

aac gat agc tat agc tta tgg aag gaa gaa ccc gag tgt gtc gag tgg      864
Asn Asp Ser Tyr Ser Leu Trp Lys Glu Glu Pro Glu Cys Val Glu Trp
        275                 280                 285

cta aac tca aag gaa ccg aat tct gtg gtg tat gtc aac ttt gga agt      912
Leu Asn Ser Lys Glu Pro Asn Ser Val Val Tyr Val Asn Phe Gly Ser
    290                 295                 300

ttg gcg gtg atg tct tta caa gat ttg gta gaa ttt ggg tgg gga ctt      960
Leu Ala Val Met Ser Leu Gln Asp Leu Val Glu Phe Gly Trp Gly Leu
305                 310                 315                 320

gtt aat agc aac cat tat ttt ctt tgg att ata cgc gct aat ttg att     1008
Val Asn Ser Asn His Tyr Phe Leu Trp Ile Ile Arg Ala Asn Leu Ile
                325                 330                 335

gat ggg aag ccg gcg gtt atg cct caa gaa ctc aag gag gcg atg aac     1056
Asp Gly Lys Pro Ala Val Met Pro Gln Glu Leu Lys Glu Ala Met Asn
            340                 345                 350

gag aaa ggg ttt gta gga agc tgg tgt tca cag gaa gag gtg ttg aac     1104
Glu Lys Gly Phe Val Gly Ser Trp Cys Ser Gln Glu Glu Val Leu Asn
        355                 360                 365

cac cct gcg gtt ggt ggg ttc ttg aca cac tgt ggt tgg ggt tcg ata     1152
His Pro Ala Val Gly Gly Phe Leu Thr His Cys Gly Trp Gly Ser Ile
    370                 375                 380

att gaa agc ttg tca gct gga gtg cca atg ctg ggt tgg ccg tca ata     1200
Ile Glu Ser Leu Ser Ala Gly Val Pro Met Leu Gly Trp Pro Ser Ile
385                 390                 395                 400
```

```
ggt gac caa cgc gct aat tgt aga caa atg tgt aag gaa tgg gag gtt      1248
Gly Asp Gln Arg Ala Asn Cys Arg Gln Met Cys Lys Glu Trp Glu Val
                405                 410                 415

ggt atg gag att ggg aag aat gtg aaa agg gat gaa gtt gag aag ctt      1296
Gly Met Glu Ile Gly Lys Asn Val Lys Arg Asp Glu Val Glu Lys Leu
            420                 425                 430

gtg agg atg tta atg gag gga ttg gag ggt gaa cga atg agg aag aaa      1344
Val Arg Met Leu Met Glu Gly Leu Glu Gly Glu Arg Met Arg Lys Lys
        435                 440                 445

gct ttg gag tgg aag aaa agt gca aca ctg gcg aca tgt tgt aat ggg      1392
Ala Leu Glu Trp Lys Lys Ser Ala Thr Leu Ala Thr Cys Cys Asn Gly
    450                 455                 460

tca tct agt ttg gat gta gag aaa ctt gct aat gaa atc aag aag tta      1440
Ser Ser Ser Leu Asp Val Glu Lys Leu Ala Asn Glu Ile Lys Lys Leu
465                 470                 475                 480

tca aga aac tag                                                      1452
Ser Arg Asn

<210> SEQ ID NO 18
<211> LENGTH: 483
<212> TYPE: PRT
<213> ORGANISM: Stevia rebaudiana

<400> SEQUENCE: 18

Met Asp Gln Met Ala Lys Ile Asp Glu Lys Lys Pro His Val Val Phe
1               5                   10                  15

Ile Pro Phe Pro Ala Gln Ser His Ile Lys Cys Met Leu Lys Leu Ala
            20                  25                  30

Arg Ile Leu His Gln Lys Gly Leu Tyr Ile Thr Phe Ile Asn Thr Asp
        35                  40                  45

Thr Asn His Glu Arg Leu Val Ala Ser Gly Gly Thr Gln Trp Leu Glu
    50                  55                  60

Asn Ala Pro Gly Phe Trp Phe Lys Thr Val Pro Asp Gly Phe Gly Ser
65                  70                  75                  80

Ala Lys Asp Asp Gly Val Lys Pro Thr Asp Ala Leu Arg Glu Leu Met
                85                  90                  95

Asp Tyr Leu Lys Thr Asn Phe Phe Asp Leu Phe Leu Asp Leu Val Leu
            100                 105                 110

Lys Leu Glu Val Pro Ala Thr Cys Ile Ile Cys Asp Gly Cys Met Thr
        115                 120                 125

Phe Ala Asn Thr Ile Arg Ala Ala Glu Lys Leu Asn Ile Pro Val Ile
    130                 135                 140

Leu Phe Trp Thr Met Ala Ala Cys Gly Phe Met Ala Phe Tyr Gln Ala
145                 150                 155                 160

Lys Val Leu Lys Glu Lys Glu Ile Val Pro Val Lys Asp Glu Thr Tyr
                165                 170                 175

Leu Thr Asn Gly Tyr Leu Asp Met Glu Ile Asp Trp Ile Pro Gly Met
            180                 185                 190

Lys Arg Ile Arg Leu Arg Asp Leu Pro Glu Phe Ile Leu Ala Thr Lys
        195                 200                 205

Gln Asn Tyr Phe Ala Phe Glu Phe Leu Phe Glu Thr Ala Gln Leu Ala
    210                 215                 220

Asp Lys Val Ser His Met Ile Ile His Thr Phe Glu Glu Leu Glu Ala
225                 230                 235                 240

Ser Leu Val Ser Glu Ile Lys Ser Ile Phe Pro Asn Val Tyr Thr Ile
                245                 250                 255

Gly Pro Leu Gln Leu Leu Leu Asn Lys Ile Thr Gln Lys Glu Thr Asn
```

```
            260                 265                 270

Asn Asp Ser Tyr Ser Leu Trp Lys Glu Glu Pro Glu Cys Val Glu Trp
        275                 280                 285

Leu Asn Ser Lys Glu Pro Asn Ser Val Val Tyr Val Asn Phe Gly Ser
    290                 295                 300

Leu Ala Val Met Ser Leu Gln Asp Leu Val Glu Phe Gly Trp Gly Leu
305                 310                 315                 320

Val Asn Ser Asn His Tyr Phe Leu Trp Ile Ile Arg Ala Asn Leu Ile
                325                 330                 335

Asp Gly Lys Pro Ala Val Met Pro Gln Glu Leu Lys Glu Ala Met Asn
            340                 345                 350

Glu Lys Gly Phe Val Gly Ser Trp Cys Ser Gln Glu Glu Val Leu Asn
        355                 360                 365

His Pro Ala Val Gly Gly Phe Leu Thr His Cys Gly Trp Gly Ser Ile
    370                 375                 380

Ile Glu Ser Leu Ser Ala Gly Val Pro Met Leu Gly Trp Pro Ser Ile
385                 390                 395                 400

Gly Asp Gln Arg Ala Asn Cys Arg Gln Met Cys Lys Glu Trp Glu Val
                405                 410                 415

Gly Met Glu Ile Gly Lys Asn Val Lys Arg Asp Glu Val Glu Lys Leu
            420                 425                 430

Val Arg Met Leu Met Glu Gly Leu Glu Gly Glu Arg Met Arg Lys Lys
        435                 440                 445

Ala Leu Glu Trp Lys Lys Ser Ala Thr Leu Ala Thr Cys Cys Asn Gly
    450                 455                 460

Ser Ser Ser Leu Asp Val Glu Lys Leu Ala Asn Glu Ile Lys Lys Leu
465                 470                 475                 480

Ser Arg Asn


<210> SEQ ID NO 19
<211> LENGTH: 1449
<212> TYPE: DNA
<213> ORGANISM: Vitis sp.
<220> FEATURE:
<221> NAME/KEY: CDS
<222> LOCATION: (1)..(1446)

<400> SEQUENCE: 19

atg ggt tca gtc aca gct tct gat aaa cct cat gtt gtg ttg atc cca       48
Met Gly Ser Val Thr Ala Ser Asp Lys Pro His Val Val Leu Ile Pro
1               5                   10                  15

tac cca gct caa ggc cat gtg aac cca atg ctg aag cta gca aaa ctg       96
Tyr Pro Ala Gln Gly His Val Asn Pro Met Leu Lys Leu Ala Lys Leu
            20                  25                  30

ctt cac aac aaa ggc ttt ttc gtc tct ttt gtc aac acc gag tac aac      144
Leu His Asn Lys Gly Phe Phe Val Ser Phe Val Asn Thr Glu Tyr Asn
        35                  40                  45

cat aag cgt ttg ctc agg tcc aga ggc ccc aac tct ctt gat ggc ctc      192
His Lys Arg Leu Leu Arg Ser Arg Gly Pro Asn Ser Leu Asp Gly Leu
    50                  55                  60

tct gac ttt cgc ttt gag acc atc cca gat ggc ctc cca cca agt gat      240
Ser Asp Phe Arg Phe Glu Thr Ile Pro Asp Gly Leu Pro Pro Ser Asp
65                  70                  75                  80

gct gac gcc acc caa gac atc ccc tct ctc tgt gtt tcc acc acc aag      288
Ala Asp Ala Thr Gln Asp Ile Pro Ser Leu Cys Val Ser Thr Thr Lys
                85                  90                  95

aac tgc ttg gct ccc ttt tgc gcc ctc atc act aag ctc aat gat cct      336
```

```
Asn Cys Leu Ala Pro Phe Cys Ala Leu Ile Thr Lys Leu Asn Asp Pro
            100                 105                 110

tcc tac tct cct ggc cca cct gtg agc tgt att gtg tct gat ggt gtc      384
Ser Tyr Ser Pro Gly Pro Pro Val Ser Cys Ile Val Ser Asp Gly Val
        115                 120                 125

atg tcc ttc act ctt gat gct gcc gag aag ttc gga gtg cct gaa gtg      432
Met Ser Phe Thr Leu Asp Ala Ala Glu Lys Phe Gly Val Pro Glu Val
    130                 135                 140

gtg ttt tgg acg aca agc gca tgt ggc ttt ctc ggg tat agg cac tac      480
Val Phe Trp Thr Thr Ser Ala Cys Gly Phe Leu Gly Tyr Arg His Tyr
145                 150                 155                 160

aga aac ctt att cga aga ggc ctc ata cca ctc caa gat gaa agc tgt      528
Arg Asn Leu Ile Arg Arg Gly Leu Ile Pro Leu Gln Asp Glu Ser Cys
                165                 170                 175

tta agc aat ggg tac tta gac acc gtt gtt gac ttc gtt cct gga aag      576
Leu Ser Asn Gly Tyr Leu Asp Thr Val Val Asp Phe Val Pro Gly Lys
            180                 185                 190

aag aaa acc atc cgt ctg aga gac ttt cca act ttc ctc aga acg aca      624
Lys Lys Thr Ile Arg Leu Arg Asp Phe Pro Thr Phe Leu Arg Thr Thr
        195                 200                 205

gac ctg aac gat atc atg ctc aac ttc gtg agg gtg gag gca gag aga      672
Asp Leu Asn Asp Ile Met Leu Asn Phe Val Arg Val Glu Ala Glu Arg
    210                 215                 220

gct tcc aga gct tct gct gtc att ttg aac act ttc gat gct ttg gaa      720
Ala Ser Arg Ala Ser Ala Val Ile Leu Asn Thr Phe Asp Ala Leu Glu
225                 230                 235                 240

aaa gat gtt ctg gat gct ctc tca gcc act ctt cct cct gtt tac tcc      768
Lys Asp Val Leu Asp Ala Leu Ser Ala Thr Leu Pro Pro Val Tyr Ser
                245                 250                 255

atc ggt cct ctt cag cat ttg gtt gat cag att tca gac gat aga ttg      816
Ile Gly Pro Leu Gln His Leu Val Asp Gln Ile Ser Asp Asp Arg Leu
            260                 265                 270

aaa tcc atg ggc tca aat cta tgg aaa gaa caa aca gat tgt ctc caa      864
Lys Ser Met Gly Ser Asn Leu Trp Lys Glu Gln Thr Asp Cys Leu Gln
        275                 280                 285

tgg ctc gac tcc aaa gaa ccc aac tca gtc gtg tac gtg aat ttc gga      912
Trp Leu Asp Ser Lys Glu Pro Asn Ser Val Val Tyr Val Asn Phe Gly
    290                 295                 300

agc atc aca gtg atg aca tcc caa cag ctc aca gag ttc gct tgg gga      960
Ser Ile Thr Val Met Thr Ser Gln Gln Leu Thr Glu Phe Ala Trp Gly
305                 310                 315                 320

cta gct aac agc aac aag ccc ttc cta tgg atc ata agg cct gat ctg     1008
Leu Ala Asn Ser Asn Lys Pro Phe Leu Trp Ile Ile Arg Pro Asp Leu
                325                 330                 335

gtg gtg ggt gac tca gcg ctt ctg cca ccg gag ttt gtg acg gaa acg     1056
Val Val Gly Asp Ser Ala Leu Leu Pro Pro Glu Phe Val Thr Glu Thr
            340                 345                 350

aaa gat aga ggc atg tta gca agc tgg tgc ccg caa gag caa gtg ctg     1104
Lys Asp Arg Gly Met Leu Ala Ser Trp Cys Pro Gln Glu Gln Val Leu
        355                 360                 365

aag cac ccg gct ata gga ggg ttc tta aca cat agc ggc tgg aac tcc     1152
Lys His Pro Ala Ile Gly Gly Phe Leu Thr His Ser Gly Trp Asn Ser
    370                 375                 380

aca agc gag agc ata tgt ggg gga gtg cca ctg att tgt tgg cca ttc     1200
Thr Ser Glu Ser Ile Cys Gly Gly Val Pro Leu Ile Cys Trp Pro Phe
385                 390                 395                 400

ttc gcc gag caa cag acc aac tgt cgc tat agt tgc agt gaa tgg ggg     1248
Phe Ala Glu Gln Gln Thr Asn Cys Arg Tyr Ser Cys Ser Glu Trp Gly
                405                 410                 415
```

```
ata ggg atg gag att gat aat aat gtg aag agg gtg gaa gtg gaa aag      1296
Ile Gly Met Glu Ile Asp Asn Asn Val Lys Arg Val Glu Val Glu Lys
            420                 425                 430

ctt gtg aga gag ctg atg gat ggg gag aag ggg aag gag atg aag aag      1344
Leu Val Arg Glu Leu Met Asp Gly Glu Lys Gly Lys Glu Met Lys Lys
        435                 440                 445

aag gtg atg gaa tgg aag aag ttg gca gaa gag gcc act agg cct gga      1392
Lys Val Met Glu Trp Lys Lys Leu Ala Glu Glu Ala Thr Arg Pro Gly
    450                 455                 460

ggg tca tcg tac gac aac ttc aac aaa ctg ctg cgt aat gtg ttg tca      1440
Gly Ser Ser Tyr Asp Asn Phe Asn Lys Leu Leu Arg Asn Val Leu Ser
465                 470                 475                 480

aag aag tag                                                           1449
Lys Lys


<210> SEQ ID NO 20
<211> LENGTH: 482
<212> TYPE: PRT
<213> ORGANISM: Vitis sp.

<400> SEQUENCE: 20

Met Gly Ser Val Thr Ala Ser Asp Lys Pro His Val Val Leu Ile Pro
1               5                   10                  15

Tyr Pro Ala Gln Gly His Val Asn Pro Met Leu Lys Leu Ala Lys Leu
            20                  25                  30

Leu His Asn Lys Gly Phe Phe Val Ser Phe Val Asn Thr Glu Tyr Asn
        35                  40                  45

His Lys Arg Leu Leu Arg Ser Arg Gly Pro Asn Ser Leu Asp Gly Leu
    50                  55                  60

Ser Asp Phe Arg Phe Glu Thr Ile Pro Asp Gly Leu Pro Pro Ser Asp
65                  70                  75                  80

Ala Asp Ala Thr Gln Asp Ile Pro Ser Leu Cys Val Ser Thr Thr Lys
                85                  90                  95

Asn Cys Leu Ala Pro Phe Cys Ala Leu Ile Thr Lys Leu Asn Asp Pro
            100                 105                 110

Ser Tyr Ser Pro Gly Pro Pro Val Ser Cys Ile Val Ser Asp Gly Val
        115                 120                 125

Met Ser Phe Thr Leu Asp Ala Ala Glu Lys Phe Gly Val Pro Glu Val
    130                 135                 140

Val Phe Trp Thr Thr Ser Ala Cys Gly Phe Leu Gly Tyr Arg His Tyr
145                 150                 155                 160

Arg Asn Leu Ile Arg Arg Gly Leu Ile Pro Leu Gln Asp Glu Ser Cys
                165                 170                 175

Leu Ser Asn Gly Tyr Leu Asp Thr Val Val Asp Phe Val Pro Gly Lys
            180                 185                 190

Lys Lys Thr Ile Arg Leu Arg Asp Phe Pro Thr Phe Leu Arg Thr Thr
        195                 200                 205

Asp Leu Asn Asp Ile Met Leu Asn Phe Val Arg Val Glu Ala Glu Arg
    210                 215                 220

Ala Ser Arg Ala Ser Ala Val Ile Leu Asn Thr Phe Asp Ala Leu Glu
225                 230                 235                 240

Lys Asp Val Leu Asp Ala Leu Ser Ala Thr Leu Pro Pro Val Tyr Ser
                245                 250                 255

Ile Gly Pro Leu Gln His Leu Val Asp Gln Ile Ser Asp Asp Arg Leu
            260                 265                 270

Lys Ser Met Gly Ser Asn Leu Trp Lys Glu Gln Thr Asp Cys Leu Gln
```

```
        275                 280                 285

Trp Leu Asp Ser Lys Glu Pro Asn Ser Val Val Tyr Val Asn Phe Gly
    290                 295                 300

Ser Ile Thr Val Met Thr Ser Gln Gln Leu Thr Glu Phe Ala Trp Gly
305                 310                 315                 320

Leu Ala Asn Ser Asn Lys Pro Phe Leu Trp Ile Ile Arg Pro Asp Leu
                325                 330                 335

Val Val Gly Asp Ser Ala Leu Leu Pro Pro Glu Phe Val Thr Glu Thr
            340                 345                 350

Lys Asp Arg Gly Met Leu Ala Ser Trp Cys Pro Gln Glu Gln Val Leu
        355                 360                 365

Lys His Pro Ala Ile Gly Gly Phe Leu Thr His Ser Gly Trp Asn Ser
    370                 375                 380

Thr Ser Glu Ser Ile Cys Gly Gly Val Pro Leu Ile Cys Trp Pro Phe
385                 390                 395                 400

Phe Ala Glu Gln Gln Thr Asn Cys Arg Tyr Ser Cys Ser Glu Trp Gly
                405                 410                 415

Ile Gly Met Glu Ile Asp Asn Asn Val Lys Arg Val Glu Val Glu Lys
            420                 425                 430

Leu Val Arg Glu Leu Met Asp Gly Glu Lys Gly Lys Glu Met Lys Lys
        435                 440                 445

Lys Val Met Glu Trp Lys Lys Leu Ala Glu Glu Ala Thr Arg Pro Gly
    450                 455                 460

Gly Ser Ser Tyr Asp Asn Phe Asn Lys Leu Leu Arg Asn Val Leu Ser
465                 470                 475                 480

Lys Lys


<210> SEQ ID NO 21
<211> LENGTH: 1422
<212> TYPE: DNA
<213> ORGANISM: Vitis sp.
<220> FEATURE:
<221> NAME/KEY: CDS
<222> LOCATION: (1)..(1419)

<400> SEQUENCE: 21

atg ggt tcc atg gag aag cct cat gca gtt tgc att cca tac cct gct       48
Met Gly Ser Met Glu Lys Pro His Ala Val Cys Ile Pro Tyr Pro Ala
1               5                   10                  15

cag ggg cac atc aat cct atg cta aaa cta gca aag ctc ctc cat ttc       96
Gln Gly His Ile Asn Pro Met Leu Lys Leu Ala Lys Leu Leu His Phe
            20                  25                  30

aga ggc ttt cgt atc acc ttc gtc aac aca gag ttc aac cac aca cgc      144
Arg Gly Phe Arg Ile Thr Phe Val Asn Thr Glu Phe Asn His Thr Arg
        35                  40                  45

tta ctc aag gcc cag ggc ccc aac tcc ctc aat ggt ctc ccc acc ttt      192
Leu Leu Lys Ala Gln Gly Pro Asn Ser Leu Asn Gly Leu Pro Thr Phe
    50                  55                  60

cag ttc gaa acc att ccc gat ggt ctc cca ccg tcc aat gtc gac gca      240
Gln Phe Glu Thr Ile Pro Asp Gly Leu Pro Pro Ser Asn Val Asp Ala
65                  70                  75                  80

acc caa gac atc cct tcc ctc tgt gca tcc acc aaa aaa aac tgc ttg      288
Thr Gln Asp Ile Pro Ser Leu Cys Ala Ser Thr Lys Lys Asn Cys Leu
                85                  90                  95

gct ccc ttt aga cgc ctt ctc gcc aaa ctc aac gac aga ggt cct ccc      336
Ala Pro Phe Arg Arg Leu Leu Ala Lys Leu Asn Asp Arg Gly Pro Pro
            100                 105                 110
```

-continued

```
gtc act tgc ata ttt tct gac gct gtc atg agc ttc act tta gac gct      384
Val Thr Cys Ile Phe Ser Asp Ala Val Met Ser Phe Thr Leu Asp Ala
        115                 120                 125

gct caa gaa ctc ggc att ccc gac ctt ctt tta tgg aca gct agt gct      432
Ala Gln Glu Leu Gly Ile Pro Asp Leu Leu Leu Trp Thr Ala Ser Ala
    130                 135                 140

tgt ggc ttc atg gcc tat gtg cag tat cgc agt ctc atc gac aag ggt      480
Cys Gly Phe Met Ala Tyr Val Gln Tyr Arg Ser Leu Ile Asp Lys Gly
145                 150                 155                 160

ttt aca cca ctc aaa gat gag agt tat cta aca aat ggg tat ttg gat      528
Phe Thr Pro Leu Lys Asp Glu Ser Tyr Leu Thr Asn Gly Tyr Leu Asp
                165                 170                 175

act gtt gtt gat tgg ata ccg ggc atg aaa ggt atc cgt ttg aag gat      576
Thr Val Val Asp Trp Ile Pro Gly Met Lys Gly Ile Arg Leu Lys Asp
            180                 185                 190

ctc ccg agc ttc att cgg act acc gat cca gat gat atc atg ctg gac      624
Leu Pro Ser Phe Ile Arg Thr Thr Asp Pro Asp Asp Ile Met Leu Asp
        195                 200                 205

ttt gcc atg ggt gag ctt gaa agg gct cgc aag gct tct gcc atc att      672
Phe Ala Met Gly Glu Leu Glu Arg Ala Arg Lys Ala Ser Ala Ile Ile
    210                 215                 220

ttc aat acg ttt gac gct tta gag cag gag gtt ttg gat gca att gct      720
Phe Asn Thr Phe Asp Ala Leu Glu Gln Glu Val Leu Asp Ala Ile Ala
225                 230                 235                 240

ccc atg tat ccc cca atc tac acc att ggt cct ctt cag cta ctt ccg      768
Pro Met Tyr Pro Pro Ile Tyr Thr Ile Gly Pro Leu Gln Leu Leu Pro
                245                 250                 255

gat cag att cac gat agc gaa cta aag ttg att gga tca aat ctg tgg      816
Asp Gln Ile His Asp Ser Glu Leu Lys Leu Ile Gly Ser Asn Leu Trp
            260                 265                 270

aag gaa gag ccc gag tgt ctc aaa tgg ctg gat tcc aaa gaa ccc aac      864
Lys Glu Glu Pro Glu Cys Leu Lys Trp Leu Asp Ser Lys Glu Pro Asn
        275                 280                 285

tct gtt gtt tac gtt aat tat gga agc atc aca gtc atg act ccc cag      912
Ser Val Val Tyr Val Asn Tyr Gly Ser Ile Thr Val Met Thr Pro Gln
    290                 295                 300

caa ctg att gag ttt gct tgg gga ctt gca aat agc aat caa agc ttc      960
Gln Leu Ile Glu Phe Ala Trp Gly Leu Ala Asn Ser Asn Gln Ser Phe
305                 310                 315                 320

ttg tgg ata ctt agg cca gat ctc gtg tct ggt gag tcc gcc att ctg     1008
Leu Trp Ile Leu Arg Pro Asp Leu Val Ser Gly Glu Ser Ala Ile Leu
                325                 330                 335

cca cca gaa ttc gtg gca gaa aca gaa gac agg ggt tta cta gca ggt     1056
Pro Pro Glu Phe Val Ala Glu Thr Glu Asp Arg Gly Leu Leu Ala Gly
            340                 345                 350

tgg tgt cct caa gag caa gtt ctc acc cac cag gcc att ggc ggc ttc     1104
Trp Cys Pro Gln Glu Gln Val Leu Thr His Gln Ala Ile Gly Gly Phe
        355                 360                 365

tta act cat aac ggc tgg aat tcc aca att gag ggt tta tgc gct gga     1152
Leu Thr His Asn Gly Trp Asn Ser Thr Ile Glu Gly Leu Cys Ala Gly
    370                 375                 380

gtg cct atg att tgt tgg ccc ttt ttt gca gag cag caa acc aac tgt     1200
Val Pro Met Ile Cys Trp Pro Phe Phe Ala Glu Gln Gln Thr Asn Cys
385                 390                 395                 400

cgt tac tgc tgc act gag tgg ggc gta gga atg gag ata gac agt gat     1248
Arg Tyr Cys Cys Thr Glu Trp Gly Val Gly Met Glu Ile Asp Ser Asp
                405                 410                 415

gtt aag agg gat gaa gtt gca aag ctt gtg aga gag ttg atg gtg gga     1296
Val Lys Arg Asp Glu Val Ala Lys Leu Val Arg Glu Leu Met Val Gly
            420                 425                 430
```

```
gag aaa ggc aaa gta atg aaa aag aaa acc atg gag tgg aag cat agg     1344
Glu Lys Gly Lys Val Met Lys Lys Lys Thr Met Glu Trp Lys His Arg
        435                 440                 445

gca gaa gtg gct acc act ggt cca gat gga tca tct tac ttg aat ttg     1392
Ala Glu Val Ala Thr Thr Gly Pro Asp Gly Ser Ser Tyr Leu Asn Leu
    450                 455                 460

gag aaa ata ttt gaa caa gtg ctt ctc tag                             1422
Glu Lys Ile Phe Glu Gln Val Leu Leu
465                 470


<210> SEQ ID NO 22
<211> LENGTH: 473
<212> TYPE: PRT
<213> ORGANISM: Vitis sp.

<400> SEQUENCE: 22

Met Gly Ser Met Glu Lys Pro His Ala Val Cys Ile Pro Tyr Pro Ala
1               5                   10                  15

Gln Gly His Ile Asn Pro Met Leu Lys Leu Ala Lys Leu Leu His Phe
            20                  25                  30

Arg Gly Phe Arg Ile Thr Phe Val Asn Thr Glu Phe Asn His Thr Arg
        35                  40                  45

Leu Leu Lys Ala Gln Gly Pro Asn Ser Leu Asn Gly Leu Pro Thr Phe
    50                  55                  60

Gln Phe Glu Thr Ile Pro Asp Gly Leu Pro Pro Ser Asn Val Asp Ala
65                  70                  75                  80

Thr Gln Asp Ile Pro Ser Leu Cys Ala Ser Thr Lys Lys Asn Cys Leu
                85                  90                  95

Ala Pro Phe Arg Arg Leu Leu Ala Lys Leu Asn Asp Arg Gly Pro Pro
            100                 105                 110

Val Thr Cys Ile Phe Ser Asp Ala Val Met Ser Phe Thr Leu Asp Ala
        115                 120                 125

Ala Gln Glu Leu Gly Ile Pro Asp Leu Leu Leu Trp Thr Ala Ser Ala
    130                 135                 140

Cys Gly Phe Met Ala Tyr Val Gln Tyr Arg Ser Leu Ile Asp Lys Gly
145                 150                 155                 160

Phe Thr Pro Leu Lys Asp Glu Ser Tyr Leu Thr Asn Gly Tyr Leu Asp
                165                 170                 175

Thr Val Val Asp Trp Ile Pro Gly Met Lys Gly Ile Arg Leu Lys Asp
            180                 185                 190

Leu Pro Ser Phe Ile Arg Thr Thr Asp Pro Asp Asp Ile Met Leu Asp
        195                 200                 205

Phe Ala Met Gly Glu Leu Glu Arg Ala Arg Lys Ala Ser Ala Ile Ile
    210                 215                 220

Phe Asn Thr Phe Asp Ala Leu Glu Gln Glu Val Leu Asp Ala Ile Ala
225                 230                 235                 240

Pro Met Tyr Pro Pro Ile Tyr Thr Ile Gly Pro Leu Gln Leu Leu Pro
                245                 250                 255

Asp Gln Ile His Asp Ser Glu Leu Lys Leu Ile Gly Ser Asn Leu Trp
            260                 265                 270

Lys Glu Glu Pro Glu Cys Leu Lys Trp Leu Asp Ser Lys Glu Pro Asn
        275                 280                 285

Ser Val Val Tyr Val Asn Tyr Gly Ser Ile Thr Val Met Thr Pro Gln
    290                 295                 300

Gln Leu Ile Glu Phe Ala Trp Gly Leu Ala Asn Ser Asn Gln Ser Phe
```

```
305                 310                 315                 320

Leu Trp Ile Leu Arg Pro Asp Leu Val Ser Gly Glu Ser Ala Ile Leu
                325                 330                 335

Pro Pro Glu Phe Val Ala Glu Thr Glu Asp Arg Gly Leu Leu Ala Gly
            340                 345                 350

Trp Cys Pro Gln Glu Gln Val Leu Thr His Gln Ala Ile Gly Gly Phe
        355                 360                 365

Leu Thr His Asn Gly Trp Asn Ser Thr Ile Glu Gly Leu Cys Ala Gly
    370                 375                 380

Val Pro Met Ile Cys Trp Pro Phe Phe Ala Glu Gln Gln Thr Asn Cys
385                 390                 395                 400

Arg Tyr Cys Cys Thr Glu Trp Gly Val Gly Met Glu Ile Asp Ser Asp
                405                 410                 415

Val Lys Arg Asp Glu Val Ala Lys Leu Val Arg Glu Leu Met Val Gly
            420                 425                 430

Glu Lys Gly Lys Val Met Lys Lys Lys Thr Met Glu Trp Lys His Arg
        435                 440                 445

Ala Glu Val Ala Thr Thr Gly Pro Asp Gly Ser Ser Tyr Leu Asn Leu
    450                 455                 460

Glu Lys Ile Phe Glu Gln Val Leu Leu
465                 470


<210> SEQ ID NO 23
<211> LENGTH: 1455
<212> TYPE: DNA
<213> ORGANISM: Vitis sp.
<220> FEATURE:
<221> NAME/KEY: CDS
<222> LOCATION: (1)..(1452)

<400> SEQUENCE: 23

atg gca atg gcc gag aag cct cgc cct cat gcg gta tgt gtt ccg ttc       48
Met Ala Met Ala Glu Lys Pro Arg Pro His Ala Val Cys Val Pro Phe
1               5                   10                  15

cca gct caa ggc cac ata aac ccc atg atg aaa tta gca aag ctc ctc       96
Pro Ala Gln Gly His Ile Asn Pro Met Met Lys Leu Ala Lys Leu Leu
            20                  25                  30

cac cat aaa ggt ttt cac atc acc ttc gtt aac aca gag ttc aat cat      144
His His Lys Gly Phe His Ile Thr Phe Val Asn Thr Glu Phe Asn His
        35                  40                  45

caa cgc ctg ctg aaa tcc aga ggt ccc aac tcc ctt cgt ggt cta ccc      192
Gln Arg Leu Leu Lys Ser Arg Gly Pro Asn Ser Leu Arg Gly Leu Pro
    50                  55                  60

tcc ttc caa ttc gaa acc att gca gac ggc ctc cct cca tca gat atc      240
Ser Phe Gln Phe Glu Thr Ile Ala Asp Gly Leu Pro Pro Ser Asp Ile
65                  70                  75                  80

gat gcc acc caa gat gtc ccg tcc ctc tgc gcc tcc acc cac aac gac      288
Asp Ala Thr Gln Asp Val Pro Ser Leu Cys Ala Ser Thr His Asn Asp
                85                  90                  95

tgc cta gct ccc ttc cga gac ctc ctc gcc aaa ctt aac gac act tct      336
Cys Leu Ala Pro Phe Arg Asp Leu Leu Ala Lys Leu Asn Asp Thr Ser
            100                 105                 110

tca tcc aaa gtc cct cca gta act tgc ata gtt tca gat ggt atc atg      384
Ser Ser Lys Val Pro Pro Val Thr Cys Ile Val Ser Asp Gly Ile Met
        115                 120                 125

agc ttc act ctc aag gct gct gaa gaa cta ggc att cct gaa gta ttt      432
Ser Phe Thr Leu Lys Ala Ala Glu Glu Leu Gly Ile Pro Glu Val Phe
    130                 135                 140
```

```
ttc tgg aca acc agt gct tgt ggc ttc atg ggt tac gtg cag tat cgc      480
Phe Trp Thr Thr Ser Ala Cys Gly Phe Met Gly Tyr Val Gln Tyr Arg
145                 150                 155                 160

cat ctc att gat aga ggt ttt ttc cca cta aaa gat gag agt tgt cta      528
His Leu Ile Asp Arg Gly Phe Phe Pro Leu Lys Asp Glu Ser Cys Leu
                165                 170                 175

aca aat ggg cac ttg gac act gtc gta gac tgg ata cca gct atg aaa      576
Thr Asn Gly His Leu Asp Thr Val Val Asp Trp Ile Pro Ala Met Lys
            180                 185                 190

ggc gtg cgt ttg agg gat tta cca agc ttt att aga aca aca aac cca      624
Gly Val Arg Leu Arg Asp Leu Pro Ser Phe Ile Arg Thr Thr Asn Pro
        195                 200                 205

gat gat att gtg gtg aat ttt gcc atg gga gaa gtt gag aga gcc aat      672
Asp Asp Ile Val Val Asn Phe Ala Met Gly Glu Val Glu Arg Ala Asn
    210                 215                 220

gat gct tct gct atc ctc tta aat acg ttt gat gaa tta gag cat gag      720
Asp Ala Ser Ala Ile Leu Leu Asn Thr Phe Asp Glu Leu Glu His Glu
225                 230                 235                 240

gtt ctg cag gca ctt tca acc atg ttt cct cct att tac acc atc ggt      768
Val Leu Gln Ala Leu Ser Thr Met Phe Pro Pro Ile Tyr Thr Ile Gly
                245                 250                 255

ccc cta cag cta ttg ctg aat cag atg cca gac aat gat tta aag tct      816
Pro Leu Gln Leu Leu Leu Asn Gln Met Pro Asp Asn Asp Leu Lys Ser
            260                 265                 270

ata gaa tcg aac tta tgg aaa gaa gaa cca ggg tgt ctt gag tgg ctc      864
Ile Glu Ser Asn Leu Trp Lys Glu Glu Pro Gly Cys Leu Glu Trp Leu
        275                 280                 285

gac gct aaa gaa cct gag tct gtt gtg tac gtg aat ttt ggc agt gtc      912
Asp Ala Lys Glu Pro Glu Ser Val Val Tyr Val Asn Phe Gly Ser Val
    290                 295                 300

aca gtc atg aca ccc caa caa ctg gtt gaa ttt gct tgg ggt ctt gct      960
Thr Val Met Thr Pro Gln Gln Leu Val Glu Phe Ala Trp Gly Leu Ala
305                 310                 315                 320

aat gcc aat ctg aaa ttt ttg tgg ata atc agg cca gat ctt gtt gcc     1008
Asn Ala Asn Leu Lys Phe Leu Trp Ile Ile Arg Pro Asp Leu Val Ala
                325                 330                 335

gga gat gct gcc att ctt cca gca gat ttc gtg gca cag aca aaa gaa     1056
Gly Asp Ala Ala Ile Leu Pro Ala Asp Phe Val Ala Gln Thr Lys Glu
            340                 345                 350

agg agt ttg tta gca agt tgg tgc cct caa gaa cga gtt ctc aca cac     1104
Arg Ser Leu Leu Ala Ser Trp Cys Pro Gln Glu Arg Val Leu Thr His
        355                 360                 365

cct gca att gga ggg ttt tta aca cac agc ggc tgg aat tcc aca att     1152
Pro Ala Ile Gly Gly Phe Leu Thr His Ser Gly Trp Asn Ser Thr Ile
    370                 375                 380

gaa ggc ttg tgc ggc ggg gta ccc atg atc tgt tgg ccc ttc ttt gca     1200
Glu Gly Leu Cys Gly Gly Val Pro Met Ile Cys Trp Pro Phe Phe Ala
385                 390                 395                 400

gag cag atg acc aac tgc aga tat tgt tgc aca gag tgg ggc gta ggc     1248
Glu Gln Met Thr Asn Cys Arg Tyr Cys Cys Thr Glu Trp Gly Val Gly
                405                 410                 415

atg gag ata ggc aat gat gtt acg aga gat gaa gtt gag agc ctt gtg     1296
Met Glu Ile Gly Asn Asp Val Thr Arg Asp Glu Val Glu Ser Leu Val
            420                 425                 430

aga ggt ttg atg gaa gga gag aaa ggt aaa gag atg aag aag aaa gca     1344
Arg Gly Leu Met Glu Gly Glu Lys Gly Lys Glu Met Lys Lys Lys Ala
        435                 440                 445

atg gaa tgg aaa agg atg gca gaa gca gcc act acc act ccg gct ggt     1392
Met Glu Trp Lys Arg Met Ala Glu Ala Ala Thr Thr Thr Pro Ala Gly
    450                 455                 460
```

```
tca tct tac tca aat ctg gac aaa atg att aac caa gtg ctt ctc tcc      1440
Ser Ser Tyr Ser Asn Leu Asp Lys Met Ile Asn Gln Val Leu Leu Ser
465                 470                 475                 480

aaa tca cca tgt taa                                                  1455
Lys Ser Pro Cys


<210> SEQ ID NO 24
<211> LENGTH: 484
<212> TYPE: PRT
<213> ORGANISM: Vitis sp.

<400> SEQUENCE: 24

Met Ala Met Ala Glu Lys Pro Arg Pro His Ala Val Cys Val Pro Phe
1               5                   10                  15

Pro Ala Gln Gly His Ile Asn Pro Met Met Lys Leu Ala Lys Leu Leu
            20                  25                  30

His His Lys Gly Phe His Ile Thr Phe Val Asn Thr Glu Phe Asn His
        35                  40                  45

Gln Arg Leu Leu Lys Ser Arg Gly Pro Asn Ser Leu Arg Gly Leu Pro
    50                  55                  60

Ser Phe Gln Phe Glu Thr Ile Ala Asp Gly Leu Pro Pro Ser Asp Ile
65                  70                  75                  80

Asp Ala Thr Gln Asp Val Pro Ser Leu Cys Ala Ser Thr His Asn Asp
                85                  90                  95

Cys Leu Ala Pro Phe Arg Asp Leu Leu Ala Lys Leu Asn Asp Thr Ser
            100                 105                 110

Ser Ser Lys Val Pro Pro Val Thr Cys Ile Val Ser Asp Gly Ile Met
        115                 120                 125

Ser Phe Thr Leu Lys Ala Ala Glu Glu Leu Gly Ile Pro Glu Val Phe
    130                 135                 140

Phe Trp Thr Thr Ser Ala Cys Gly Phe Met Gly Tyr Val Gln Tyr Arg
145                 150                 155                 160

His Leu Ile Asp Arg Gly Phe Phe Pro Leu Lys Asp Glu Ser Cys Leu
                165                 170                 175

Thr Asn Gly His Leu Asp Thr Val Val Asp Trp Ile Pro Ala Met Lys
            180                 185                 190

Gly Val Arg Leu Arg Asp Leu Pro Ser Phe Ile Arg Thr Thr Asn Pro
        195                 200                 205

Asp Asp Ile Val Val Asn Phe Ala Met Gly Glu Val Glu Arg Ala Asn
    210                 215                 220

Asp Ala Ser Ala Ile Leu Leu Asn Thr Phe Asp Glu Leu Glu His Glu
225                 230                 235                 240

Val Leu Gln Ala Leu Ser Thr Met Phe Pro Pro Ile Tyr Thr Ile Gly
                245                 250                 255

Pro Leu Gln Leu Leu Leu Asn Gln Met Pro Asp Asn Asp Leu Lys Ser
            260                 265                 270

Ile Glu Ser Asn Leu Trp Lys Glu Glu Pro Gly Cys Leu Glu Trp Leu
        275                 280                 285

Asp Ala Lys Glu Pro Glu Ser Val Val Tyr Val Asn Phe Gly Ser Val
    290                 295                 300

Thr Val Met Thr Pro Gln Gln Leu Val Glu Phe Ala Trp Gly Leu Ala
305                 310                 315                 320

Asn Ala Asn Leu Lys Phe Leu Trp Ile Ile Arg Pro Asp Leu Val Ala
                325                 330                 335
```

```
Gly Asp Ala Ala Ile Leu Pro Ala Asp Phe Val Ala Gln Thr Lys Glu
            340                 345                 350

Arg Ser Leu Leu Ala Ser Trp Cys Pro Gln Glu Arg Val Leu Thr His
        355                 360                 365

Pro Ala Ile Gly Gly Phe Leu Thr His Ser Gly Trp Asn Ser Thr Ile
    370                 375                 380

Glu Gly Leu Cys Gly Gly Val Pro Met Ile Cys Trp Pro Phe Phe Ala
385                 390                 395                 400

Glu Gln Met Thr Asn Cys Arg Tyr Cys Cys Thr Glu Trp Gly Val Gly
                405                 410                 415

Met Glu Ile Gly Asn Asp Val Thr Arg Asp Glu Val Glu Ser Leu Val
            420                 425                 430

Arg Gly Leu Met Glu Gly Glu Lys Gly Lys Glu Met Lys Lys Lys Ala
        435                 440                 445

Met Glu Trp Lys Arg Met Ala Glu Ala Ala Thr Thr Thr Pro Ala Gly
    450                 455                 460

Ser Ser Tyr Ser Asn Leu Asp Lys Met Ile Asn Gln Val Leu Leu Ser
465                 470                 475                 480

Lys Ser Pro Cys


<210> SEQ ID NO 25
<211> LENGTH: 1458
<212> TYPE: DNA
<213> ORGANISM: Ipomoea batatas
<220> FEATURE:
<221> NAME/KEY: CDS
<222> LOCATION: (1)..(1455)

<400> SEQUENCE: 25

atg ggt tct ctt agc tca gaa cta gac aag ccc cat gca gtg tgc ata       48
Met Gly Ser Leu Ser Ser Glu Leu Asp Lys Pro His Ala Val Cys Ile
1               5                   10                  15

cca tat cct gct caa ggc cat atc aac ccc atg cta aaa cta gcc aag       96
Pro Tyr Pro Ala Gln Gly His Ile Asn Pro Met Leu Lys Leu Ala Lys
            20                  25                  30

att ctc cac cac aaa ggc ttc cac atc acc ttt gtc aac aca gaa ttc      144
Ile Leu His His Lys Gly Phe His Ile Thr Phe Val Asn Thr Glu Phe
        35                  40                  45

aac cac cgc cgc ctg gag aga acc cgg ggg ccg gaa tct ctc cgg ggc      192
Asn His Arg Arg Leu Glu Arg Thr Arg Gly Pro Glu Ser Leu Arg Gly
    50                  55                  60

ctg ccg tct ttc cgt ttt gag acc att ccc gac ggg ctt ccc gtg tcg      240
Leu Pro Ser Phe Arg Phe Glu Thr Ile Pro Asp Gly Leu Pro Val Ser
65                  70                  75                  80

gac gcg gat gtc acc cag gat atc ccc tcg ctc tgc gag tct act agt      288
Asp Ala Asp Val Thr Gln Asp Ile Pro Ser Leu Cys Glu Ser Thr Ser
                85                  90                  95

gcc act tgt ttg ggt cct ttt aag gac ctt ctt gcc cgg ctt aat gac      336
Ala Thr Cys Leu Gly Pro Phe Lys Asp Leu Leu Ala Arg Leu Asn Asp
            100                 105                 110

aca gcc gtg tca aac gcc ccc ccg gtg tcc tgc ata gtc tcc gac ggg      384
Thr Ala Val Ser Asn Ala Pro Pro Val Ser Cys Ile Val Ser Asp Gly
        115                 120                 125

gtc atg agc ttc acc gtc gat gcc gcc gag gag ctg ggc atc ccg gaa      432
Val Met Ser Phe Thr Val Asp Ala Ala Glu Glu Leu Gly Ile Pro Glu
    130                 135                 140

gtc ctg ttc tgg act act agc gca tgt ggg ttc ttg ggt tac atg cat      480
Val Leu Phe Trp Thr Thr Ser Ala Cys Gly Phe Leu Gly Tyr Met His
145                 150                 155                 160
```

```
ttc act caa ctc ctc gac aag ggc tac acc cct ctc aaa gat gag agt      528
Phe Thr Gln Leu Leu Asp Lys Gly Tyr Thr Pro Leu Lys Asp Glu Ser
                165                 170                 175

tac ctg aca aat ggg tat cta gag acg gag ttg gat tgg gta aaa ggc      576
Tyr Leu Thr Asn Gly Tyr Leu Glu Thr Glu Leu Asp Trp Val Lys Gly
            180                 185                 190

atg aaa ggc ata cgt ttg aga gat att cca tct ttc ttg aga acc aca      624
Met Lys Gly Ile Arg Leu Arg Asp Ile Pro Ser Phe Leu Arg Thr Thr
        195                 200                 205

aat cca gat gaa tat atg ttg aag ttc atc tta caa gaa aca ggg aga      672
Asn Pro Asp Glu Tyr Met Leu Lys Phe Ile Leu Gln Glu Thr Gly Arg
    210                 215                 220

gcg aga agg gct tct gcc atc att ctc aac acc ttt gac gcg ttg gag      720
Ala Arg Arg Ala Ser Ala Ile Ile Leu Asn Thr Phe Asp Ala Leu Glu
225                 230                 235                 240

cat gaa gct tta atg gcg ctt cag tcc atg ctc ccg ccg gtg tac gcc      768
His Glu Ala Leu Met Ala Leu Gln Ser Met Leu Pro Pro Val Tyr Ala
                245                 250                 255

gtc ggc cca tta cag ttc ctc cag aca cag gtc aaa gac agc aac gta      816
Val Gly Pro Leu Gln Phe Leu Gln Thr Gln Val Lys Asp Ser Asn Val
            260                 265                 270

aga gca ctg gca tcg aac ctc tgg aaa gag gac acc tcc tgt ctg gaa      864
Arg Ala Leu Ala Ser Asn Leu Trp Lys Glu Asp Thr Ser Cys Leu Glu
        275                 280                 285

tgg ctg gac acg aaa gag cca aac tcg gtc gtc tat gtt aac tac ggc      912
Trp Leu Asp Thr Lys Glu Pro Asn Ser Val Val Tyr Val Asn Tyr Gly
    290                 295                 300

agc ata aca gtg atg aca cca gac cag ctc ttg gag ttc gcc tgg gga      960
Ser Ile Thr Val Met Thr Pro Asp Gln Leu Leu Glu Phe Ala Trp Gly
305                 310                 315                 320

tta gcg aac tcc aag aaa cca ttc ttg tgg atc gtc cgg ccc gac ctg     1008
Leu Ala Asn Ser Lys Lys Pro Phe Leu Trp Ile Val Arg Pro Asp Leu
                325                 330                 335

gtc acc ggc gag gct gcg ata att cca ccc gaa ttc ttg gag gaa act     1056
Val Thr Gly Glu Ala Ala Ile Ile Pro Pro Glu Phe Leu Glu Glu Thr
            340                 345                 350

aaa gac agg gga atg ctt tcg agc tgg tgc tcc cag gaa caa gtt ctg     1104
Lys Asp Arg Gly Met Leu Ser Ser Trp Cys Ser Gln Glu Gln Val Leu
        355                 360                 365

aac cac cca gcc atc ggg gga ttc ttg acc cac aac gga tgg aac tcg     1152
Asn His Pro Ala Ile Gly Gly Phe Leu Thr His Asn Gly Trp Asn Ser
    370                 375                 380

act ctc gag agc atc tgc agc ggg gtg cca atg ctg tgc tgg ccg ttc     1200
Thr Leu Glu Ser Ile Cys Ser Gly Val Pro Met Leu Cys Trp Pro Phe
385                 390                 395                 400

ttc gcc gag cag cag acc aat tgc cac tat gct tgc agt aaa tgg ggg     1248
Phe Ala Glu Gln Gln Thr Asn Cys His Tyr Ala Cys Ser Lys Trp Gly
                405                 410                 415

att ggc aag gaa att gac agc aat gtg aag agg gat gaa gtt gag aag     1296
Ile Gly Lys Glu Ile Asp Ser Asn Val Lys Arg Asp Glu Val Glu Lys
            420                 425                 430

ctt gtg agg gag tta atg gag gga gag aaa gga gga gag atg aag aag     1344
Leu Val Arg Glu Leu Met Glu Gly Glu Lys Gly Gly Glu Met Lys Lys
        435                 440                 445

aaa gcc atg gaa tgg aag aag tta gca gaa gaa gct gca act tct tcc     1392
Lys Ala Met Glu Trp Lys Lys Leu Ala Glu Glu Ala Ala Thr Ser Ser
    450                 455                 460

att gga tca tca cac atc aac ata gac aaa ctc atc aat ctt cat ctc     1440
Ile Gly Ser Ser His Ile Asn Ile Asp Lys Leu Ile Asn Leu His Leu
```

```
465                 470                 475                 480

ctt cct cca aaa tat taa                                             1458
Leu Pro Pro Lys Tyr
                485


<210> SEQ ID NO 26
<211> LENGTH: 485
<212> TYPE: PRT
<213> ORGANISM: Ipomoea batatas

<400> SEQUENCE: 26

Met Gly Ser Leu Ser Ser Glu Leu Asp Lys Pro His Ala Val Cys Ile
1               5                   10                  15

Pro Tyr Pro Ala Gln Gly His Ile Asn Pro Met Leu Lys Leu Ala Lys
            20                  25                  30

Ile Leu His His Lys Gly Phe His Ile Thr Phe Val Asn Thr Glu Phe
        35                  40                  45

Asn His Arg Arg Leu Glu Arg Thr Arg Gly Pro Glu Ser Leu Arg Gly
    50                  55                  60

Leu Pro Ser Phe Arg Phe Glu Thr Ile Pro Asp Gly Leu Pro Val Ser
65                  70                  75                  80

Asp Ala Asp Val Thr Gln Asp Ile Pro Ser Leu Cys Glu Ser Thr Ser
                85                  90                  95

Ala Thr Cys Leu Gly Pro Phe Lys Asp Leu Leu Ala Arg Leu Asn Asp
            100                 105                 110

Thr Ala Val Ser Asn Ala Pro Pro Val Ser Cys Ile Val Ser Asp Gly
        115                 120                 125

Val Met Ser Phe Thr Val Asp Ala Ala Glu Glu Leu Gly Ile Pro Glu
    130                 135                 140

Val Leu Phe Trp Thr Thr Ser Ala Cys Gly Phe Leu Gly Tyr Met His
145                 150                 155                 160

Phe Thr Gln Leu Leu Asp Lys Gly Tyr Thr Pro Leu Lys Asp Glu Ser
                165                 170                 175

Tyr Leu Thr Asn Gly Tyr Leu Glu Thr Glu Leu Asp Trp Val Lys Gly
            180                 185                 190

Met Lys Gly Ile Arg Leu Arg Asp Ile Pro Ser Phe Leu Arg Thr Thr
        195                 200                 205

Asn Pro Asp Glu Tyr Met Leu Lys Phe Ile Leu Gln Glu Thr Gly Arg
    210                 215                 220

Ala Arg Arg Ala Ser Ala Ile Ile Leu Asn Thr Phe Asp Ala Leu Glu
225                 230                 235                 240

His Glu Ala Leu Met Ala Leu Gln Ser Met Leu Pro Pro Val Tyr Ala
                245                 250                 255

Val Gly Pro Leu Gln Phe Leu Gln Thr Gln Val Lys Asp Ser Asn Val
            260                 265                 270

Arg Ala Leu Ala Ser Asn Leu Trp Lys Glu Asp Thr Ser Cys Leu Glu
        275                 280                 285

Trp Leu Asp Thr Lys Glu Pro Asn Ser Val Val Tyr Val Asn Tyr Gly
    290                 295                 300

Ser Ile Thr Val Met Thr Pro Asp Gln Leu Leu Glu Phe Ala Trp Gly
305                 310                 315                 320

Leu Ala Asn Ser Lys Lys Pro Phe Leu Trp Ile Val Arg Pro Asp Leu
                325                 330                 335

Val Thr Gly Glu Ala Ala Ile Ile Pro Pro Glu Phe Leu Glu Glu Thr
            340                 345                 350
```

```
Lys Asp Arg Gly Met Leu Ser Ser Trp Cys Ser Gln Glu Gln Val Leu
        355                 360                 365

Asn His Pro Ala Ile Gly Gly Phe Leu Thr His Asn Gly Trp Asn Ser
    370                 375                 380

Thr Leu Glu Ser Ile Cys Ser Gly Val Pro Met Leu Cys Trp Pro Phe
385                 390                 395                 400

Phe Ala Glu Gln Gln Thr Asn Cys His Tyr Ala Cys Ser Lys Trp Gly
                405                 410                 415

Ile Gly Lys Glu Ile Asp Ser Asn Val Lys Arg Asp Glu Val Glu Lys
            420                 425                 430

Leu Val Arg Glu Leu Met Glu Gly Glu Lys Gly Gly Glu Met Lys Lys
        435                 440                 445

Lys Ala Met Glu Trp Lys Lys Leu Ala Glu Glu Ala Ala Thr Ser Ser
    450                 455                 460

Ile Gly Ser Ser His Ile Asn Ile Asp Lys Leu Ile Asn Leu His Leu
465                 470                 475                 480

Leu Pro Pro Lys Tyr
                485


<210> SEQ ID NO 27
<211> LENGTH: 1470
<212> TYPE: DNA
<213> ORGANISM: Arabidopsis thaliana
<220> FEATURE:
<221> NAME/KEY: CDS
<222> LOCATION: (1)..(1467)

<400> SEQUENCE: 27

atg gga tct cag atc att cat aac tca caa aaa cca cat gta gtt tgt       48
Met Gly Ser Gln Ile Ile His Asn Ser Gln Lys Pro His Val Val Cys
1               5                   10                  15

gtt cca tat ccg gct caa ggc cac atc aac cct atg atg aga gtg gct       96
Val Pro Tyr Pro Ala Gln Gly His Ile Asn Pro Met Met Arg Val Ala
            20                  25                  30

aaa ctc ctc cac gcc aga ggc ttc tac gtc acc ttc gtc aac acc gtc      144
Lys Leu Leu His Ala Arg Gly Phe Tyr Val Thr Phe Val Asn Thr Val
        35                  40                  45

tac aac cac aat cgt ttc ctt cgt tct cgt ggg tcc aat gcc cta gat      192
Tyr Asn His Asn Arg Phe Leu Arg Ser Arg Gly Ser Asn Ala Leu Asp
    50                  55                  60

gga ctt cct tcg ttc cga ttt gag tcc att gct gac ggt cta cca gag      240
Gly Leu Pro Ser Phe Arg Phe Glu Ser Ile Ala Asp Gly Leu Pro Glu
65                  70                  75                  80

aca gac atg gat gcc acg cag gac atc aca gct ctt tgc gag tcc acc      288
Thr Asp Met Asp Ala Thr Gln Asp Ile Thr Ala Leu Cys Glu Ser Thr
                85                  90                  95

atg aag aac tgt ctc gct ccg ttc aga gag ctt ctc cag cgg atc aac      336
Met Lys Asn Cys Leu Ala Pro Phe Arg Glu Leu Leu Gln Arg Ile Asn
            100                 105                 110

gct gga gat aat gtt cct ccg gta agc tgt att gta tct gac ggt tgt      384
Ala Gly Asp Asn Val Pro Pro Val Ser Cys Ile Val Ser Asp Gly Cys
        115                 120                 125

atg agc ttt act ctt gat gtt gcg gag gag ctt gga gtc ccg gag gtt      432
Met Ser Phe Thr Leu Asp Val Ala Glu Glu Leu Gly Val Pro Glu Val
    130                 135                 140

ctt ttt tgg aca acc agt ggc tgt gcg ttc ctg gct tat cta cac ttt      480
Leu Phe Trp Thr Thr Ser Gly Cys Ala Phe Leu Ala Tyr Leu His Phe
145                 150                 155                 160
```

-continued

```
tat ctc ttc atc gag aag ggc tta tgt ccg cta aaa gat gag agt tac      528
Tyr Leu Phe Ile Glu Lys Gly Leu Cys Pro Leu Lys Asp Glu Ser Tyr
                165                 170                 175

ttg acg aag gag tac tta gaa gac acg gtt ata gat ttt ata cca acc      576
Leu Thr Lys Glu Tyr Leu Glu Asp Thr Val Ile Asp Phe Ile Pro Thr
            180                 185                 190

atg aag aat gtg aaa cta aag gat att cct agc ttc ata cgt acc act      624
Met Lys Asn Val Lys Leu Lys Asp Ile Pro Ser Phe Ile Arg Thr Thr
        195                 200                 205

aat cct gat gat gtt atg att agt ttc gcc ctc cgc gag acc gag cga      672
Asn Pro Asp Asp Val Met Ile Ser Phe Ala Leu Arg Glu Thr Glu Arg
    210                 215                 220

gcc aaa cgt gct tct gct atc att cta aac aca ttt gat gac ctt gag      720
Ala Lys Arg Ala Ser Ala Ile Ile Leu Asn Thr Phe Asp Asp Leu Glu
225                 230                 235                 240

cat gat gtt gtt cat gct atg caa tct atc tta cct ccg gtt tat tca      768
His Asp Val Val His Ala Met Gln Ser Ile Leu Pro Pro Val Tyr Ser
                245                 250                 255

gtt gga ccg ctt cat ctc tta gca aac cgg gag att gaa gaa ggt agt      816
Val Gly Pro Leu His Leu Leu Ala Asn Arg Glu Ile Glu Glu Gly Ser
            260                 265                 270

gag att gga atg atg agt tcg aat tta tgg aaa gag gag atg gag tgt      864
Glu Ile Gly Met Met Ser Ser Asn Leu Trp Lys Glu Glu Met Glu Cys
        275                 280                 285

ttg gat tgg ctt gat act aag act caa aat agt gtc att tat atc aac      912
Leu Asp Trp Leu Asp Thr Lys Thr Gln Asn Ser Val Ile Tyr Ile Asn
    290                 295                 300

ttt ggg agc ata acg gtt ttg agt gtg aag cag ctt gtg gag ttt gct      960
Phe Gly Ser Ile Thr Val Leu Ser Val Lys Gln Leu Val Glu Phe Ala
305                 310                 315                 320

tgg ggt ttg gcg gga agt ggg aaa gag ttt tta tgg gtg atc cgg cca     1008
Trp Gly Leu Ala Gly Ser Gly Lys Glu Phe Leu Trp Val Ile Arg Pro
                325                 330                 335

gat tta gta gcg gga gag gag gct atg gtt ccg ccg gac ttt tta atg     1056
Asp Leu Val Ala Gly Glu Glu Ala Met Val Pro Pro Asp Phe Leu Met
            340                 345                 350

gag act aaa gac cgc agt atg cta gcg agt tgg tgt cct caa gag aaa     1104
Glu Thr Lys Asp Arg Ser Met Leu Ala Ser Trp Cys Pro Gln Glu Lys
        355                 360                 365

gta ctt tct cat cct gct att gga ggg ttt ttg acg cat tgc ggg tgg     1152
Val Leu Ser His Pro Ala Ile Gly Gly Phe Leu Thr His Cys Gly Trp
    370                 375                 380

aac tcg ata ttg gaa agt ctt tcg tgt gga gtt ccg atg gtg tgt tgg     1200
Asn Ser Ile Leu Glu Ser Leu Ser Cys Gly Val Pro Met Val Cys Trp
385                 390                 395                 400

cca ttt ttt gct gac cag caa atg aat tgt aag ttt tgt tgt gac gag     1248
Pro Phe Phe Ala Asp Gln Gln Met Asn Cys Lys Phe Cys Cys Asp Glu
                405                 410                 415

tgg gat gtt ggg att gag ata ggt gga gat gtg aag aga gag gaa gtt     1296
Trp Asp Val Gly Ile Glu Ile Gly Gly Asp Val Lys Arg Glu Glu Val
            420                 425                 430

gag gcg gtg gtt aga gag ctc atg gat gga gag aag gga aag aaa atg     1344
Glu Ala Val Val Arg Glu Leu Met Asp Gly Glu Lys Gly Lys Lys Met
        435                 440                 445

aga gaa aag gcg gta gag tgg cag cgc tta gcc gag aaa gcg acg gaa     1392
Arg Glu Lys Ala Val Glu Trp Gln Arg Leu Ala Glu Lys Ala Thr Glu
    450                 455                 460

cat aaa ctt ggt tct tcc gtt atg aat ttt gag acg gtt gtt agc aag     1440
His Lys Leu Gly Ser Ser Val Met Asn Phe Glu Thr Val Val Ser Lys
465                 470                 475                 480
```

```
ttt ctt ttg gga caa aaa tca cag gat taa                          1470
Phe Leu Leu Gly Gln Lys Ser Gln Asp
                485


<210> SEQ ID NO 28
<211> LENGTH: 489
<212> TYPE: PRT
<213> ORGANISM: Arabidopsis thaliana

<400> SEQUENCE: 28

Met Gly Ser Gln Ile Ile His Asn Ser Gln Lys Pro His Val Val Cys
1               5                   10                  15

Val Pro Tyr Pro Ala Gln Gly His Ile Asn Pro Met Met Arg Val Ala
            20                  25                  30

Lys Leu Leu His Ala Arg Gly Phe Tyr Val Thr Phe Val Asn Thr Val
        35                  40                  45

Tyr Asn His Asn Arg Phe Leu Arg Ser Arg Gly Ser Asn Ala Leu Asp
    50                  55                  60

Gly Leu Pro Ser Phe Arg Phe Glu Ser Ile Ala Asp Gly Leu Pro Glu
65                  70                  75                  80

Thr Asp Met Asp Ala Thr Gln Asp Ile Thr Ala Leu Cys Glu Ser Thr
                85                  90                  95

Met Lys Asn Cys Leu Ala Pro Phe Arg Glu Leu Leu Gln Arg Ile Asn
            100                 105                 110

Ala Gly Asp Asn Val Pro Pro Val Ser Cys Ile Val Ser Asp Gly Cys
        115                 120                 125

Met Ser Phe Thr Leu Asp Val Ala Glu Glu Leu Gly Val Pro Glu Val
    130                 135                 140

Leu Phe Trp Thr Thr Ser Gly Cys Ala Phe Leu Ala Tyr Leu His Phe
145                 150                 155                 160

Tyr Leu Phe Ile Glu Lys Gly Leu Cys Pro Leu Lys Asp Glu Ser Tyr
                165                 170                 175

Leu Thr Lys Glu Tyr Leu Glu Asp Thr Val Ile Asp Phe Ile Pro Thr
            180                 185                 190

Met Lys Asn Val Lys Leu Lys Asp Ile Pro Ser Phe Ile Arg Thr Thr
        195                 200                 205

Asn Pro Asp Asp Val Met Ile Ser Phe Ala Leu Arg Glu Thr Glu Arg
    210                 215                 220

Ala Lys Arg Ala Ser Ala Ile Ile Leu Asn Thr Phe Asp Asp Leu Glu
225                 230                 235                 240

His Asp Val Val His Ala Met Gln Ser Ile Leu Pro Pro Val Tyr Ser
                245                 250                 255

Val Gly Pro Leu His Leu Leu Ala Asn Arg Glu Ile Glu Glu Gly Ser
            260                 265                 270

Glu Ile Gly Met Met Ser Ser Asn Leu Trp Lys Glu Glu Met Glu Cys
        275                 280                 285

Leu Asp Trp Leu Asp Thr Lys Thr Gln Asn Ser Val Ile Tyr Ile Asn
    290                 295                 300

Phe Gly Ser Ile Thr Val Leu Ser Val Lys Gln Leu Val Glu Phe Ala
305                 310                 315                 320

Trp Gly Leu Ala Gly Ser Gly Lys Glu Phe Leu Trp Val Ile Arg Pro
                325                 330                 335

Asp Leu Val Ala Gly Glu Glu Ala Met Val Pro Pro Asp Phe Leu Met
            340                 345                 350
```

Glu Thr Lys Asp Arg Ser Met Leu Ala Ser Trp Cys Pro Gln Glu Lys
355 360 365

Val Leu Ser His Pro Ala Ile Gly Gly Phe Leu Thr His Cys Gly Trp
370 375 380

Asn Ser Ile Leu Glu Ser Leu Ser Cys Gly Val Pro Met Val Cys Trp
385 390 395 400

Pro Phe Phe Ala Asp Gln Gln Met Asn Cys Lys Phe Cys Cys Asp Glu
405 410 415

Trp Asp Val Gly Ile Glu Ile Gly Gly Asp Val Lys Arg Glu Glu Val
420 425 430

Glu Ala Val Val Arg Glu Leu Met Asp Gly Glu Lys Gly Lys Lys Met
435 440 445

Arg Glu Lys Ala Val Glu Trp Gln Arg Leu Ala Glu Lys Ala Thr Glu
450 455 460

His Lys Leu Gly Ser Ser Val Met Asn Phe Glu Thr Val Val Ser Lys
465 470 475 480

Phe Leu Leu Gly Gln Lys Ser Gln Asp
485

<210> SEQ ID NO 29
<211> LENGTH: 1467
<212> TYPE: DNA
<213> ORGANISM: Arabidopsis thaliana
<220> FEATURE:
<221> NAME/KEY: CDS
<222> LOCATION: (1)..(1464)

<400> SEQUENCE: 29 atg gga tcc cgt ttt gtt tct aac gaa caa aaa cca cac gta gtt tgc 48
Met Gly Ser Arg Phe Val Ser Asn Glu Gln Lys Pro His Val Val Cys
1 5 10 15 gtg cct tac cca gct caa ggc cac att aac cct atg atg aaa gtg gct 96
Val Pro Tyr Pro Ala Gln Gly His Ile Asn Pro Met Met Lys Val Ala
20 25 30 aaa ctc ctc cac gtc aaa ggc ttc cac gtc acc ttc gtc aac acc gtc 144
Lys Leu Leu His Val Lys Gly Phe His Val Thr Phe Val Asn Thr Val
35 40 45 tac aac cac aac cgt cta ctc cga tcc cgt ggg gcc aac gca ctc gat 192
Tyr Asn His Asn Arg Leu Leu Arg Ser Arg Gly Ala Asn Ala Leu Asp
50 55 60 gga ctt cct tcc ttc cag ttc gag tca ata cct gac ggt ctt ccg gag 240
Gly Leu Pro Ser Phe Gln Phe Glu Ser Ile Pro Asp Gly Leu Pro Glu
65 70 75 80 act ggc gtg gac gcc acg cag gac atc cct gcc ctt tcc gag tcc aca 288
Thr Gly Val Asp Ala Thr Gln Asp Ile Pro Ala Leu Ser Glu Ser Thr
85 90 95 acg aaa aac tgt ctc gtt ccg ttc aag aag ctt ctc cag cgg att gtc 336
Thr Lys Asn Cys Leu Val Pro Phe Lys Lys Leu Leu Gln Arg Ile Val
100 105 110 acg aga gag gat gtc cct ccg gtg agc tgt att gta tca gat ggt tcg 384
Thr Arg Glu Asp Val Pro Pro Val Ser Cys Ile Val Ser Asp Gly Ser
115 120 125 atg agc ttt act ctt gac gta gcg gaa gag ctt ggt gtt ccg gag att 432
Met Ser Phe Thr Leu Asp Val Ala Glu Glu Leu Gly Val Pro Glu Ile
130 135 140 cat ttt tgg acc act agt gct tgt ggc ttc atg gct tat cta cac ttt 480
His Phe Trp Thr Thr Ser Ala Cys Gly Phe Met Ala Tyr Leu His Phe
145 150 155 160 tat ctc ttc atc gag aag ggt tta tgt cca gta aaa gat gcg agt tgc 528

```
Tyr Leu Phe Ile Glu Lys Gly Leu Cys Pro Val Lys Asp Ala Ser Cys
                165                 170                 175

ttg acg aag gaa tac ttg gac aca gtt ata gat tgg ata ccg tca atg      576
Leu Thr Lys Glu Tyr Leu Asp Thr Val Ile Asp Trp Ile Pro Ser Met
            180                 185                 190

aac aat gta aaa cta aaa gac att cct agt ttt ata cgt acc act aat      624
Asn Asn Val Lys Leu Lys Asp Ile Pro Ser Phe Ile Arg Thr Thr Asn
        195                 200                 205

cct aac gac ata atg ctc aac ttc gtt gtc cgt gag gca tgt cga acc      672
Pro Asn Asp Ile Met Leu Asn Phe Val Val Arg Glu Ala Cys Arg Thr
    210                 215                 220

aaa cgt gcc tct gct atc att ctg aac acg ttt gat gac ctt gaa cat      720
Lys Arg Ala Ser Ala Ile Ile Leu Asn Thr Phe Asp Asp Leu Glu His
225                 230                 235                 240

gac ata atc cag tct atg caa tcc att tta cca ccg gtt tat cca atc      768
Asp Ile Ile Gln Ser Met Gln Ser Ile Leu Pro Pro Val Tyr Pro Ile
                245                 250                 255

gga ccg ctt cat ctc tta gta aac agg gag att gaa gaa gat agt gag      816
Gly Pro Leu His Leu Leu Val Asn Arg Glu Ile Glu Glu Asp Ser Glu
            260                 265                 270

att gga agg atg gga tca aat cta tgg aaa gag gag act gag tgc ttg      864
Ile Gly Arg Met Gly Ser Asn Leu Trp Lys Glu Glu Thr Glu Cys Leu
        275                 280                 285

gga tgg ctt aat act aag tct cga aat agc gtt gtt tat gtt aac ttt      912
Gly Trp Leu Asn Thr Lys Ser Arg Asn Ser Val Val Tyr Val Asn Phe
    290                 295                 300

ggg agc ata aca ata atg acc acg gca cag ctt ttg gag ttt gct tgg      960
Gly Ser Ile Thr Ile Met Thr Thr Ala Gln Leu Leu Glu Phe Ala Trp
305                 310                 315                 320

ggt ttg gcg gca acg gga aag gag ttt cta tgg gtg atg cgg ccg gat     1008
Gly Leu Ala Ala Thr Gly Lys Glu Phe Leu Trp Val Met Arg Pro Asp
                325                 330                 335

tca gta gcc gga gag gag gca gtg att cca aaa gag ttt tta gcg gag     1056
Ser Val Ala Gly Glu Glu Ala Val Ile Pro Lys Glu Phe Leu Ala Glu
            340                 345                 350

aca gct gat cga aga atg ctg aca agt tgg tgt cct cag gag aaa gtt     1104
Thr Ala Asp Arg Arg Met Leu Thr Ser Trp Cys Pro Gln Glu Lys Val
        355                 360                 365

ctt tct cat ccg gcg gtc gga ggg ttc ttg acc cat tgc ggg tgg aat     1152
Leu Ser His Pro Ala Val Gly Gly Phe Leu Thr His Cys Gly Trp Asn
    370                 375                 380

tcg acg tta gaa agt ctt tca tgc gga gtt cca atg gta tgt tgg cca     1200
Ser Thr Leu Glu Ser Leu Ser Cys Gly Val Pro Met Val Cys Trp Pro
385                 390                 395                 400

ttt ttt gct gag caa caa aca aat tgt aag ttt tct tgt gat gaa tgg     1248
Phe Phe Ala Glu Gln Gln Thr Asn Cys Lys Phe Ser Cys Asp Glu Trp
                405                 410                 415

gag gtt ggt att gag atc ggt gga gat gtc aag agg gga gag gtt gag     1296
Glu Val Gly Ile Glu Ile Gly Gly Asp Val Lys Arg Gly Glu Val Glu
            420                 425                 430

gcg gtg gtt aga gag ctc atg gat gga gag aaa gga aag aaa atg aga     1344
Ala Val Val Arg Glu Leu Met Asp Gly Glu Lys Gly Lys Lys Met Arg
        435                 440                 445

gag aag gct gta gag tgg cgg cgc ttg gcc gag aaa gct aca aag ctt     1392
Glu Lys Ala Val Glu Trp Arg Arg Leu Ala Glu Lys Ala Thr Lys Leu
    450                 455                 460

ccg tgt ggt tcg tcg gtg ata aat ttt gag acg att gtc aac aag gtt     1440
Pro Cys Gly Ser Ser Val Ile Asn Phe Glu Thr Ile Val Asn Lys Val
465                 470                 475                 480
```

```
ctc ttg gga aag atc cct aac acg taa                                 1467
Leu Leu Gly Lys Ile Pro Asn Thr
                485


<210> SEQ ID NO 30
<211> LENGTH: 488
<212> TYPE: PRT
<213> ORGANISM: Arabidopsis thaliana

<400> SEQUENCE: 30

Met Gly Ser Arg Phe Val Ser Asn Glu Gln Lys Pro His Val Val Cys
1               5                   10                  15

Val Pro Tyr Pro Ala Gln Gly His Ile Asn Pro Met Met Lys Val Ala
            20                  25                  30

Lys Leu Leu His Val Lys Gly Phe His Val Thr Phe Val Asn Thr Val
        35                  40                  45

Tyr Asn His Asn Arg Leu Leu Arg Ser Arg Gly Ala Asn Ala Leu Asp
    50                  55                  60

Gly Leu Pro Ser Phe Gln Phe Glu Ser Ile Pro Asp Gly Leu Pro Glu
65                  70                  75                  80

Thr Gly Val Asp Ala Thr Gln Asp Ile Pro Ala Leu Ser Glu Ser Thr
                85                  90                  95

Thr Lys Asn Cys Leu Val Pro Phe Lys Lys Leu Leu Gln Arg Ile Val
            100                 105                 110

Thr Arg Glu Asp Val Pro Pro Val Ser Cys Ile Val Ser Asp Gly Ser
        115                 120                 125

Met Ser Phe Thr Leu Asp Val Ala Glu Glu Leu Gly Val Pro Glu Ile
    130                 135                 140

His Phe Trp Thr Thr Ser Ala Cys Gly Phe Met Ala Tyr Leu His Phe
145                 150                 155                 160

Tyr Leu Phe Ile Glu Lys Gly Leu Cys Pro Val Lys Asp Ala Ser Cys
                165                 170                 175

Leu Thr Lys Glu Tyr Leu Asp Thr Val Ile Asp Trp Ile Pro Ser Met
            180                 185                 190

Asn Asn Val Lys Leu Lys Asp Ile Pro Ser Phe Ile Arg Thr Thr Asn
        195                 200                 205

Pro Asn Asp Ile Met Leu Asn Phe Val Val Arg Glu Ala Cys Arg Thr
    210                 215                 220

Lys Arg Ala Ser Ala Ile Ile Leu Asn Thr Phe Asp Asp Leu Glu His
225                 230                 235                 240

Asp Ile Ile Gln Ser Met Gln Ser Ile Leu Pro Pro Val Tyr Pro Ile
                245                 250                 255

Gly Pro Leu His Leu Leu Val Asn Arg Glu Ile Glu Glu Asp Ser Glu
            260                 265                 270

Ile Gly Arg Met Gly Ser Asn Leu Trp Lys Glu Glu Thr Glu Cys Leu
        275                 280                 285

Gly Trp Leu Asn Thr Lys Ser Arg Asn Ser Val Val Tyr Val Asn Phe
    290                 295                 300

Gly Ser Ile Thr Ile Met Thr Thr Ala Gln Leu Leu Glu Phe Ala Trp
305                 310                 315                 320

Gly Leu Ala Ala Thr Gly Lys Glu Phe Leu Trp Val Met Arg Pro Asp
                325                 330                 335

Ser Val Ala Gly Glu Glu Ala Val Ile Pro Lys Glu Phe Leu Ala Glu
            340                 345                 350

Thr Ala Asp Arg Arg Met Leu Thr Ser Trp Cys Pro Gln Glu Lys Val
```

```
        355                 360                 365

Leu Ser His Pro Ala Val Gly Gly Phe Leu Thr His Cys Gly Trp Asn
    370                 375                 380

Ser Thr Leu Glu Ser Leu Ser Cys Gly Val Pro Met Val Cys Trp Pro
385                 390                 395                 400

Phe Phe Ala Glu Gln Gln Thr Asn Cys Lys Phe Ser Cys Asp Glu Trp
                405                 410                 415

Glu Val Gly Ile Glu Ile Gly Gly Asp Val Lys Arg Gly Glu Val Glu
            420                 425                 430

Ala Val Val Arg Glu Leu Met Asp Gly Glu Lys Gly Lys Lys Met Arg
        435                 440                 445

Glu Lys Ala Val Glu Trp Arg Arg Leu Ala Glu Lys Ala Thr Lys Leu
    450                 455                 460

Pro Cys Gly Ser Ser Val Ile Asn Phe Glu Thr Ile Val Asn Lys Val
465                 470                 475                 480

Leu Leu Gly Lys Ile Pro Asn Thr
                485


<210> SEQ ID NO 31
<211> LENGTH: 1443
<212> TYPE: DNA
<213> ORGANISM: Antirrhinum majus
<220> FEATURE:
<221> NAME/KEY: CDS
<222> LOCATION: (1)..(1440)

<400> SEQUENCE: 31

atg ggt tcc aca gcc gaa aat aaa cag aaa acc cac att gtg tgc ata       48
Met Gly Ser Thr Ala Glu Asn Lys Gln Lys Thr His Ile Val Cys Ile
1               5                   10                  15

ccc tac cca gcc cag ggg cac atc agc ccc atg cta aag tta gcc aaa       96
Pro Tyr Pro Ala Gln Gly His Ile Ser Pro Met Leu Lys Leu Ala Lys
            20                  25                  30

ctg cta cac caa aac ggc ttt tac atc act ttt gtc aac acg gag tac      144
Leu Leu His Gln Asn Gly Phe Tyr Ile Thr Phe Val Asn Thr Glu Tyr
        35                  40                  45

aac cac cgc cgc ctc atc aag tcc cgc ggc ccc acc gcc ctc gac gga      192
Asn His Arg Arg Leu Ile Lys Ser Arg Gly Pro Thr Ala Leu Asp Gly
    50                  55                  60

ttg ccc gat ttc cgg ttc gtt acg atc ccc gac ggg ctt cct ttc tct      240
Leu Pro Asp Phe Arg Phe Val Thr Ile Pro Asp Gly Leu Pro Phe Ser
65                  70                  75                  80

gaa gcc gac gcc aca cag gat atc cct tct ctt tgt gtt tca acc acc      288
Glu Ala Asp Ala Thr Gln Asp Ile Pro Ser Leu Cys Val Ser Thr Thr
                85                  90                  95

aac act tgc ttg gag ccc ttt tgc gag ctg ctg tcg aac ctc aat aac      336
Asn Thr Cys Leu Glu Pro Phe Cys Glu Leu Leu Ser Asn Leu Asn Asn
            100                 105                 110

tcc ggc ccg gac gtg ccc ccg gtg agc tgc atc gta tcc gat ggt gtc      384
Ser Gly Pro Asp Val Pro Pro Val Ser Cys Ile Val Ser Asp Gly Val
        115                 120                 125

atg agc ttc acg ttg aag gcg gcg gag aga ttt ggg ctg ccg gag gtg      432
Met Ser Phe Thr Leu Lys Ala Ala Glu Arg Phe Gly Leu Pro Glu Val
    130                 135                 140

ctg ttc tgg acg acg agt gcg tgt ggg ttc ttg gcg tat acg cag tat      480
Leu Phe Trp Thr Thr Ser Ala Cys Gly Phe Leu Ala Tyr Thr Gln Tyr
145                 150                 155                 160

aag cat ctc gtg gag aaa ggc tat gta ccc ctc aaa gat atg agc caa      528
Lys His Leu Val Glu Lys Gly Tyr Val Pro Leu Lys Asp Met Ser Gln
```

-continued

```
                165                 170                 175

gta acg gat gga tat ttg aaa aca agc atg gac tgg att cca gga acg      576
Val Thr Asp Gly Tyr Leu Lys Thr Ser Met Asp Trp Ile Pro Gly Thr
            180                 185                 190

aag gac atc caa cta agg gac ttc ccc tct ttc atc agg aca aca gat      624
Lys Asp Ile Gln Leu Arg Asp Phe Pro Ser Phe Ile Arg Thr Thr Asp
        195                 200                 205

cca gaa gac atc atg ctt aat ttt tta ata caa gaa act gat gtt gtt      672
Pro Glu Asp Ile Met Leu Asn Phe Leu Ile Gln Glu Thr Asp Val Val
    210                 215                 220

ccg aga gcc aaa gct gta ata atc aac acc ttc gac atg tta gaa cac      720
Pro Arg Ala Lys Ala Val Ile Ile Asn Thr Phe Asp Met Leu Glu His
225                 230                 235                 240

gac gtc ctg gaa gcg ctc tcc acc atg ttt tca cgc gtt tac agc atc      768
Asp Val Leu Glu Ala Leu Ser Thr Met Phe Ser Arg Val Tyr Ser Ile
                245                 250                 255

ggc cct ctt cag ctg atg atg aat tat gtt cac aac gag tcc ctt aaa      816
Gly Pro Leu Gln Leu Met Met Asn Tyr Val His Asn Glu Ser Leu Lys
            260                 265                 270

tcc atc agt tcc agt cta tgg aaa gaa gaa aca cat tgc gtc gat tgg      864
Ser Ile Ser Ser Ser Leu Trp Lys Glu Glu Thr His Cys Val Asp Trp
        275                 280                 285

ctc gat tca aag gag ccc gaa tcc gtt gtg tac gta aat ttt ggc agc      912
Leu Asp Ser Lys Glu Pro Glu Ser Val Val Tyr Val Asn Phe Gly Ser
    290                 295                 300

ata act gtc gtg act gca gaa caa ctg act gag ttt gcg tgg ggg ctc      960
Ile Thr Val Val Thr Ala Glu Gln Leu Thr Glu Phe Ala Trp Gly Leu
305                 310                 315                 320

gct aat agt aag aag act ttc cta tgg gtt att agg cct gat ata gtt     1008
Ala Asn Ser Lys Lys Thr Phe Leu Trp Val Ile Arg Pro Asp Ile Val
                325                 330                 335

gct gga gac tcg gct atg ctg ccc cct gaa ttc gtg acg ggg aca aaa     1056
Ala Gly Asp Ser Ala Met Leu Pro Pro Glu Phe Val Thr Gly Thr Lys
            340                 345                 350

gat aga agc atg tta atc agc tgg tgt aac caa gaa cag gtg ttg aat     1104
Asp Arg Ser Met Leu Ile Ser Trp Cys Asn Gln Glu Gln Val Leu Asn
        355                 360                 365

cac cca tca att gga ggg ttt ttg acg cac agt ggt tgg aat tcg acg     1152
His Pro Ser Ile Gly Gly Phe Leu Thr His Ser Gly Trp Asn Ser Thr
    370                 375                 380

att gaa agt ata gtc gag gga gtt cct gtg att tgc tgg cct ttc ttt     1200
Ile Glu Ser Ile Val Glu Gly Val Pro Val Ile Cys Trp Pro Phe Phe
385                 390                 395                 400

gct gag cag caa aca aat tgt agg ttc agt tgc gtg gaa tgg gaa ata     1248
Ala Glu Gln Gln Thr Asn Cys Arg Phe Ser Cys Val Glu Trp Glu Ile
                405                 410                 415

gga atg gag att gat aat aat gtg aag aga gat gag gtt gaa gtt ttg     1296
Gly Met Glu Ile Asp Asn Asn Val Lys Arg Asp Glu Val Glu Val Leu
            420                 425                 430

gtg agg gaa ttg atg gat gga gag agg ggg aag aaa atg aag gag aaa     1344
Val Arg Glu Leu Met Asp Gly Glu Arg Gly Lys Lys Met Lys Glu Lys
        435                 440                 445

gct atg gag tgg aaa ggg aaa gca tta gag gca act gca ctt ggg ggc     1392
Ala Met Glu Trp Lys Gly Lys Ala Leu Glu Ala Thr Ala Leu Gly Gly
    450                 455                 460

tct tcc tac ttg aac ttg gaa aaa cta att aag gag gtg ctt ttg cat     1440
Ser Ser Tyr Leu Asn Leu Glu Lys Leu Ile Lys Glu Val Leu Leu His
465                 470                 475                 480

taa                                                                 1443
```

<210> SEQ ID NO 32
<211> LENGTH: 480
<212> TYPE: PRT
<213> ORGANISM: Antirrhinum majus

<400> SEQUENCE: 32

```
Met Gly Ser Thr Ala Glu Asn Lys Gln Lys Thr His Ile Val Cys Ile
1               5                   10                  15

Pro Tyr Pro Ala Gln Gly His Ile Ser Pro Met Leu Lys Leu Ala Lys
            20                  25                  30

Leu Leu His Gln Asn Gly Phe Tyr Ile Thr Phe Val Asn Thr Glu Tyr
        35                  40                  45

Asn His Arg Arg Leu Ile Lys Ser Arg Gly Pro Thr Ala Leu Asp Gly
    50                  55                  60

Leu Pro Asp Phe Arg Phe Val Thr Ile Pro Asp Gly Leu Pro Phe Ser
65                  70                  75                  80

Glu Ala Asp Ala Thr Gln Asp Ile Pro Ser Leu Cys Val Ser Thr Thr
                85                  90                  95

Asn Thr Cys Leu Glu Pro Phe Cys Glu Leu Leu Ser Asn Leu Asn Asn
            100                 105                 110

Ser Gly Pro Asp Val Pro Pro Val Ser Cys Ile Val Ser Asp Gly Val
        115                 120                 125

Met Ser Phe Thr Leu Lys Ala Ala Glu Arg Phe Gly Leu Pro Glu Val
    130                 135                 140

Leu Phe Trp Thr Thr Ser Ala Cys Gly Phe Leu Ala Tyr Thr Gln Tyr
145                 150                 155                 160

Lys His Leu Val Glu Lys Gly Tyr Val Pro Leu Lys Asp Met Ser Gln
                165                 170                 175

Val Thr Asp Gly Tyr Leu Lys Thr Ser Met Asp Trp Ile Pro Gly Thr
            180                 185                 190

Lys Asp Ile Gln Leu Arg Asp Phe Pro Ser Phe Ile Arg Thr Thr Asp
        195                 200                 205

Pro Glu Asp Ile Met Leu Asn Phe Leu Ile Gln Glu Thr Asp Val Val
    210                 215                 220

Pro Arg Ala Lys Ala Val Ile Ile Asn Thr Phe Asp Met Leu Glu His
225                 230                 235                 240

Asp Val Leu Glu Ala Leu Ser Thr Met Phe Ser Arg Val Tyr Ser Ile
                245                 250                 255

Gly Pro Leu Gln Leu Met Met Asn Tyr Val His Asn Glu Ser Leu Lys
            260                 265                 270

Ser Ile Ser Ser Ser Leu Trp Lys Glu Glu Thr His Cys Val Asp Trp
        275                 280                 285

Leu Asp Ser Lys Glu Pro Glu Ser Val Val Tyr Val Asn Phe Gly Ser
    290                 295                 300

Ile Thr Val Val Thr Ala Glu Gln Leu Thr Glu Phe Ala Trp Gly Leu
305                 310                 315                 320

Ala Asn Ser Lys Lys Thr Phe Leu Trp Val Ile Arg Pro Asp Ile Val
                325                 330                 335

Ala Gly Asp Ser Ala Met Leu Pro Pro Glu Phe Val Thr Gly Thr Lys
            340                 345                 350

Asp Arg Ser Met Leu Ile Ser Trp Cys Asn Gln Glu Gln Val Leu Asn
        355                 360                 365

His Pro Ser Ile Gly Gly Phe Leu Thr His Ser Gly Trp Asn Ser Thr
```

```
    370                 375                 380

Ile Glu Ser Ile Val Glu Gly Val Pro Val Ile Cys Trp Pro Phe Phe
385                 390                 395                 400

Ala Glu Gln Gln Thr Asn Cys Arg Phe Ser Cys Val Glu Trp Glu Ile
                405                 410                 415

Gly Met Glu Ile Asp Asn Asn Val Lys Arg Asp Glu Val Glu Val Leu
            420                 425                 430

Val Arg Glu Leu Met Asp Gly Glu Arg Gly Lys Lys Met Lys Glu Lys
        435                 440                 445

Ala Met Glu Trp Lys Gly Lys Ala Leu Glu Ala Thr Ala Leu Gly Gly
    450                 455                 460

Ser Ser Tyr Leu Asn Leu Glu Lys Leu Ile Lys Glu Val Leu Leu His
465                 470                 475                 480


<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33

cacccatatg ggatcccgtt ttgtttc                                           27


<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34

ctcgagttac gtgttaggga tctttc                                            26


<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35

cacccatatg ggatctcaga tcattcataa c                                      31


<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36

ggatccttaa tcctgtgatt tttgtcccaa aag                                    33


<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
      primer

<400> SEQUENCE: 37

tgtccaaaga ggcattttcc                                                  20


<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38

aaggatggca tgtccttgag                                                  20


<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

caactttcga tggtaggata gtg                                              23


<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

ggctatagac tcgttgaata catc                                             24
```

METHOD FOR USING HEXENOL GLYCOSYL TRANSFERASE

SEQUENCE LISTING

The instant application contains a Sequence Listing which has been submitted electronically in ASCII format and is hereby incorporated by reference in its entirety. Said ASCII copy, created on Jun. 14, 2016, is named P49209_SL.txt and is 184,000 bytes in size.

TECHNICAL FIELD

The present invention relates to a method for producing a hexenol glycoside, a transformant that highly expresses hexenol glycosyltransferase, as well as a hexenol glycoside produced by the above method and use thereof. The present invention also relates to a plant modified to suppress the expression of a protein having glycosylation activity on a hexenol compound and use thereof.

BACKGROUND ART

Green leaf volatiles (GLVs) typified by cis-3-hexenol are used to collectively refer to plant aroma components containing 6 carbon atoms, which constitute an aroma that is released from plants upon feeding damage and/or mechanical injury (Non-patent Document 1). Green leaf volatiles have repellent or attractive activity on insects or larvae thereof and are considered to be responsible for physiological roles as allelochemicals (Non-patent Document 2).

Green leaf volatiles are known to be generated by being liberated from linolenic acid in chloroplasts, although they are reported to be partially pooled within plant cells in the form of glycosides such as glucoside and primeveroside (Non-patent Document 3). These disaccharide glycosides including primeveroside are also known to be generated through a pathway where they are specifically hydrolyzed by the action of primeverosidase to release their aglycons, i.e., green leaf volatiles (Non-patent Document 4). However, there is no knowledge about enzymes and molecular mechanisms for glycosylation of green leaf volatiles and their accumulation within plant cells.

NON-PATENT DOCUMENTS

Non-patent Document 1: Matsui, K. (2006) *Current Opinion in Plant Biology* 9: 274-280

Non-patent Document 2: Arimura, G., et al. (2009) *Plant Cell Physiol.* 50: 911-923

Non-patent Document 3: Wang, D., et al. (2000) *J. Agric. Food Chem.* 48, 5411-5418

Non-patent Document 4: Mizutani, M. et al. (2002) *Plant Physiol.* 130: 2164-76

DISCLOSURE OF THE INVENTION

As a result of extensive and intensive efforts, the inventors of the present invention have succeeded in identifying enzymes catalyzing the glycosylation reaction of hexenol in *Camellia sinensis*, hop (*Humulus lupulus*), *stevia* (*Stevia rebaudiana*), grape (*Vitaceae vitis*), sweet potato (*Ipomoea batatas*), *Arabidopsis thaliana* and snapdragon (*Antirrhinum majus*), as well as gene sequences encoding these enzymes. The present invention is based on the above finding.

Namely, the present invention is as follows.

[1]

A method for producing a hexenol glycoside, which comprises the step of reacting a protein having glycosylation activity on hexenol with a UDP-sugar and a hexenol molecule to cause glycosylation of the hexenol molecule.

[2]

The method according to [1] above, wherein the protein is any one selected from the group consisting of (a) to (c) shown below:

(a) a protein which consists of the amino acid sequence shown in SEQ ID NO: 2 or 4;

(b) a protein which consists of an amino acid sequence with deletion, substitution, insertion and/or addition of 1 to 40 amino acids in the amino acid sequence shown in SEQ ID NO: 2 or 4 and which has glycosylation activity on hexenol; and (c) a protein which has an amino acid sequence sharing a sequence identity of 90% or more with the amino acid sequence shown in SEQ ID NO: 2 or 4 and which has glycosylation activity on hexenol.

[3]

The method according to [1] above, wherein the protein is any one selected from the group consisting of (d) to (f) shown below:

(d) a protein which consists of the amino acid sequence shown in SEQ ID NO: 6, 8, 10 or 12;

(e) a protein which consists of an amino acid sequence with deletion, substitution, insertion and/or addition of 1 to 40 amino acids in the amino acid sequence shown in SEQ ID NO: 6, 8, 10 or 12 and which has glycosylation activity on hexenol; and (f) a protein which has an amino acid sequence sharing a sequence identity of 90% or more with the amino acid sequence shown in SEQ ID NO: 6, 8, 10 or 12 and which has glycosylation activity on hexenol.

[4]

The method according to [1] above, wherein the protein is any one selected from the group consisting of (g) to (i) shown below:

(g) a protein which consists of the amino acid sequence shown in SEQ ID NO: 14, 16 or 18;

(h) a protein which consists of an amino acid sequence with deletion, substitution, insertion and/or addition of 1 to 40 amino acids in the amino acid sequence shown in SEQ ID NO: 14, 16 or 18 and which has glycosylation activity on hexenol; and (i) a protein which has an amino acid sequence sharing a sequence identity of 90% or more with the amino acid sequence shown in SEQ ID NO: 14, 16 or 18 and which has glycosylation activity on hexenol.

[5]

The method according to [1] above, wherein the protein is any one selected from the group consisting of (j) to (l) shown below:

(j) a protein which consists of the amino acid sequence shown in SEQ ID NO: 20, 22 or 24;

(k) a protein which consists of an amino acid sequence with deletion, substitution, insertion and/or addition of 1 to 40 amino acids in the amino acid sequence shown in SEQ ID NO: 20, 22 or 24 and which has glycosylation activity on hexenol; and (l) a protein which has an amino acid sequence sharing a sequence identity of 90% or more with the amino acid sequence shown in SEQ ID NO: 20, 22 or 24 and which has glycosylation activity on hexenol.

[6]

The method according to [1] above, wherein the protein is any one selected from the group consisting of (m) to (o) shown below:

(m) a protein which consists of the amino acid sequence shown in SEQ ID NO: 26;

(n) a protein which consists of an amino acid sequence with deletion, substitution, insertion and/or addition of 1 to 40 amino acids in the amino acid sequence shown in SEQ ID NO: 26 and which has glycosylation activity on hexenol; and (o) a protein which has an amino acid sequence sharing a sequence identity of 90% or more with the amino acid sequence shown in SEQ ID NO: 26 and which has glycosylation activity on hexenol.

[7]

The method according to [1] above, wherein the protein is any one selected from the group consisting of (p) to (r) shown below:

(p) a protein which consists of the amino acid sequence shown in SEQ ID NO: 28 or 30;

(q) a protein which consists of an amino acid sequence with deletion, substitution, insertion and/or addition of 1 to 40 amino acids in the amino acid sequence shown in SEQ ID NO: 28 or 30 and which has glycosylation activity on hexenol; and (r) a protein which has an amino acid sequence sharing a sequence identity of 90% or more with the amino acid sequence shown in SEQ ID NO: 28 or 30 and which has glycosylation activity on hexenol.

[8]

The method according to [1] above, wherein the protein is any one selected from the group consisting of (s) to (u) shown below:

(s) a protein which consists of the amino acid sequence shown in SEQ ID NO: 32;

(t) a protein which consists of an amino acid sequence with deletion, substitution, insertion and/or addition of 1 to 40 amino acids in the amino acid sequence shown in SEQ ID NO: 32 and which has glycosylation activity on hexenol; and (u) a protein which has an amino acid sequence sharing a sequence identity of 90% or more with the amino acid sequence shown in SEQ ID NO: 32 and which has glycosylation activity on hexenol.

[9]

The method according to [1] above, wherein the UDP-sugar is a UDP-hexose.

[10]

The method according to [9] above, wherein the hexose is selected from the group consisting of glucose, mannose and galactose.

[11]

The method according to any one of [1] to [10] above, wherein the protein is a recombinant protein generated by being expressed from a polynucleotide sequence encoding the protein in host cells.

[12]

The method according to [11] above, wherein the host cells are plant cells.

[13]

The method according to [11] or [12] above, wherein the step of causing glycosylation of the hexenol molecule is carried out in the host cells.

[14]

The method according to [13] above, which further comprises the step of purifying the hexenol glycoside from the host cells.

[15]

A composition for producing a hexenol glycoside, which comprises a protein having glycosylation activity on hexenol and a solvent.

[16]

The composition according to [15] above, wherein the protein is any one selected from the group consisting of (a) to (c) shown below:

(a) a protein which consists of the amino acid sequence shown in SEQ ID NO: 2 or 4;

(b) a protein which consists of an amino acid sequence with deletion, substitution, insertion and/or addition of 1 to 40 amino acids in the amino acid sequence shown in SEQ ID NO: 2 or 4 and which has glycosylation activity on hexenol; and (c) a protein which has an amino acid sequence sharing a sequence identity of 90% or more with the amino acid sequence shown in SEQ ID NO: 2 or 4 and which has glycosylation activity on hexenol.

[17]

A protein of any one selected from the group consisting of (v) to (x) shown below:

(v) a protein which consists of the amino acid sequence shown in SEQ ID NO: 16 or 18;

(w) a protein which consists of an amino acid sequence with deletion, substitution, insertion and/or addition of 1 to 40 amino acids in the amino acid sequence shown in SEQ ID NO: 16 or 18 and which has glycosylation activity on hexenol; and (x) a protein which has an amino acid sequence sharing a sequence identity of 90% or more with the amino acid sequence shown in SEQ ID NO: 16 or 18 and which has glycosylation activity on hexenol.

[18]

A polynucleotide encoding the protein according to [17] above.

The method or composition of the present invention enables the production of hexenol glycosides with high efficiency.

BRIEF DESCRIPTION OF THE DRAWINGS

FIG. 1 shows the hexenol glycosylation activity (LC-MS analysis results) of the negative control (pET15b/BL21: FIG. 1A), Cs_UGT_85Like_C1 (FIG. 1B) and Cs_UGT_C30 (FIG. 1C).

FIG. 2 shows the hexenol glycosylation activity (LC-MS analysis results) of Hl_UGT119 (FIG. 2A), Hl_UGT127 (FIG. 2B) and Hl_UGT279 (FIG. 2C).

FIG. 3 shows the hexenol glycosylation activity (LC-MS analysis results) of Hl_UGT251 (FIG. 3A), Ib_UGT42 (FIG. 3B) and Am_UGT207 (FIG. 3C).

FIG. 4 shows the hexenol glycosylation activity (LC-MS analysis results) of Sr_UGT85C2 (FIG. 4A), Sr_UGT85A5 (FIG. 4B) and Sr_UGT85C1 (FIG. 5C(4C?)).

FIG. 5 shows the hexenol glycosylation activity (LC-MS analysis results) of At_UGT85A1 (FIG. 5A), At_UGT85A3 (FIG. 5B) and the standard (cis-3-hexenyl glucopyranoside as a reference standard: FIG. 5C).

FIG. 6 shows the hexenol glycosylation activity (LC-MS analysis results) of Vv_UGT020 (FIG. 6A), Vv_UGT734 (FIG. 6B) and Vv_UGT744 (FIG. 6C).

BEST MODES FOR CARRYING OUT THE INVENTION

Figure 7:
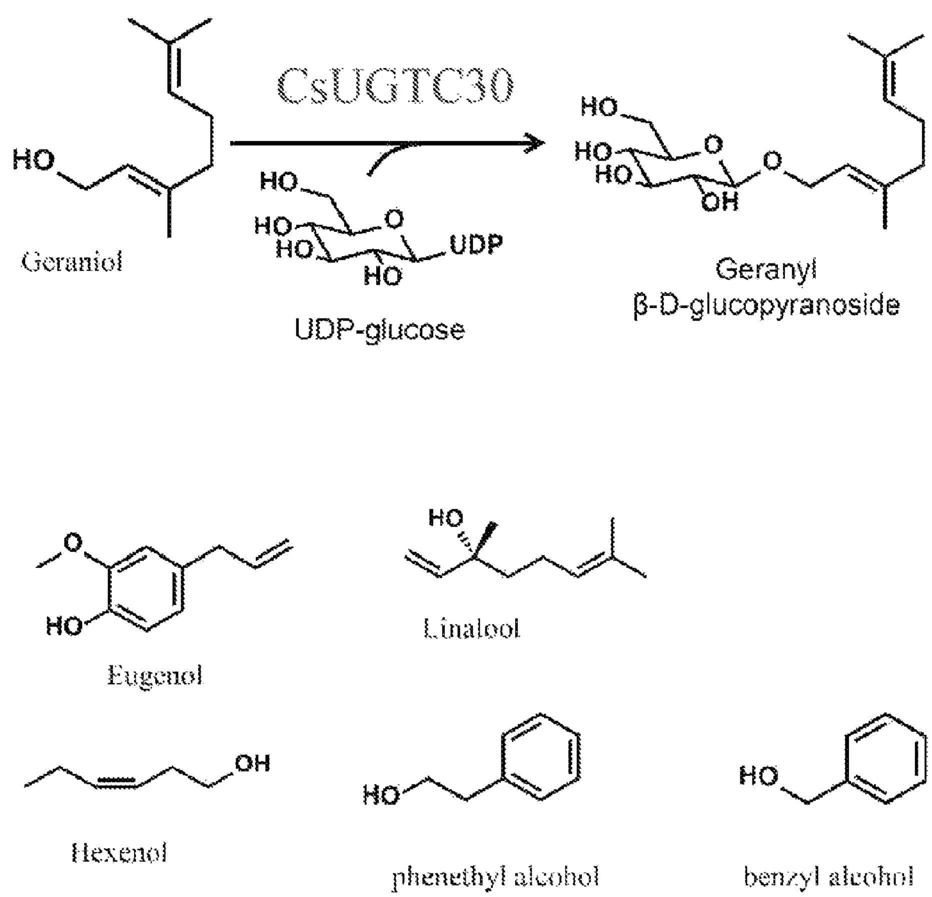
FIG. 7 shows the enzyme reaction catalyzed by CsUGTC30 (in which one molecule of glucose is added to geraniol to generate geranyl glucoside).

The present invention will be described in more detail below. The following embodiments are illustrated to describe the present invention, and it is not intended to limit the present invention only to these embodiments. The present invention can be implemented in various modes, without departing from the spirit of the present invention.

It should be noted that all publications cited herein, including prior art documents, patent gazettes and other patent documents, are incorporated herein by reference. Moreover, this specification incorporates the contents disclosed in the specification and drawings of Japanese Patent Application No. 2013-161579 (filed on Aug. 2, 2013), based on which the present application claims priority.

The inventors of the present invention have elucidated, ahead of others, that specific proteins have glycosylation activity on hexenol.

The amino acid sequences of the proteins identified by the inventors of the present invention and the CDS sequences of genes encoding these proteins are as shown in Table 1 below.

TABLE 1

| Species | Enzyme | CDS Sequence (SEQ ID NO:) | Amino Acid Sequence (SEQ ID NO:) |
|---|---|---|---|
| *Camellia sinensis* | Cs_UGT_C30 | 1 | 2 |
| (Cs) | Cs_UGT_85Like_C1 | 3 | 4 |
| *Humulus lupulus* | Hl_UGT119 | 5 | 6 |
| (Hl) | Hl_UGT127 | 7 | 8 |
| | Hl_UGT279 | 9 | 10 |
| | Hl_UGT251 | 11 | 12 |
| *Stevia rebaudiana* | Sr_UGT85C2 | 13 | 14 |
| (Sr) | Sr_UGT85A5 | 15 | 16 |
| | Sr_UGT85C1 | 17 | 18 |
| *Vitaceae vitis* | Vv_UGT020 | 19 | 20 |
| (Vv) | Vv_UGT734 | 21 | 22 |
| | Vv_UGT744 | 23 | 24 |
| *Ipomoea batatas* (Ib) | Ib_UGT42 | 25 | 26 |
| *Arabidopsis thaliana* | At_UGT85A1 | 27 | 28 |
| (At) | At_UGT85A3 | 29 | 30 |
| *Antirrhinum majus* (Am) | Am_UGT207 | 31 | 32 |

These polynucleotides and enzymes can be obtained by procedures as described later in the Example section, known genetic engineering procedures, known synthesis procedures, etc.

1. Method for Producing a Hexenol Glycoside

The present invention provides a method for producing a hexenol glycoside, which comprises the step of reacting a protein having glycosylation activity on hexenol (hereinafter referred to as "the protein of the present invention") with a UDP-sugar and a hexenol molecule to cause glycosylation of the hexenol molecule.

Moreover, the present invention also provides the use of the protein of the present invention in the production of hexenol glycosides.

Further, the present invention also provides the protein of the present invention for use in the production of hexenol glycosides.

The protein of the present invention is more specifically any one selected from the group consisting of (a) to (c) shown below:

(a) a protein which consists of the amino acid sequence shown in SEQ ID NO: 2, 4, 6, 8, 10, 12, 14, 16, 18, 20, 22, 24, 26, 28, 30 or 32;

(b) a protein which consists of an amino acid sequence with deletion, substitution, insertion and/or addition of 1 to 40 amino acids in the amino acid sequence shown in SEQ ID NO: 2, 4, 6, 8, 10, 12, 14, 16, 18, 20, 22, 24, 26, 28, 30 or 32 and which has glycosylation activity on hexenol; and (c) a protein which has an amino acid sequence sharing a sequence identity of 90% or more with the amino acid sequence shown in SEQ ID NO: 2, 4, 6, 8, 10, 12, 14, 16, 18, 20, 22, 24, 26, 28, 30 or 32 and which has glycosylation activity on hexenol.

In the above proteins (a) to (c), "the amino acid sequence shown in SEQ ID NO: 2, 4, 6, 8, 10, 12, 14, 16, 18, 20, 22, 24, 26, 28, 30 or 32" is intended in some embodiment to mean "the amino acid sequence shown in SEQ ID NO: 2 or 4," "the amino acid sequence shown in SEQ ID NO: 6, 8, 10 or 12," "the amino acid sequence shown in SEQ ID NO: 14, 16 or 18," "the amino acid sequence shown in SEQ ID NO: 20, 22 or 24," "the amino acid sequence shown in SEQ ID NO: 26," "the amino acid sequence shown in SEQ ID NO: 28 or 30" or "the amino acid sequence shown in SEQ ID NO: 32."

The above protein (b) or (c) is typically a mutant of the naturally occurring polypeptide shown in SEQ ID NO: 2, 4, 6, 8, 10, 12, 14, 16, 18, 20, 22, 24, 26, 28, 30 or 32, although other examples include those which may be artificially obtained by site-directed mutagenesis as described in "Sambrook & Russell, Molecular Cloning: A Laboratory Manual Vol. 3, Cold Spring Harbor Laboratory Press 2001," "Ausubel, Current Protocols in Molecular Biology, John Wiley & Sons 1987-1997," "Nuc. Acids. Res., 10, 6487 (1982)," "Proc. Natl. Acad. Sci. USA, 79, 6409 (1982)," "Gene, 34, 315 (1985)," "Nuc. Acids. Res., 13, 4431 (1985)," "Proc. Natl. Acad. Sci. USA, 82, 488 (1985)," etc.

As used herein, the expression "protein which consists of an amino acid sequence with deletion, substitution, insertion and/or addition of 1 to 40 amino acids in the amino acid sequence shown in SEQ ID NO: 2, 4, 6, 8, 10, 12, 14, 16, 18, 20, 22, 24, 26, 28, 30 or 32 and which has glycosylation activity on hexenol" is intended to include proteins which consist of an amino acid sequence with deletion, substitution, insertion and/or addition of, e.g., 1 to 40 amino acid residues, 1 to 39 amino acid residues, 1 to 38 amino acid residues, 1 to 37 amino acid residues, 1 to 36 amino acid residues, 1 to 35 amino acid residues, 1 to 34 amino acid residues, 1 to 33 amino acid residues, 1 to 32 amino acid residues, 1 to 31 amino acid residues, 1 to 30 amino acid residues, 1 to 29 amino acid residues, 1 to 28 amino acid residues, 1 to 27 amino acid residues, 1 to 26 amino acid residues, 1 to 25 amino acid residues, 1 to 24 amino acid residues, 1 to 23 amino acid residues, 1 to 22 amino acid residues, 1 to 21 amino acid residues, 1 to 20 amino acid residues, 1 to 19 amino acid residues, 1 to 18 amino acid residues, 1 to 17 amino acid residues, 1 to 16 amino acid residues, 1 to 15 amino acid residues, 1 to 14 amino acid residues, 1 to 13 amino acid residues, 1 to 12 amino acid residues, 1 to 11 amino acid residues, 1 to 10 amino acid residues, 1 to 9 amino acid residues (1 to several amino acid residues), 1 to 8 amino acid residues, 1 to 7 amino acid residues, 1 to 6 amino acid residues, 1 to 5 amino acid residues, 1 to 4 amino acid residues, 1 to 3 amino acid residues, 1 to 2 amino acid residues, or a single amino acid residue in the amino acid sequence shown in SEQ ID NO: 2, 4, 6, 8, 10, 12, 14, 16, 18, 20, 22, 24, 26, 28, 30 or 32 and which have glycosylation activity on hexenol. In general, a smaller number is more preferred for the above deletion, substitution, insertion and/or addition of amino acid residues.

Moreover, examples of such proteins include those which have an amino acid sequence sharing a sequence identity of 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with the amino acid sequence shown in SEQ ID NO: 2, 4, 6, 8, 10, 12, 14, 16, 18, 20, 22, 24, 26, 28, 30 or 32 and which have glycosylation activity on hexenol. In general, a larger value is more preferred for the above sequence identity.

In the context of the present invention, the expression "glycosylation activity on hexenol" is intended to mean the ability to add a sugar included in a UDP-sugar to a hydroxy group (—OH group) in hexenol serving as an aglycon (i.e., glycosylation). There is no particular limitation on the position of the hydroxy group where sugar addition occurs.

Glycosylation activity on hexenol can be confirmed by reacting the protein of the present invention with a UDP-sugar and a hexenol molecule to detect a hexenol glycoside.

In this case, the reaction of the protein of the present invention with a UDP-sugar and a hexenol molecule may be conducted by incubation at a temperature of 20° C. to 40° C. in a system (preferably a neutral buffer of pH 6.0 to 8.0 (e.g., sodium phosphate buffer or potassium phosphate buffer)) which contains the protein of the present invention in an amount of 1 to 500 ng (preferably 50 to 200 ng, most preferably 100 ng), a UDP-sugar (e.g., UDP-glucose) at 1 to 1000 μM (preferably 100 to 700 μM, most preferably 500 μM) and hexenol (e.g., cis-3-hexenol) at 1 to 500 μM (preferably 100 to 500 μM, most preferably 250 μM). Glycosylation reaction is normally completed within about 1 minute to about 12 hours.

Moreover, to detect a hexenol glycoside, the above hexenol may be purified and analyzed by known procedures such as LC-MS analysis (liquid chromatography-mass spectrometry), etc. Namely, if the purified hexenol shows a glycoside peak, it can be determined that hexenol was glycosylated by the activity of the protein of the present invention.

In addition, the protein of the present invention, particularly those shown below have glycosylation activity not only on hexenol, but also on geraniol, eugenol, benzyl alcohol, 2-phenylethanol and linalool (FIG. 7):

(v) a protein which consists of the amino acid sequence shown in SEQ ID NO: 2;

(w) a protein which consists of an amino acid sequence with deletion, substitution, insertion and/or addition of 1 to 40 amino acids in the amino acid sequence shown in SEQ ID NO: 2 and which has glycosylation activity on any one or more substrates selected from the group consisting of hexenol, geraniol, eugenol, benzyl alcohol, 2-phenylethanol and linalool; and (x) a protein which has an amino acid sequence sharing a sequence identity of 90% or more with the amino acid sequence shown in SEQ ID NO: 2 and which has glycosylation activity on any one or more substrates selected from the group consisting of hexenol, geraniol, eugenol, benzyl alcohol, 2-phenylethanol and linalool.

The above proteins (w) and (x) are equivalent to proteins (b') and (c') shown below, respectively:

(b') a protein which consists of an amino acid sequence with deletion, substitution, insertion and/or addition of 1 to 40 amino acids in the amino acid sequence shown in SEQ ID NO: 2 and which has glycosylation activity on hexenol; and (c') a protein which has an amino acid sequence sharing a sequence identity of 90% or more with the amino acid sequence shown in SEQ ID NO: 2 and which has glycosylation activity on hexenol.

Thus, the present invention also provides a method for glycosylation of any one or more substrates selected from the group consisting of hexenol, geraniol, eugenol, benzyl alcohol, 2-phenylethanol and linalool.

In the context of the present invention, the expression "glycosylation activity on any one or more substrates selected from the group consisting of hexenol, geraniol, eugenol, benzyl alcohol, 2-phenylethanol and linalool" is intended to mean the ability to add a sugar included in a UDP-sugar to a hydroxy group (—OH group) in any one or more substrates selected from the group consisting of geraniol, eugenol, benzyl alcohol, 2-phenylethanol and linalool (hereinafter referred to as "the substrate of the present invention") being in an aglycon state (i.e., glycosylation). There is no particular limitation on the position of the hydroxy group where sugar addition occurs.

Glycosylation activity of the present invention on its substrate can be confirmed by reacting the protein of the present invention with a UDP-sugar and the substrate molecule of the present invention and detecting a hexenol glycoside.

In this case, the reaction of the protein of the present invention with a UDP-sugar and the substrate molecule of the present invention may be conducted by incubation at a temperature of 20° C. to 40° C. in a system (preferably a neutral buffer of pH 6.0 to 8.0 (e.g., sodium phosphate buffer or potassium phosphate buffer)) which contains the protein of the present invention in an amount of 1 to 500 ng (preferably 50 to 200 ng, most preferably 100 ng), a UDP-sugar (e.g., UDP-glucose) at 1 to 1000 PA (preferably 100 to 700 μM, most preferably 500 μM) and the substrate of the present invention at 1 to 500 μM (preferably 100 to 500 μM, most preferably 250 μM). Glycosylation reaction is normally completed within about 1 minute to about 12 hours.

Moreover, to detect a glycoside of the substrate of the present invention, the above substrate may be purified and analyzed by known procedures such as LC-MS analysis (liquid chromatography-mass spectrometry), etc. Namely, if the purified substrate of the present invention shows a glycoside peak, it can be determined that the substrate of the present invention was glycosylated by the activity of the protein of the present invention.

Deletion, substitution, insertion and/or addition of one or several amino acid residues in the amino acid sequence of the protein of the present invention is intended to mean that deletion, substitution, insertion and/or addition of one or several amino acid residues occurs at any one or more positions in the same sequence, and two or more of deletion, substitution, insertion and addition may occur at the same time.

Examples of interchangeable amino acid residues are shown below. Amino acid residues included in the same group are interchangeable with each other. Group A: leucine, isoleucine, norleucine, valine, norvaline, alanine, 2-aminobutanoic acid, methionine, o-methylserine, t-butylglycine, t-butylalanine, cyclohexylalanine; Group B: aspartic acid, glutamic acid, isoaspartic acid, isoglutamic acid, 2-aminoadipic acid, 2-aminosuberic acid; Group C: asparagine, glutamine; Group D: lysine, arginine, ornithine, 2,4-diaminobutanoic acid, 2,3-diaminopropionic acid; Group E: proline, 3-hydroxyproline, 4-hydroxyproline; Group F: serine, threonine, homoserine; Group G: phenylalanine, tyrosine.

Although the protein of the present invention may be obtained by being expressed from a polynucleotide encoding it (see "the polynucleotide of the present invention" described later) in appropriate host cells, it may also be prepared by chemical synthesis methods such as Fmoc method (fluorenylmethyloxycarbonyl method) and tBoc method (t-butyloxycarbonyl method). Alternatively, the protein of the present invention may also be chemically synthesized with peptide synthesizers commercially available from Advanced Automation Peptide Protein Technologies, Perkin Elmer, Protein Technologies, PerSeptive, Applied Biosystems, SHIMADZU, etc.

In the context of the present invention, the term "hexenol" refers to hexene substituted with one or more —OH groups (molecular formula: $C_6H_{12}O$). In this case, the hexene skeleton may be in any form, i.e., linear, branched or cyclic, preferably linear. Moreover, hexenol may have a carbon-carbon double bond at any position, although it preferably has a double bond between the carbon at the 3-position and the carbon at the 4-position. The hexene skeleton may be in either cis- or trans-configuration. In hexenol, the number of —OH groups is preferably 1. Moreover, the —OH group is preferably attached to the terminal carbon atom of the linear or branched hexene skeleton, more preferably attached to the terminal carbon atom of the linear hexene skeleton. Specific examples of hexenol include, but are not limited to, cis-3-hexenol (cis-3-hexen-1-ol) and trans-2-hexenol (trans-2-hexen-1-ol).

In the context of the present invention, the term "hexenol" is used interchangeably with "leaf alcohol" in some cases. Specific examples of leaf alcohol include cis-3-hexenol and trans-2-hexenol (trans-2-hexen-1-ol).

In the context of the present invention, "benzyl alcohol" is also referred to as phenylmethanol.

In the context of the present invention, the term "2-phenylethanol" refers to a compound which is also referred to as phenethyl alcohol, benzyl carbinol, β-hydroxyethylbenzene, β-phenylethyl alcohol, phenethanol, phenylethyl alcohol, β-phenethyl alcohol, β-phenylethanol, β-phenethanol, phenylethanol, 2-phenethanol or α-phenethylol.

In the context of the present invention, the term "UDP-sugar" refers to a uridine diphosphate (UDP)-conjugated sugar, preferably a UDP-conjugated hexose (UDP-hexose). Examples include, but are not limited to, UDP-glucose, UDP-mannose and UDP-galactose. A preferred UDP-sugar is UDP-glucose.

The term "hexenol glycoside" is intended to mean hexenol having a sugar (derived from a UDP-sugar) added to at least one or more —OH groups.

For example, when cis-3-hexenol is reacted with UDP-glucose in the presence of the protein of the present invention, cis-3-hexenyl monoglucoside is generated as a hexenol glycoside (see the reaction scheme shown below).

[Formula 1]

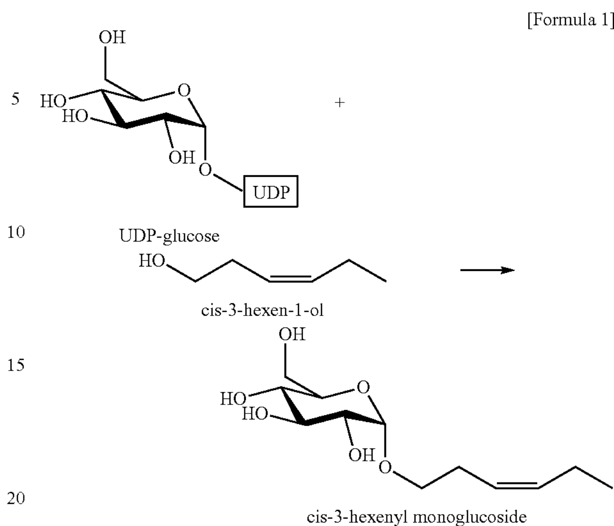

The method of the present invention for producing a hexenol glycoside comprises the step of reacting the protein of the present invention with a UDP-sugar and hexenol to cause glycosylation of the hexenol. The method of the present invention may further comprise the step of purifying the hexenol glycoside generated in the above step.

The hexenol glycoside can be purified by known techniques such as extraction with an appropriate solvent (an aqueous solvent such as water or an organic solvent such as alcohol, ether or acetone), a gradient between an organic solvent (e.g., ethyl acetate) and water, high performance liquid chromatography (HPLC), gas chromatography, time-of-flight mass spectrometry (TOF-MS), ultra (high) performance liquid chromatography (UPLC), etc.

Likewise, a glycoside of the substrate of the present invention is intended to mean the substrate of the present invention having a sugar (derived from a UDP-sugar) added to at least one or more —OH groups.

A method for producing a glycoside of the substrate of the present invention comprises the step of reacting the protein of the present invention with a UDP-sugar and the substrate of the present invention to cause glycosylation of the hexenol (substrate?). The method of the present invention may further comprise the step of purifying the glycoside of the substrate of the present invention generated in the above step.

The glycoside of the substrate of the present invention can be purified by known techniques such as extraction with an appropriate solvent (an aqueous solvent such as water or an organic solvent such as alcohol, ether or acetone), a gradient between an organic solvent (e.g., ethyl acetate) and water, high performance liquid chromatography (HPLC), gas chromatography, time-of-flight mass spectrometry (TOF-MS), ultra (high) performance liquid chromatography (UPLC), etc.

2. Non-Human Transformant Rich in Hexenol Glycosides

Hexenol glycosides may also be produced using the protein of the present invention within cells such as those of bacteria (e.g., *E. coli* or yeast), plants, insects, non-human mammals, etc. In this case, a polynucleotide encoding the protein of the present invention (see "the polynucleotide of the present invention" described later) may be introduced into host cells derived from bacteria, plants, insects, non-human mammals or the like to cause expression of the protein of the present invention, followed by reacting the protein of the present invention with UDP-sugars and hexenol present within the above cells to produce hexenol glycosides. Namely, in this embodiment, the protein of the present invention is a recombinant protein generated by being expressed from a polynucleotide sequence encoding the protein in host cells.

A non-human transformant obtained by introduction of a gene encoding the protein of the present invention is expected to be rich in hexenol glycosides when compared to the wild-type counterpart.

The present invention therefore provides a non-human transformant transformed with a polynucleotide of any one selected from the group consisting of (a) to (e) shown below (hereinafter referred to as "the polynucleotide of the present invention") (such a transformant is hereinafter referred to as "the transformant of the present invention"):

(a) a polynucleotide containing the nucleotide sequence shown in SEQ ID NO: 1, 3, 5, 7, 9, 11, 13, 15, 17, 19, 21, 23, 25, 27, 29 or 31;

(b) a polynucleotide encoding a protein which consists of the amino acid sequence shown in SEQ ID NO: 2, 4, 6, 8, 10, 12, 14, 16, 18, 20, 22, 24, 26, 28, 30 or 32;

(c) a polynucleotide encoding a protein which consists of an amino acid sequence with deletion, substitution, insertion and/or addition of 1 to 40 amino acids in the amino acid sequence shown in SEQ ID NO: 2, 4, 6, 8, 10, 12, 14, 16, 18, 20, 22, 24, 26, 28, 30 or 32 and which has glycosylation activity on hexenol;

(d) a polynucleotide encoding a protein which has an amino acid sequence sharing a sequence identity of 90% or more with the amino acid sequence shown in SEQ ID NO: 2, 4 or 6 and which has glycosylation activity on hexenol; and (e) a polynucleotide which is hybridizable under high stringent conditions with a polynucleotide consisting of a nucleotide sequence complementary to the nucleotide sequence shown in SEQ ID NO: 1, 3, 5, 7, 9, 11, 13, 15, 17, 19, 21, 23, 25, 27, 29 or 31 and which encodes a protein having glycosylation activity on hexenol.

In the above polynucleotides (a) and (e), "the nucleotide sequence shown in SEQ ID NO: 1, 3, 5, 7, 9, 11, 13, 15, 17, 19, 21, 23, 25, 27, 29 or 31" is intended in some embodiment to mean "the nucleotide sequence shown in SEQ ID NO: 1 or 3," "the nucleotide sequence shown in SEQ ID NO: 5, 7, 9 or 11," "the nucleotide sequence shown in SEQ ID NO: 13, 15 or 17," "the nucleotide sequence shown in SEQ ID NO: 19, 21 or 23," "the nucleotide sequence shown in SEQ ID NO: 25," "the nucleotide sequence shown in SEQ ID NO: 27 or 29" or "the nucleotide sequence shown in SEQ ID NO: 31."

In the above polynucleotides (b) to (d), "the amino acid sequence shown in SEQ ID NO: 2, 4, 6, 8, 10, 12, 14, 16, 18, 20, 22, 24, 26, 28, 30 or 32" is intended in some embodiment to mean "the amino acid sequence shown in SEQ ID NO: 2 or 4," "the amino acid sequence shown in SEQ ID NO: 6, 8, 10 or 12," "the amino acid sequence shown in SEQ ID NO: 14, 16 or 18," "the amino acid sequence shown in SEQ ID NO: 20, 22 or 24," "the amino acid sequence shown in SEQ ID NO: 26," "the amino acid sequence shown in SEQ ID NO: 28 or 30" or "the amino acid sequence shown in SEQ ID NO: 32."

The polynucleotide of the present invention also includes polynucleotides shown below:

(f) a polynucleotide containing the nucleotide sequence shown in SEQ ID NO: 1;

(g) a polynucleotide encoding a protein which consists of the amino acid sequence shown in SEQ ID NO: 2;

(h) a polynucleotide encoding a protein which consists of an amino acid sequence with deletion, substitution, insertion and/or addition of 1 to 40 amino acids in the amino acid sequence shown in SEQ ID NO: 2 and which has glycosylation activity on any one or more substrates selected from the group consisting of hexenol, geraniol, eugenol, benzyl alcohol, 2-phenylethanol and linalool;

(i) a polynucleotide encoding a protein which has an amino acid sequence sharing a sequence identity of 90% or more with the amino acid sequence shown in SEQ ID NO: 2 and which has glycosylation activity on any one or more substrates selected from the group consisting of hexenol, geraniol, eugenol, benzyl alcohol, 2-phenylethanol and linalool; and (j) a polynucleotide which is hybridizable under high stringent conditions with a polynucleotide consisting of a nucleotide sequence complementary to the nucleotide sequence shown in SEQ ID NO: 1 and which encodes a protein having glycosylation activity on any one or more substrates selected from the group consisting of hexenol, geraniol, eugenol, benzyl alcohol, 2-phenylethanol and linalool.

As used herein, the term "polynucleotide" is intended to mean DNA or RNA.

As used herein, the expression "polynucleotide which is hybridizable under high stringent conditions" is intended to mean, for example, a polynucleotide that can be obtained by means of colony hybridization, plaque hybridization, Southern hybridization or other hybridization techniques using, as a probe, the whole or a part of a polynucleotide consisting of a nucleotide sequence complementary to the nucleotide sequence shown in SEQ ID NO: 1, 3, 5, 7, 9, 11, 13, 15, 17, 19, 21, 23, 25, 27, 29 or 31 or of a polynucleotide consisting of a nucleotide sequence encoding the amino acid sequence shown in SEQ ID NO: 2, 4, 6, 8, 10, 12, 14, 16, 18, 20, 22, 24, 26, 28, 30 or 32. For hybridization, it is possible to use techniques as described in, e.g., "Sambrook & Russell, Molecular Cloning: A Laboratory Manual Vol. 3, Cold Spring Harbor, Laboratory Press 2001" and "Ausubel, Current Protocols in Molecular Biology, John Wiley & Sons 1987-1997."

As used herein, the term "high stringent conditions" refers to, for example, but is not limited to, conditions of (1) 5×SSC, 5×Denhardt's solution, 0.5% SDS, 50% formamide, 50° C., (2) 0.2×SSC, 0.1% SDS, 60° C., (3) 0.2×SSC, 0.1% SDS, 62° C., (4) 0.2×SSC, 0.1% SDS, 65° C., or (5) 0.1×SSC, 0.1% SDS, 65° C. Under these conditions, it can be expected that DNA having a higher sequence identity is efficiently obtained at a higher temperature. However, the stringency of hybridization would be affected by a plurality of factors, including temperature, probe concentration, probe length, ionic strength, reaction time, salt concentration and so on. Those skilled in the art would be able to achieve the same stringency by selecting these factors as appropriate.

It should be noted that if a commercially available kit is used for hybridization, an Alkphos Direct Labelling and Detection System (GE Healthcare) may be used for this purpose, by way of example. In this case, hybridization may be accomplished in accordance with the protocol attached to the kit, i.e., a membrane may be incubated overnight with a labeled probe and then washed with a primary washing buffer containing 0.1% (w/v) SDS under conditions of 55° C. to 60° C. to detect the hybridized DNA. Alternatively, if a commercially available reagent (e.g., PCR labeling mix (Roche Diagnostics)) is used for digoxigenin (DIG) labeling of a probe during probe preparation based on the whole or a part of a nucleotide sequence complementary to the nucleotide sequence shown in SEQ ID NO: 1, 3, 5, 7, 9, 11, 13, 15, 17, 19, 21, 23, 25, 27, 29 or 31 or of a nucleotide sequence encoding the amino acid sequence shown in SEQ ID NO: 2, 4, 6, 8, 10, 12, 14, 16, 18, 20, 22, 24, 26, 28, 30 or 32, a DIG nucleic acid detection kit (Roche Diagnostics) may be used for detection of hybridization.

In addition to those listed above, other hybridizable polynucleotides include DNAs sharing a sequence identity of 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with DNA consisting of the nucleotide sequence shown in SEQ ID NO: 1, 3, 5, 7, 9, 11, 13, 15, 17, 19, 21, 23, 25, 27, 29 or 31 or with DNA encoding the amino acid sequence shown in SEQ ID NO: 2, 4, 6, 8, 10, 12, 14, 16, 18, 20, 22, 24, 26, 28, 30 or 32, as calculated by homology search software such as FASTA or BLAST using default parameters.

It should be noted that the sequence identity of amino acid sequences or nucleotide sequences can be determined by using FASTA (Science 227 (4693): 1435-1441, (1985)) or the algorithm of Karlin and Altschul, BLAST (Basic Local Alignment Search Tool) (Proc. Natl. Acad. Sci. USA 872264-2268, 1990; Proc Natl Acad Sci USA 90: 5873, 1993). Based on the algorithm of BLAST, programs called blastn, blastx, blastp, tblastn and tblastx have been developed (Altschul S F, et al.: J Mol Biol 215: 403, 1990). If blastn is used for nucleotide sequence analysis, parameters may be set to, for example, score=100 and wordlength=12. Likewise, if blastp is used for amino acid sequence analysis, parameters may be set to, for example, score=50 and wordlength=3. If BLAST and Gapped BLAST programs are used, default parameters in each program may be used.

The above polynucleotides according to the present invention can be obtained by known genetic engineering procedures or known synthesis procedures.

The polynucleotide of the present invention is preferably introduced into a host in a state of being inserted into an appropriate expression vector.

An appropriate expression vector is generally configured to comprise:

(i) a promoter transcribable in host cells;

(ii) the polynucleotide of the present invention ligated to the promoter; and (iii) an expression cassette comprising, as constituent elements, signals that function in the host cells for transcription termination and polyadenylation of an RNA molecule.

Such an expression vector may be prepared in any manner, for example, by techniques using plasmids, phages or cosmids, etc.

The actual type of vector is not limited in any way, and any vector expressible in host cells may be selected as appropriate. Namely, a promoter sequence may be selected as appropriate for the type of host cells in order to ensure expression of the polynucleotide of the present invention, and this promoter and the polynucleotide of the present invention may then be integrated into various plasmids or the like for use as expression vectors.

The expression vector of the present invention contains an expression control region(s) (e.g., a promoter, a terminator and/or a replication origin), depending on the type of host into which the expression vector is to be introduced. Promoters for use in bacterial expression vectors may be commonly used promoters (e.g., trc promoter, tac promoter, lac promoter). Likewise, promoters for use in yeast include, for example, glyceraldehyde triphosphate dehydrogenase promoter, PHO5 promoter and so on, while promoters for use in filamentous fungi include, for example, amylase, trpC and so on. In addition, examples of promoters used to express a desired gene in plant cells include cauliflower mosaic virus 35S RNA promoter, rd29A gene promoter, rbcS promoter, and mac-1 promoter that is configured to have the enhancer sequence of the above cauliflower mosaic virus 35S RNA promoter at the 5'-side of *Agrobacterium*-derived mannopine synthase promoter sequence.

The expression vector preferably comprises at least one selection marker. For this purpose, drug resistance markers (hygromycine, zeocin), geneticin resistance gene (G418r), herbicide resistance gene (SurB), copper resistance gene (CUP 1) (Marin et al., Proc. Natl. Acad. Sci. USA, vol. 81, p. 337, 1984), cerulenin resistance genes (fas2m, PDR4) (Junji Inokoshi et al., Biochemistry, vol. 64, p. 660, 1992; Hussain et al., Gene, vol. 101, p. 149, 1991) and so on are available for use.

Although the transformant of the present invention may be prepared (produced) in any manner, an expression vector comprising the polynucleotide of the present invention may be introduced into a host to transform the host, by way of example. Host cells used for this purpose may be of any type, and conventionally known various types of cells can be used preferably. Specific examples include bacteria such as *E. coli*, yeast (budding yeast *Saccharomyces cerevisiae*, fission yeast *Schizosaccharomyces pombe*) and plant cells, etc.

Culture media and conditions appropriate for the above host cells are well known in the art. Moreover, the organism to be transformed may be of any type, and examples include various types of microorganisms or plants as listed above for host cells.

For transformation of host cells, commonly used known techniques can be used. For example, transformation may be accomplished by, but is not limited to, electroporation (Mackenxie, D. A. et al., Appl. Environ. Microbiol., vol. 66, p. 4655-4661, 2000), particle delivery method (described in JP 2005-287403 A entitled "Breeding Method of Lipid Producing Fungi"), spheroplast method (Proc. Natl. Acad. Sci. USA, vol. 75, p. 1929, 1978), lithium acetate method (J. Bacteriology, vol. 153, p. 163, 1983), and other methods as described in Methods in yeast genetics, 2000 Edition: A Cold Spring Harbor Laboratory Course Manual.

In addition, as for standard molecular biological procedures, reference may be made to "Sambrook & Russell, Molecular Cloning: A Laboratory Manual Vol. 3, Cold Spring Harbor Laboratory Press 2001," "Methods in Yeast Genetics, A laboratory manual (Cold Spring Harbor Laboratory Press, Cold Spring Harbor, N.Y.)," etc.

In one embodiment of the present invention, the transformant may be a plant transformant. The plant transformant according to this embodiment may be obtained by introducing a recombinant vector comprising the polynucleotide of the present invention into a plant such that a polypeptide encoded by this polynucleotide can be expressed.

In cases where a recombinant expression vector is used, any recombinant expression vector may be used for transformation of a whole plant as long as it is a vector allowing the polynucleotide of the present invention to be expressed within the plant. Examples of such a vector include those having a promoter which drives constitutive expression of a desired polynucleotide within plant cells or those having a promoter whose activation is induced by external stimulation.

Examples of a promoter which drives constitutive expression of a desired polynucleotide within plant cells include cauliflower mosaic virus 35S RNA promoter, rd29A gene promoter, rbcS promoter, mac-1 promoter, etc.

Examples of a promoter whose activation is induced by external stimulation include mouse mammary tumor virus (MMTV) promoter, tetracycline-responsive promoter, metallothionein promoter and heat shock protein promoter, etc. In particular, to drive inducible expression of a desired polynucleotide within plant cells upon external stimulation, it is possible to use a stress-inducible promoter, a high temperature- or low temperature-inducible promoter, etc. Moreover, to drive expression of a desired polynucleotide specifically in a certain organ of the whole plant, it is possible to use a promoter for a gene specifically expressed in the intended organ.

The plant to be transformed in the present invention is intended to mean any of a whole plant, a plant organ (e.g., leaf, petal, stem, root, seed), a plant tissue (e.g., epidermis, phloem, parenchyma, xylem, vascular bundle, palisade tissue, spongy parenchyma) or a plant cultured cell, or alternatively, various forms of plant cells (e.g., suspension cultured cells), a protoplast, a leaf section, a callus and so on. The plant used for transformation may be of any type, belonging to either monocotyledons or dicotyledons.

For gene transfer into plants, transformation techniques known to those skilled in the art may be used (e.g., *Agrobacterium*-mediated method, gene gun method, PEG-mediated method, electroporation). For example, *Agrobacterium*-mediated method and direct gene transfer into plant cells are well known. In the case of using the *Agrobacterium*-mediated method, the constructed plant expression vector may be introduced into an appropriate *Agrobacterium* strain (e.g., *Agrobacterium tumefaciens*) and this strain may then be infected into a leaf section cultured under sterile conditions, e.g., in accordance with the leaf disk method (Hirofumi Miyauchi, Manuals for Plant Genetic Engineering (1990) pages 27-31, Kodansha Scientific Ltd., Tokyo) to thereby obtain a transgenic plant. Alternatively, it is possible to use the method of Nagel et al. (Micribiol. Lett., 67: 325 (1990)). In this method, for example, an expression vector is first introduced into *Agrobacterium*, and the transformed *Agrobacterium* is then introduced into plant cells or plant tissues as described in Plant Molecular Biology Manual (Gelvin, S. B. et al., Academic Press Publishers). As used herein, the term "plant tissue" also includes a callus obtainable by culturing plant cells. In cases where the *Agrobacterium*-mediated method is used for transformation, a binary vector (e.g., pBI121 or pPZP202) may be used.

Likewise, techniques known for direct gene transfer into plant cells or plant tissues are electroporation and particle gun method. In the case of using a particle gun, a whole plant, a plant organ or a plant tissue may be used directly, or sections may be prepared therefrom before use, or protoplasts may be prepared and used. The thus prepared samples may be treated using a gene transfer device (e.g., PDS-1000 (BIO-RAD)). Although treatment conditions will vary depending on the type of plant or sample, the treatment is generally conducted at a pressure of about 450 to 2000 psi and at a distance of about 4 to 12 cm.

The transformed cells or plant tissues are first selected by drug resistance such as hygromycin resistance, and then regenerated into whole plants in a standard manner. Regeneration from transformed cells into whole plants may be accomplished by techniques known to those skilled in the art as appropriate for the type of plant cells.

In cases where cultured plant cells are used as a host, transformation may be accomplished by introducing a recombinant vector into the cultured cells with a gene gun or by electroporation, etc. Calli, shoots, hairy roots and the like obtained as a result of transformation may be used directly for cell culture, tissue culture or organ culture, and may also be regenerated into whole plants using conventionally known procedures for plant tissue culture, e.g., by being administered with an appropriate concentration of a plant hormone (e.g., auxin, cytokinin, gibberellin, abscisic acid, ethylene, brassinolide).

Confirmation of whether or not the polynucleotide of the present invention has been introduced into a plant may be accomplished by PCR, Southern hybridization, Northern hybridization, etc. For example, DNA is prepared from a transgenic plant and DNA specific primers are designed for PCR. PCR may be performed under the same conditions as used for preparation of the above plasmid. Then, amplification products may be subjected to, e.g., agarose gel electrophoresis, polyacrylamide gel electrophoresis or capillary electrophoresis, followed by staining with ethidium bromide, SYBR Green solution, etc. If the amplification products are detected as a single band, it can be confirmed that the plant has been transformed. Alternatively, primers which have been labeled with a fluorescent dye or the like may be used in PCR to thereby detect amplification products. Further, it is also possible to use techniques in which amplification products are bound onto a solid phase (e.g., a microplate) and confirmed by fluorescence or enzymatic reaction, etc.

Once a transgenic whole plant whose genome carries the polynucleotide of the present invention has been obtained, progeny plants may be obtained by sexual or asexual reproduction of the whole plant. Moreover, from such a whole plant or progeny plants thereof or clones thereof, for example, seeds, fruits, cuttings, tubers, root tubers, rootstocks, calli, protoplasts or the like may be obtained and used to achieve mass production of the whole plant. Thus, the present invention also encompasses a whole plant into which the polynucleotide of the present invention has been introduced in an expressible form, or progeny plants of the whole plant which have the same properties as the whole plant, or tissues derived from the whole plant and progeny plants thereof.

In addition, transformation techniques for various plants have already been reported. Transgenic plants according to the present invention include plants of the family Solanaceae (e.g., eggplant, tomato, hot pepper, potato, tobacco, stramonium, Chinese lantern plant, petunia, calibrachoa, nierembergia), plants of the family Leguminosae (e.g., soybean, adzuki bean, peanut, kidney bean, broad bean, Bird's foot trefoil), plants of the family Rosaceae (e.g., strawberry, Japanese apricot, cherry tree, rose, blueberry, blackberry, bilberry, cassis, raspberry), plants of the family Caryophyllaceae (e.g., carnation, gypsophila), plants of the family Asteraceae (e.g., chrysanthemum, stevia, gerbera, sunflower, daisy), plants of the family Orchidaceae (e.g., orchid), plants of the family Primulaceae (e.g., cyclamen), plants of the family Gentianaceae (e.g., showy prairie gentian, gentian), plants of the family Iridaceae (e.g., freesia, iris, gladiolus), plants of the family Scrophulariaceae (e.g., snapdragon, torenia), stone crop (kalanchoe), plants of the family Liliaceae (e.g., lily, tulip), plants of the family Convolvulaceae (e.g., morning glory, ivy-leaved morning glory, moonflower, sweet potato, cypress vine, evolvulus), plants of the family Hydrangeaceae (e.g., hydrangea, deutzia), plants of the family Cucurbitaceae (e.g., bottle gourd), plants of the family Geraniaceae (e.g., pelargonium, geranium), plants of the family Oleaceae (e.g., weeping forsythia), plants of the family Vitaceae (e.g., grape), plants of the family Theaceae (e.g., *Camellia sinensis*, camellia, tea plant), plants of the family Gramineae (e.g., rice, barley, wheat, oat, rye, maize, foxtail millet, Japanese barnyard millet, kaoliang, sugar cane, bamboo, wild oat, finger millet, sorghum, Manchurian wild rice, job's tears, pasture grass), plants of the family Moraceae (e.g., mulberry, hop, paper mulberry, rubber tree, cannabis), plants of the family Rubiaceae (e.g., coffee tree, gardenia), plants of the family Fagaceae (e.g., oak, beech, Japanese emperor oak), plants of the family Pedaliaceae (e.g., sesame), plants of the family Rutaceae (e.g., bitter orange, Citrus junos, satsuma mandarin, Japanese pepper tree), plants of the family Brassicaceae (e.g., red cabbage, flowering cabbage, Japanese radish, *Arabidopsis thaliana*, Chinese colza, cabbage, broccoli, cauliflower), and plants of the family Lamiacea (e.g., salvia, perilla, lavender, skullcap).

Examples of preferred plants include *Camellia sinensis*, hop (*Humulus lupulus*), sweet potato (*Ipomoea batatas*), snapdragon (*Antirrhinum majus*), *stevia* (*Stevia rebaudiana*), *Arabidopsis thaliana*, grape (*Vitaceae vitis*) and so on.

The whole plant transformed with the polynucleotide of the present invention (hereinafter referred to as "the plant of the present invention" or "the whole plant of the present invention") is rich in hexenol glycosides when compared to the wild-type counterpart.

Moreover, the plant of the present invention or the whole plant of the present invention is rich in glycosides of the substrate of the present invention when compared to the wild-type counterpart.

The plant of the present invention can be easily obtained as a perfect whole plant by being grown from a seed, a cuttage, a bulb or the like of the plant of the present invention.

Thus, the plant of the present invention encompasses a whole plant, a plant organ (e.g., leaf, petal, stem, root, seed, bulb), a plant tissue (e.g., epidermis, phloem, parenchyma, xylem, vascular bundle, palisade tissue, spongy parenchyma) or a cultured plant cell, or alternatively, various forms of plant cells (e.g., suspension cultured cells), a protoplast, a leaf section, a callus and so on.

3. Extract of Transformant and Use Thereof

In another embodiment, the present invention also provides an extract of the above transformant. Since the transformant of the present invention is rich in hexenol glycosides when compared to the wild-type counterpart, an extract of the transformant is considered to contain hexenol glycosides at high concentrations.

Likewise, the transformant of the present invention is rich in glycosides of the substrate of the present invention when compared to the wild-type counterpart, and hence an extract of the transformant is considered to contain glycosides of the substrate of the present invention at high concentrations.

Such an extract of the transformant of the present invention can be obtained as follows: the transformant is homogenized with, e.g., glass beads, a homogenizer or a sonicator and the resulting homogenate is centrifuged to collect the supernatant. In addition, a further extraction step may also be provided in accordance with extraction procedures for hexenol glycosides as mentioned above.

The extract of the transformant of the present invention can be provided for use in, e.g., production of aromatics and/or industrial raw materials according to standard practice.

In another embodiment, the present invention also provides a food, a beverage, an aromatic, a pharmaceutical preparation, an industrial raw material, and/or an aromatic cosmetic product, each containing hexenol glycosides produced by the method of the present invention. Such a food, an aromatic, a pharmaceutical preparation and/or an industrial raw material, each containing the extract of the transformant of the present invention, may be prepared in a routine manner. In this way, such a food, an aromatic, a pharmaceutical preparation and/or an industrial raw material, each containing the extract of the transformant of the present invention, contains hexenol glycosides produced by using the method of the present invention.

4. Plant Modified to Suppress the Expression of Hexenol Glycosyltransferase

As to green leaf volatiles accumulated in glycosylated form within plant cells, glycosylation is inhibited when suppressing the expression of a protein endogenously occurring in plants and having glycosylation activity on hexenol. As a result, the thus modified plants will contain more volatile hexenol in non-glycosylated form and can be expected to release a stronger green aroma.

The present invention therefore provides a plant modified to suppress the expression of a protein having glycosylation activity on hexenol.

More specifically, such a protein having glycosylation activity on hexenol (hereinafter referred to as "hexenol glycosyltransferase") is encoded by a polynucleotide of any one selected from the group consisting of (a) to (e) shown below:

(a) a polynucleotide containing the nucleotide sequence shown in SEQ ID NO: 1, 3, 5, 7, 9, 11, 13, 15, 17, 19, 21, 23, 25, 27, 29 or 31;

(b) a polynucleotide encoding a protein which consists of the amino acid sequence shown in SEQ ID NO: 2, 4, 6, 8, 10, 12, 14, 16, 18, 20, 22, 24, 26, 28, 30 or 32;

(c) a polynucleotide encoding a protein which consists of an amino acid sequence with deletion, substitution, insertion and/or addition of 1 to 40 amino acids in the amino acid sequence shown in SEQ ID NO: 2, 4, 6, 8, 10, 12, 14, 16, 18, 20, 22, 24, 26, 28, 30 or 32 and which has glycosylation activity on hexenol;

(d) a polynucleotide encoding a protein which has an amino acid sequence sharing a sequence identity of 90% or more with the amino acid sequence shown in SEQ ID NO: 2, 4 or 6 and which has glycosylation activity on hexenol; and (e) a polynucleotide which is hybridizable under high stringent conditions with a polynucleotide consisting of a nucleotide sequence complementary to the nucleotide sequence shown in SEQ ID NO: 1, 3, 5, 7, 9, 11, 13, 15, 17, 19, 21, 23, 25, 27, 29 or 31 and which encodes a protein having glycosylation activity on hexenol.

The polynucleotides (a) to (e) are as defined above in the section "2. Non-human transformant rich in hexenol glycosides."

In the above polynucleotides (a) and (e), "the nucleotide sequence shown in SEQ ID NO: 1, 3, 5, 7, 9, 11, 13, 15, 17, 19, 21, 23, 25, 27, 29 or 31" is intended in some embodiment to mean "the nucleotide sequence shown in SEQ ID NO: 1 or 3," "the nucleotide sequence shown in SEQ ID NO: 5, 7, 9 or 11," "the nucleotide sequence shown in SEQ ID NO: 13, 15 or 17," "the nucleotide sequence shown in SEQ ID NO: 19, 21 or 23," "the nucleotide sequence shown in SEQ ID NO: 25," "the nucleotide sequence shown in SEQ ID NO: 27 or 29" or "the nucleotide sequence shown in SEQ ID NO: 31."

In the above polynucleotides (b) to (d), "the amino acid sequence shown in SEQ ID NO: 2, 4, 6, 8, 10, 12, 14, 16, 18, 20, 22, 24, 26, 28, 30 or 32" is intended in some embodiment to mean "the amino acid sequence shown in SEQ ID NO: 2 or 4," "the amino acid sequence shown in SEQ ID NO: 6, 8, 10 or 12," "the amino acid sequence shown in SEQ ID NO: 14, 16 or 18," "the amino acid sequence shown in SEQ ID NO: 20, 22 or 24," "the amino acid sequence shown in SEQ ID NO: 26," "the amino acid sequence shown in SEQ ID NO: 28 or 30" or "the amino acid sequence shown in SEQ ID NO: 32."

Specific examples of means to suppress the expression of hexenol glycosyltransferase include substances capable of reducing the expression level of messenger RNA (mRNA) for this enzyme, as exemplified by low molecular compounds, hormones, proteins and nucleic acids. In one embodiment, such a substance may be a nucleic acid capable of suppressing the functions or expression of a gene encoding the above enzyme. Examples of such a nucleic acid include hairpin-shaped shRNAs (short hairpin RNAs) or double-stranded RNAs (dsRNAs) which produce siRNAs (small interfering RNAs) for RNA interference (RNAi), as well as antisense nucleic acids, decoy nucleic acids, or aptamers, etc. These inhibitory nucleic acids are able to suppress the expression of the above gene. The target gene to be inhibited which encodes hexenol glycosyltransferase consists of any one of the above polynucleotides (a) to (e), and sequence information can be obtained for each polynucleotide. In the present invention, it is possible to use, as a target region to be inhibited, not only a coding region, but also a non-coding region of the gene encoding hexenol glycosyltransferase.

RNA interference (RNAi) is a multi-step process proceeding through a number of stages. First of all, dsRNA or shRNA expressed from an RNAi expression vector is recognized by Dicer and cleaved into siRNAs of 21 to 23 nucleotides. These siRNAs are then integrated into an RNAi targeting complex, which is called the RNA-induced silencing complex (RISC), and the complexes between RISC and siRNAs bind to target mRNA containing sequences complementary to the siRNA sequences and thereby cleave the mRNA. The target mRNA is cleaved in the center of its region complementary to the siRNA, finally leading to rapid degradation of the target mRNA and reduced protein expression levels. The most potent siRNA duplexes are known to be sequences of 21 nucleotides in length, each comprising a 19 bp duplex with an overhang of two uridine residues at the 3'-terminal end (Elbashir S. M. et al., Genes and Dev, 15, 188-200 (2001)).

In general, a target sequence on mRNA may be selected from the cDNA sequence corresponding to the mRNA sequence. However, the present invention is not limited to this region.

siRNA molecules may be designed on the basis of the criteria well known in the art. For example, as a target segment in target mRNA, it is possible to select a segment covering 15 to 30 contiguous bases, preferably 19 to 25 contiguous bases, preferably starting with AA, TA, GA or CA. siRNA molecules have a GC ratio of 30% to 70%, preferably 35% to 55%. Alternatively, a target sequence for RNAi may be selected as appropriate as described in Ui-Tei K. et al. ((2004) Nucleic Acids Res. 32, 936-948).

For introduction of siRNA into cells, it is possible to use, e.g., procedures in which synthesized siRNA is ligated to plasmid DNA and then introduced into cells, or procedures in which double-stranded RNA is annealed.

In the present invention, shRNA may also be used for providing RNAi effect. shRNA is an RNA molecule called short hairpin RNA, which has a stem-loop structure because some single-stranded regions form complementary strands with other regions.

shRNA may be designed to form a stem-loop structure as a part thereof. For example, assuming that a sequence covering a certain region is designated as sequence A, and a strand complementary to the sequence A is designated as sequence B, shRNA is designed to comprise the sequence A, a spacer and the sequence B linked in this order on a single RNA strand and to have an overall length of 45 to 60 bases. The spacer may also have any length.

Although the sequence A is a sequence covering a partial region of the target gene encoding hexenol glycosyltransferase, there is no particular limitation on the target region and any region may be selected as a candidate for the target region. In addition, the sequence A has a length of 19 to 25 bases, preferably 19 to 21 bases.

Further, in the present invention, microRNA may be used to inhibit the expression of hexenol glycosyltransferase. microRNA (miRNA) is an intracellular single-stranded RNA molecule having a length of about 20 to 25 bases and is a kind of ncRNA (non-coding RNA) which is considered to have the function of regulating the expression of other genes. miRNA is generated through processing upon transcription into RNA and is present as a nucleic acid capable of forming a hairpin structure which suppresses the expression of a target sequence.

Since miRNA is also an inhibitory nucleic acid based on RNAi, miRNA may also be designed and synthesized in the same manner as in the case of shRNA or siRNA.

Expression vectors for RNAi may be readily prepared with a commercially available DNA/RNA synthesizer (e.g., Applied Biosystems model 394) on the basis of pMuniH1 plasmid, pSINsi vector (Takara Bio Inc., Japan), pSIF1-H1 (System Biosciences, Inc.), etc. Examples of expression vectors for RNAi include, but are not limited to, pSPB1876 (WO2004/071467). Expression vectors for RNAi may be prepared by entrusting their preparation to third parties such as Cosmo Bio Co., Ltd. (Japan), Takara Bio Inc. (Japan), Invitrogen, Promega, etc.

A method for producing a plant modified to suppress the expression of hexenol glycosyltransferase may comprise the following steps.

(1) Step of Introducing an Expression Vector for RNAi (e.g., siRNA Expression Vector or miRNA Expression Vector) Against Hexenol Glycosyltransferase into a Host Plant or a Portion Thereof Introduction of an expression vector for RNAi into a host plant may be accomplished in the same manner as described above in the section "2. Non-human transformant rich in hexenol glycosides." The host plant may be any of a whole plant or a portion thereof, i.e., a plant organ (e.g., leaf, petal, stem, root, seed), a plant tissue (e.g., epidermis, phloem, parenchyma, xylem, vascular bundle, palisade tissue, spongy parenchyma) or a cultured plant cell, or alternatively, various forms of plant cells (e.g., suspension cultured cells), a protoplast, a leaf section, a callus and so on. The type of plant is also as described above in the section "2. Non-human transformant rich in hexenol glycosides."

(2) Step of Growing the Transgenic Plant Obtained in the Above Step (1)

If the host plant used in the above step (1) is a portion of a whole plant, such as a plant organ, a plant tissue, a plant cell, a protoplast, a leaf section or a callus, the resulting transformant may be grown in an appropriate environment until a perfect whole plant is formed. With respect to techniques for growing a portion of a whole plant into a perfect whole plant, reference may be made to the descriptions in the following document: Biochemistry Experiments Vol. 41, An Introduction to Plant Cell Technology, Japan Scientific Societies Press, ISBN 4-7622-1899-5.

Upon cultivation of the thus obtained plant which is modified to suppress the expression of a gene for hexenol glycosyltransferase, the hexenol aglycon can be produced efficiently.

In the same manner, RNA interference may be performed on polynucleotides (f) to (j) shown below to thereby prepare a whole plant rich in the substrate of the present invention in non-glycosylated form:

(f) a polynucleotide containing the nucleotide sequence shown in SEQ ID NO: 1;

(g) a polynucleotide encoding a protein which consists of the amino acid sequence shown in SEQ ID NO: 2;

(h) a polynucleotide encoding a protein which consists of an amino acid sequence with deletion, substitution, insertion and/or addition of 1 to 40 amino acids in the amino acid sequence shown in SEQ ID NO: 2 and which has glycosylation activity on any one or more substrates selected from the group consisting of hexenol, geraniol, eugenol, benzyl alcohol, 2-phenylethanol and linalool;

(i) a polynucleotide encoding a protein which has an amino acid sequence sharing a sequence identity of 90% or more with the amino acid sequence shown in SEQ ID NO: 2 and which has glycosylation activity on any one or more substrates selected from the group consisting of hexenol, geraniol, eugenol, benzyl alcohol, 2-phenylethanol and linalool; and (j) a polynucleotide which is hybridizable under high stringent conditions with a polynucleotide consisting of a nucleotide sequence complementary to the nucleotide sequence shown in SEQ ID NO: 1 and which encodes a protein having glycosylation activity on any one or more substrates selected from the group consisting of hexenol, geraniol, eugenol, benzyl alcohol, 2-phenylethanol and linalool.

Upon cultivation of the thus obtained plant which is modified to suppress the expression of a gene for glycosyltransferase acting on the substrate of the present invention, the aglycon of the substrate of the present invention can be produced efficiently.

5. Processed Product of a Plant Modified to Suppress the Expression of a Gene for Hexenol Glycosyltransferase Today, not only natural flowers (e.g., soil-grown plants, potted plants, cut flowers), but also processed products of natural flowers are sold as products for plant appreciation. Due to their strong green aroma, plants modified to suppress the expression of a gene for hexenol glycosyltransferase or for glycosyltransferase acting on the substrate of the present invention are also very useful as materials for such processed products of natural flowers. Thus, another embodiment of the present invention is a processed product of a plant (e.g., natural flower, cut flower) modified to suppress the expression of a gene for hexenol glycosyltransferase or a portion of the plant (e.g., leaf, petal, stem, root, seed, bulb). Examples of such a processed product include, but are not limited to, pressed flowers, dried flowers, preserved flowers, material flowers, resin-embedded products, etc.

6. Extract of a Plant Modified to Suppress the Expression of Hexenol Glycosyltransferase and Use Thereof In another embodiment, the present invention also provides an extract of the above plant modified to suppress the expression of a gene for hexenol glycosyltransferase or for glycosyltransferase acting on the substrate of the present invention. Since the plant modified to suppress the expression of a gene for hexenol glycosyltransferase or for glycosyltransferase acting on the substrate of the present invention is rich in hexenol aglycon or in the aglycon of the substrate of the present invention when compared to the wild-type counterpart, an extract of the modified plant is considered to contain hexenol aglycon or the aglycon of the substrate of the present invention at high concentration.

The above extract can be extracted in the same manner as described above for the extract of the transformant of the present invention.

The thus obtained extract can be provided for use in, e.g., production of aromatics and/or industrial raw materials according to standard practice.

In another embodiment, the present invention also provides an aromatic and/or an industrial raw material, each containing the above extract. Such an aromatic and/or an industrial raw material, each containing the above extract, may be prepared in a routine manner. In this way, such an aromatic and/or an industrial raw material, each containing the extract of the plant modified to suppress the expression of a gene for hexenol glycosyltransferase or for glycosyltransferase acting on the substrate of the present invention, contains hexenol aglycon or the aglycon of the substrate of the present invention generated by using the plant modified to suppress the expression of hexenol glycosyltransferase or glycosyltransferase acting on the substrate of the present invention.

The aromatic and industrial raw material of the present invention are of the same type and composition as described above in the section "3. Extract of transformant and use thereof."→Since the relevant detailed descriptions in Section 3. have been deleted, this sentence should also be deleted.

7. Screening Method for a Plant Rich in Hexenol Glycosides or a Plant Rich in Hexenol Aglycon The present invention provides a screening method for a plant rich in hexenol aglycon. More specifically, the above method comprises steps (1) to (3) shown below:

(1) the step of extracting mRNA from a test plant;

(2) the step of allowing hybridization between the above mRNA or cDNA prepared from the above mRNA and a polynucleotide which is hybridizable under high stringent conditions with a polynucleotide consisting of a nucleotide sequence complementary to the polynucleotide of the present invention; and (3) the step of detecting the above hybridization.

The above step (1) may be accomplished by extracting mRNA from a test plant. Although mRNA may be extracted from any site of the test plant, preferred are petals. Once mRNA has been extracted, cDNA may be prepared from the mRNA through reverse transcription.

The above step (2) may be accomplished as follows: a polynucleotide or oligonucleotide consisting of a nucleotide sequence complementary to the polynucleotide of the present invention is used as a probe or primer and allowed to hybridize with the mRNA extracted above under high stringent conditions. High stringent conditions are as already described above. Such a polynucleotide or oligonucleotide has a length of preferably 5 to 500 bp, more preferably 10 to 200 bp, and even more preferably 10 to 100 bp. The polynucleotide or oligonucleotide may be readily synthesized with various automatic synthesizers (e.g., AKTA oligopilot plus 10/100 (GE Healthcare)), or alternatively, its synthesis may be entrusted to a third party (e.g., Promega or Takara), etc.

When the polynucleotide consisting of a nucleotide sequence complementary to the polynucleotide of the present invention is used as a probe in the step (2), the step (3) may be accomplished by commonly used techniques for detection of hybridization, such as Southern blotting, Northern blotting (Sambrook, Fritsch and Maniatis, "Molecular Cloning: A Laboratory Manual" 2nd Edition (1989), Cold Spring Harbor Laboratory Press), microarrays (Affymetrix; see U.S. Pat. Nos. 6,045,996, 5,925,525 and 5,858,659), TaqMan PCR (Sambrook, Fritsch and Maniatis, "Molecular Cloning: A Laboratory Manual" 2nd Edition (1989), Cold Spring Harbor Laboratory Press), or fluorescent in situ hybridization (FISH) (Sieben V. J. et al., (2007-06). IET Nanobiotechnology 1 (3): 27-35). On the other hand, when the polynucleotide consisting of a nucleotide sequence complementary to the polynucleotide of the present invention is used as a primer in the step (2), the step (3) may be accomplished by PCR amplification and the subsequent analysis of the resulting amplification products by electrophoresis or sequencing (Sambrook, Fritsch and Maniatis, "Molecular Cloning: A Laboratory Manual" 2nd Edition (1989), Cold Spring Harbor Laboratory Press), etc., to detect hybridization.

A whole plant in which hybridization was more often detected can be regarded as expressing higher levels of a protein having glycosylation activity on hexenol compounds than other whole plants, and hence such a whole plant is predicted to be rich in hexenol glycosides.

On the other hand, a whole plant in which hybridization was less often detected shows lower expression of a protein having glycosylation activity on hexenol compounds than other whole plants, and hence such a whole plant is predicted to be rich in hexenol aglycon and to release a strong green aroma.

8. Composition for Producing a Hexenol Glycoside

The present invention provides a composition for producing a hexenol glycoside, which comprises the protein of the present invention and a solvent (hereinafter referred to as "the composition of the present invention").

The composition of the present invention may further comprise a UDP-sugar.

The protein of the present invention, a hexenol glycoside and a UDP-sugar are as described above.

The solvent used for this purpose is not limited in any way, but preferred is a neutral buffer of pH 6.0 to 8.0 (e.g., sodium phosphate buffer or potassium phosphate buffer).

When the composition of the present invention is mixed and reacted with hexenol (and a UDP-sugar), a hexenol glycoside can be easily produced.

The reaction of the protein of the present invention with a UDP-sugar and a hexenol molecule is as described above.

EXAMPLES

The present invention will now be described in more detail by way of the following examples, which are not intended to limit the scope of the present invention.

Example 1 Search for *Camellia sinensis*-Derived Candidate Genes

The molecular biological procedures used in this example are as described in Molecular Cloning (Sambrook et al., Cold Spring Harbour Laboratory Press, 2001), unless otherwise specified in detail.

Since tea is known to contain glycosides of green leaf volatiles, phages (about 300,000 pfu) from the cDNA library of *Camellia sinensis* (cultivar Yabukita) (Non-patent Document 4) were used for comprehensive screening of glycosyltransferase genes using *Arabidopsis thaliana* glycosyltransferase. Fragments amplified with the *Arabidopsis thaliana* UGT85A3 gene specific primer set (SEQ ID NOs: 33 and 34) and UGT85A1 gene specific primer set (SEQ ID NOs: 35 and 36) were used as screening probes to conduct plaque hybridization screening.

CACC-NdeI-UGT85A3-Fw (the underlined nucleotides represent an NdeI recognition site):

(SEQ ID NO: 33)
5'-CACCCATATGGGATCCCGTTTTGTTTC-3'

XhoI-stop-UGT85A3-Rv (the underlined nucleotides represent an XhoI recognition site):

(SEQ ID NO: 34)
5'-CTCGAGTTACGTGTTAGGGATCTTTC-3'

NdeI-AtUGT85A1-Fw (the underlined nucleotides represent an NdeI recognition site):

(SEQ ID NO: 35)
CACCCATATGGGATCTCAGATCATTCATAAC

BamHI-AtUGT85A1-Rv (the underlined nucleotides represent a BamHI recognition site):

(SEQ ID NO: 36)
GGATCCTTAATCCTGTGATTTTTGTCCCAAAAG

The probes were each labeled by PCR using a non-radioisotope DIG-nucleic acid detection system (Roche Diagnostics) under the conditions recommended by the manufacturer. A PCR reaction solution used for this purpose was prepared to contain 1 μl of template DNA (total cDNA from *Arabidopsis thaliana*), 1×Taq buffer (TakaRa Bio), 0.2 mM dNTPs, primers (0.2 pmol/μl each) and rTaq polymerase (1.25 U). This PCR reaction solution was reacted at 94° C. for 5 minutes, followed by 30 cycles of reaction at 94° C. for 1 minute, at 52° C. for 1 minute and at 72° C. for 2 minutes, and final treatment at 72° C. for 5 minutes. This PCR product was applied to a Mini Quick Spin column (Roche) to remove the primers and unreacted dNTPs, and the resulting product was used as a screening probe.

Library screening and positive clone detection were accomplished by using a non-radioisotope DIG-nucleic acid detection system (Roche Diagnostics) in accordance with the method recommend by the manufacturer. Hybridization was conducted overnight at 37° C. in 5×SSC containing 30% formamide, and the membranes were washed with 5×SSC and 1% SDS at 55° C. for 20 minutes. Approximately 500,000 plaques were screened. After secondary screening, the resulting positive clones were analyzed with a DNA Sequencer model 3100 (Applied Biosystems) by primer walking with synthetic oligonucleotide primers, thus obtaining cDNA sequences. The resulting cDNA sequences were analyzed for homology using the Blastx program (blast.ncbi.nlm.nih.gov/Blast.cgi) to thereby obtain *Camellia sinensis* UGT genes (Cs_UGT) including Cs_UGT_C30 and Cs_UGT85like_C1.

Example 2 Expression of *Camellia sinensis*-Derived Candidate Genes in *E. coli* Cells Primers specific to these UGTs were designed and *Camellia sinensis* cDNA was used as a template to amplify the genes by PCR. These amplification products were each subcloned into pENTR-TOPO Directional vector (Invitrogen) in accordance with the method recommend by the manufacturer. The clones were analyzed with a DNA Sequencer model 3100 (Applied Biosystems) by primer walking with synthetic oligonucleotide primers, thus confirming that there was no PCR-induced mutation in the inserted fragments.

Each Cs_UGT fragment of approximately 1.4 kb was excised by means of the NdeI and XhoI or SalI or BamHI restriction enzyme sites added to the primers, and then ligated to the NdeI and XhoI or BamHI sites of an *E. coli* expression vector, pET15b (Novagen), to thereby obtain an *E. coli* expression vector for each enzyme gene. Each vector was designed to carry the open reading frame of the Cs_UGT gene in frame with a His tag located upstream of the NdeI site so as to express a chimeric protein having the His tag fused to the N-terminal end of Cs_UGT.

Example 3 Enzyme Expression and Purification

To clarify the biochemical functions of these enzymes, these enzymes were allowed to be expressed in *E. coli* cells. The Cs_UGT *E. coli* expression plasmids obtained above were each used to transform *E. coli* strain BL21(DE3) in a standard manner. The resulting transformants were each cultured overnight at 37° C. under shaking conditions in 4 ml of a 50 μg/ml ampicillin-containing LB medium (10 g/l typtone pepton, 5 g/l yeast extract, 1 g/l NaCl). After reaching the resting phase, each cultured solution (4 ml) was inoculated into a medium of the same composition (80 ml) and cultured at 37° C. under shaking conditions. At the time point where the cell turbidity (OD600) reached about 0.5, IPTG was added at a final concentration of 0.5 mM, followed by culturing at 18° C. for 20 hours under shaking conditions.

The following manipulations were all performed at 4° C. Each cultured transformant was collected by centrifugation (5,000×g, 10 min) and then added to and suspended in Buffer S [20 mM HEPES buffer (pH 7.5), 20 mM imidazole, 14 mM β-mercaptoethanol] at 1 ml/g cell. Subsequently, the suspension was homogenized by ultrasonication (15 sec, repeated 8 times) and then centrifuged (15,000×g, 15 min). The resulting supernatant was collected as a crude enzyme solution. The crude enzyme solution was loaded onto a His SpinTrap column (GE Healthcare) which had been equilibrated with Buffer S, followed by centrifugation (70×g, 30 sec). After washing with the buffer, proteins bound to the column were eluted stepwise with 5 ml each of Buffer S containing 100 mM and 500 mM imidazole. Each elution fraction was subjected to buffer replacement with 20 mM HEPES buffer (pH 7.5), 14 mM β-mercaptoethanol through a Microcon YM-30 unit (Amicon) (magnification of dialysis: ×1000).

As a result of SDS-PAGE separation and the subsequent CBB staining or Western blotting analysis with anti-HisTag antibody, in the fraction eluted with 200 mM imidazole, a protein was confirmed at approximately 56.7 kDa, which is the putative molecular weight for the HisTag-fused Cs_UGT chimeric protein. This fraction was used for enzyme reaction.

Example 4 Enzyme Reaction and Reaction Product Analysis

Standard enzyme reaction conditions are as follows. A reaction solution (2 mM UDP-glucose, 1.5 mM sugar acceptor substrate, 100 mM potassium phosphate buffer (pH 7.5), 25 μl purified Cs_UGT enzyme solution) was prepared in a volume of 50 μl with distilled water and reacted at 30° C. for 1 hour.

The enzyme reaction solution (5 μl) was analyzed by LC-MS under the following conditions.

LC Conditions

Column: CAPCELL PAK C18-UG120 (2.0 mm I.D.×150 mm)

Mobile phase: A: MilliQ water (containing 0.05% formic acid), B: acetonitrile

Gradient: linear concentration gradient of B from 15% to 90% over 15 minutes

Flow rate: 0.2 ml per minute

Column oven: 40° C.

Injection volume: 5 μl

MS Conditions

ESI (negative mode)

SIM mode: (m/z 261, 297, 307)

As a result of analysis, a product was detected around a retention time of 6 minutes in the reactions with Cs_UGT85like_C1 and Cs_UGT_C30. The same monoglucoside as the reference standard was detected (FIGS. 1B and 1C: Samples 2 and 3). In comparison with the reference standard cis-3-hexenyl monoglucoside (m/z 261 for cis-3-hexenyl monoglucoside (molecular weight: 261), m/z 307 for a formic acid adduct of cis-3-hexenyl monoglucoside (molecular weight: 307) (FIG. 5C: Sample 15), the products catalyzed by Cs_UGT851ike_C1 and Cs_UGT_C30 were each found to be cis-3-hexenyl monoglucoside. In addition, the reaction between an empty vector-derived sample and cis-3-hexenol showed no new product (FIG. 1A: Sample 1). These results indicate that Cs_UGT85like_C1 and Cs_UGT_C30 are glycosyltransferases having glycosylation activity on cis-3-hexenol.

Example 5 Analysis of Homolog Enzymes in Plant Lines Other than *Camellia sinensis*

Since green leaf volatiles are found in a wide range of land plants, a search was conducted for UGTs causing glycosylation of green leaf volatiles derived from other plant lines on the basis of homology with the sequence of *Camellia sinensis* Cs_UGT_C30. Activity screening was conducted in the same manner as shown in the above Examples, indicating that the following UGTs were found to have similar activity to generate cis-3-hexenyl monoglucoside (FIGS. 2A to 2C: Samples 4 to 6, FIGS. 3A to 3C: Samples 7 to 9, FIGS. 4A to 4C: Samples 10 to 12, FIGS. 5A to 5C: Samples 13 to 14, FIGS. 6A to 6C: Samples 16 to 18).

TABLE 2

| Source species | Gene name | Data |
|---|---|---|
| *Humulus lupulus* | Hl_UGT119 | FIG. 2A: Sample 4 |
| | Hl_UGT127 | FIG. 2B: Sample 5 |
| | Hl_UGT279 | FIG. 2C: Sample 6 |
| | Hl_UGT251 | FIG. 3A: Sample 7 |
| *Ipomoea batatas* | Ib_UGT42 | FIG. 3B: Sample 8 |
| *Antirrhinum majus* | Am_UGT207 | FIG. 3C: Sample 9 |
| *Stevia rebaudiana* | Sr_UGT85C2 | FIG. 4A: Sample 10 |
| | Sr_UGT85A5 | FIG. 4B: Sample 11 |
| | Sr_UGT85C1 | FIG. 4C: Sample 12 |
| *Arabidopsis thaliana* | At_UGT85A1 | FIG. 5A: Sample 13 |
| | At_UGT85A3 | FIG. 5B: Sample 14 |
| *Vitaceae vitis* | Vv_UGT020 | FIG. 6A: Sample 16 |
| | Vv_UGT734 | FIG. 6B: Sample 17 |
| *Arabidopsis thaliana* | Vv_UGT744 | FIG. 6C: Sample 18 |

These results indicate that glycosyltransferases on green leaf volatiles have a certain correlation between their sequence and functions, and are present in a wide range of land plants.

Example 6 Analysis of Specificity for Sugar Acceptors

As shown above, CsUGTC30 isolated from *Camellia sinensis* was found to have the ability to cause glucosylation of green leaf volatiles (GLV) typified by cis-3-hexen-1-ol (hexenol).

Leaves of *Camellia sinensis* are known to contain not only glycosides of green leaf volatiles, but also monoterpene-based aroma components (e.g., geraniol, linalool) and aromatic-based aroma components in the form of glycosides (Non-patent Document: Wang et al., J. Agric. Food Chem. 2000, 48, 5411-5418).

Next, to clarify the substrate specificity of CsUGTC30, geraniol, linalool, eugenol, benzyl alcohol, 2-phenylethanol, quercetin and cyanidin were each used as a substrate to determine the relative activity of transglucosylation with the above enzyme and under the above enzyme reaction conditions. The reaction time was set to 30 minutes at 30° C.

As a result, CsUGTC30 showed the highest activity on geraniol and showed the second highest activity on eugenol and benzyl alcohol at the same level as on hexenol.

Figure 8:
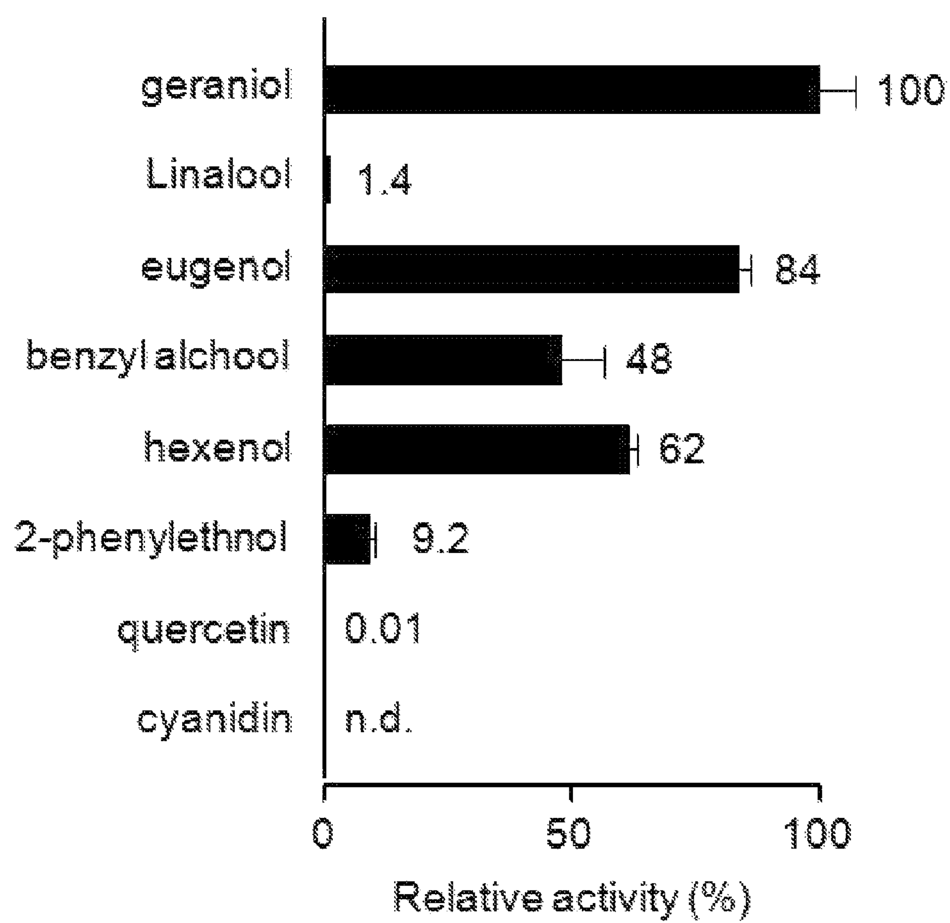
FIG. 8 shows the relative enzyme activity measured for a recombinant CsUGTC30 protein. The activity on geraniol is set to 100%.

CsUGTC30 was also found to have transglycosylation activity on 2-phenylethanol and linalool. In contrast, CsUGTC30 showed no transglycosylation activity on the flavonoids quercetin (flavonol) and cyanidin (anthocyanidin), which are non-aroma components (FIG. 8: the activity on geraniol is set to 100%).

These results indicate that CsUGTC30 has the ability to cause glycosylation not only of green leaf volatiles, but also of monoterpene alcohol-based and aromatic-based aroma components.

Example 7 Analysis of Specificity for Sugar Acceptors

Figure 9:
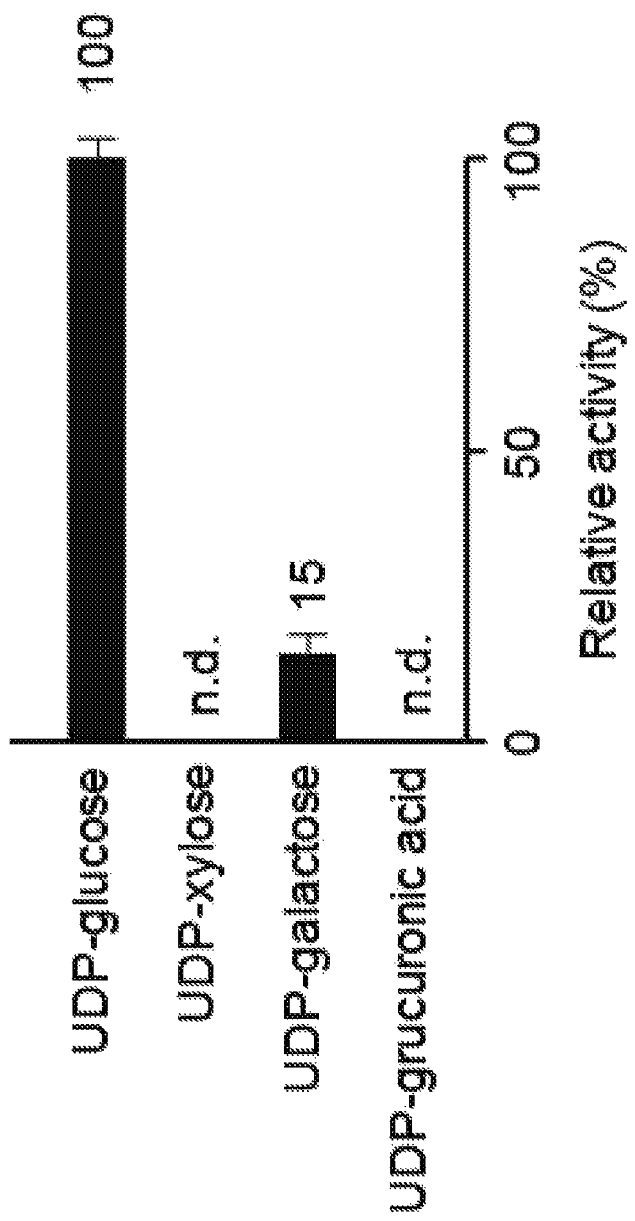
FIG. 9 shows the relative activity of CsUGTC30 on sugar donors. The activity on UDP-glucose is set to 100%.

Next, CsUGTC30 was studied for its specificity for sugar donors. For details of procedures, reference was made to the previously reported procedures (Non-patent Document 2: Noguchi et al. (2009) Plant Cell, 21: 1556-1572). Using geraniol as a sugar acceptor, 4 types of UDP-sugars, i.e., UDP-glucose, UDP-xylose, UDP-galactose and UDP-glucuronic acid were used for enzyme reaction. The reaction time was set to 30 minutes at 30° C. As a result, CsUGTC30 showed high specificity for UDP-glucose, and its specificity for UDP-galactose was 15% of that for UDP-glucose (FIG. 9: the activity on UDP-glucose is set to 100%). Thus, CsUGTC30 was found to use UDP-glucose as a major sugar donor.

Example 8 Analysis of Specificity for Sugar Acceptors

To clarify the expression region of CsUGTC30 responsible for glucosylation of aroma components, quantitative RT-PCR analysis was conducted in various organs. In the manner described above, total RNAs were extracted from old leaves, mature leaves, young leaves, young leaves (treated in the dark), stems, roots and flowers of *Camellia sinensis* (cultivar Yabukita), followed by quantitative RT-PCR in the same manner as previously reported (Non-patent Document 3: Ono et al. (2010) Plant Cell, 22: 2856-2871). For treatment in the dark, the light was shielded for 24 hours with aluminum. The specific primers for CsUGTC30 (SEQ ID NOs: 37 and 38) and the specific primers for internal standard 18S rRNA (SEQ ID NOs: 39 and 40) used here are as shown below.

```
Specific primer for CsUGTC30 (forward):
qRT-Cs-30-FW2
                                        (SEQ ID NO: 37)
5'-TGTCCAAAGAGGCATTTTCC-3'

Specific primer for CsUGTC30 (Reverse):
qRT-Cs-30-RV2
                                        (SEQ ID NO: 38)
5'-AAGGATGGCATGTCCTTGAG-3'

Specific primer for 18S rRNA (forward):
Cs 18srRNA-FW
                                        (SEQ ID NO: 39)
5'-CAACTTTCGATGGTAGGATAGTG-3'

Specific primer for 18S rRNA (Reverse):
Cs 18srRNA-RV
                                        (SEQ ID NO: 40)
5'-GGCTATAGACTCGTTGAATACATC-3'
```

Figure 10:
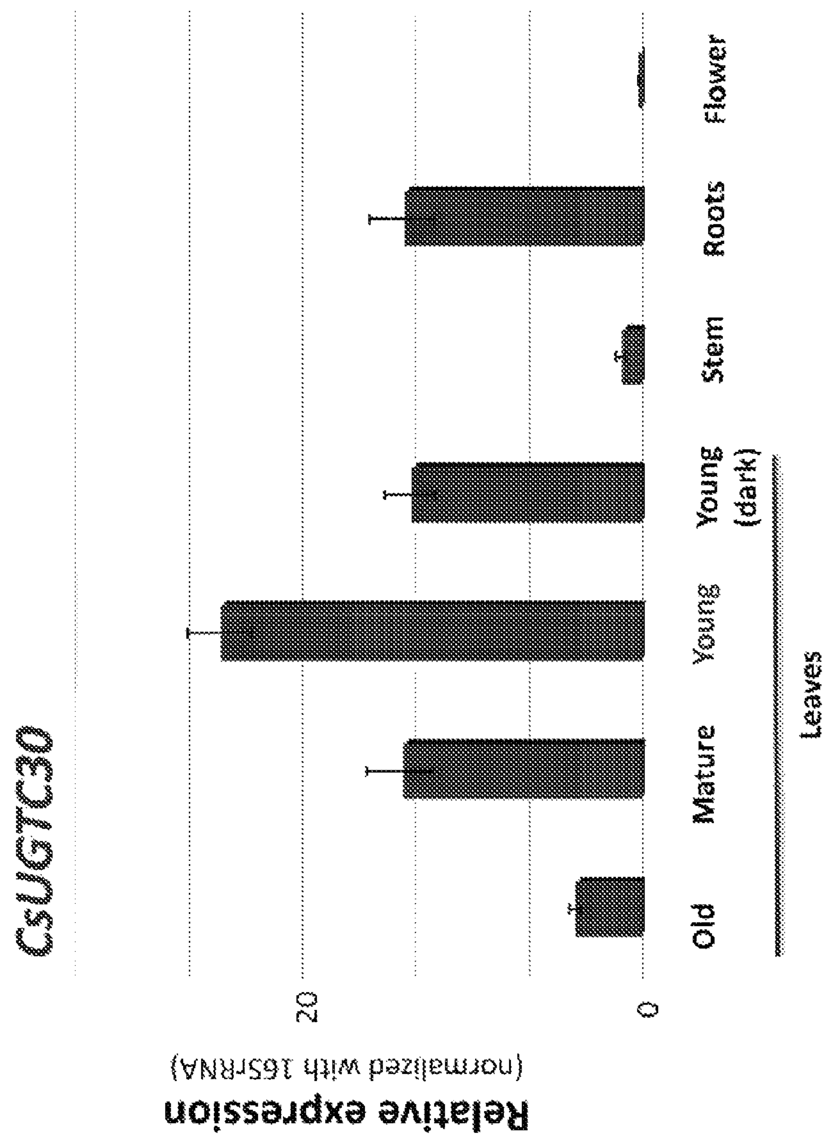
FIG. 10 shows the results of gene expression analysis of the CsUGTC30 gene in various organs.

As a result, CsUGTC30 was confirmed to be expressed at the highest level in young leaves (FIG. 10). This result is in agreement with the finding that glycosides of aroma components in *Camellia sinensis* are accumulated in leaves. These results indicate that CsUGTC30 is expressed in young leaves and is an important enzyme responsible for glucosylation of various aroma components to thereby generate water-soluble aroma precursors in leaves.

INDUSTRIAL APPLICABILITY

In food products containing various plant extracts including *Camellia sinensis* which is a source material for green tea, oolong tea, black tea and others, green leaf volatiles are important components determining the quality of the food products. For this reason, there is a demand for techniques to control green leaf volatiles. From a plurality of plant lines, the inventors of the present invention have now found several types of glycosyltransferases having glycosylation activity on green leaf volatiles. When using or controlling these enzymes, a green aroma can be enhanced or reduced. The present invention provides food products with modified aroma or an important tool for development of aromatics.

Sequence Listing Free Text

SEQ ID NOs: 33 to 40: synthetic DNAs

Sequence Listing

The invention claimed is:

1. A method for producing a hexenol glycoside, comprising:

contacting an isolated, purified or extracted protein with a UDP-sugar and a hexenol molecule to cause glycosylation of the hexenol molecule and to thereby produce a hexenol glycoside;

wherein the isolated, purified or extracted protein has glycosylation activity on the hexenol molecule and is selected from the group consisting of:

(a) a protein consisting of the amino acid sequence of SEQ ID NO: 2 or 4;

(b) a protein consisting of the amino acid sequence of SEQ ID NO: 2 or 4, except that no more than 1 to 24 amino acids are deleted, substituted, inserted, and/or added; and (c) a protein comprising an amino acid sequence that has 95% or more sequence identity with the amino acid sequence of SEQ ID NO: 2 or 4.

2. The method according to claim 1, wherein the UDP-sugar is a UDP-hexose.

3. The method according to claim 2, wherein the hexose of the UDP-hexose is selected from the group consisting of glucose, mannose and galactose.

4. The method according to claim 1, further comprising purifying the hexenol glycoside.

5. A method for producing a hexenol glycoside, comprising:

providing a cell comprising a polynucleotide encoding a protein, wherein said cell expresses said protein, and said cell is a microorganism or a transgenic plant cell, and contacting within or outside of the cell said protein with a UDP-sugar and a hexenol molecule to cause glycosylation of the hexenol molecule and to thereby produce a hexenol glycoside, wherein said polynucleotide comprises a nucleotide sequence encoding said protein and an expression control region that controls expression of said nucleotide sequence and wherein the nucleotide sequence encoding said protein and/or the expression control region is heterologous to said cell, wherein said protein has glycosylation activity on the hexenol molecule and is selected from the group consisting of:

(a) a protein consisting of the amino acid sequence of SEQ ID NO: 2 or 4;

(b) a protein consisting of the amino acid sequence of SEQ ID NO: 2 or 4, except that no more than 1 to 24 amino acids are deleted, substituted, inserted, and/or added; and (c) a protein comprising an amino acid sequence that has 95% or more sequence identity with the amino acid sequence of SEQ ID NO: 2 or 4.

6. The method according to claim 5, wherein the UDP-sugar is a UDP-hexose.

7. The method according to claim 6, wherein the hexose of the UDP-hexose is selected from the group consisting of glucose, mannose and galactose.

8. The method according to claim 5, further comprising purifying the hexenol glycoside.

9. The method according to claim 5, wherein the transgenic plant cell is from a transformed whole plant, a transformed plant organ, a transformed plant tissue, transformed cultured plant cells, or from a progeny plant of a transgenic whole plant whose genome comprises the polynucleotide encoding the protein having glycosylation activity on the hexenol molecule.

* * * * *